(12) United States Patent
Liu et al.

(10) Patent No.: US 12,343,965 B2
(45) Date of Patent: Jul. 1, 2025

(54) FLUORINATED ELASTOMERS FOR BRAIN PROBES AND OTHER APPLICATIONS

(71) Applicant: President and Fellows of Harvard College, Cambridge, MA (US)

(72) Inventors: Jia Liu, Cambridge, MA (US); Paul Claude Henri Le Floch, Cambridge, MA (US); Hao Sheng, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 74 days.

(21) Appl. No.: 18/278,819

(22) PCT Filed: Mar. 9, 2022

(86) PCT No.: PCT/US2022/019430
§ 371 (c)(1),
(2) Date: Aug. 24, 2023

(87) PCT Pub. No.: WO2022/192319
PCT Pub. Date: Sep. 15, 2022

(65) Prior Publication Data
US 2024/0131828 A1 Apr. 25, 2024
US 2024/0227370 A9 Jul. 11, 2024

Related U.S. Application Data

(60) Provisional application No. 63/290,732, filed on Dec. 17, 2021, provisional application No. 63/159,623, filed on Mar. 11, 2021.

(51) Int. Cl.
*B32B 27/08* (2006.01)
*A61N 1/05* (2006.01)

(52) U.S. Cl.
CPC ............ *B32B 27/08* (2013.01); *A61N 1/0531* (2013.01); *A61N 1/0534* (2013.01); *A61N 1/0539* (2013.01); *B32B 2250/03* (2013.01)

(58) Field of Classification Search
None
See application file for complete search history.

(56) References Cited

U.S. PATENT DOCUMENTS 5,064,593 A 11/1991 Tamaru et al.
6,306,975 B1 10/2001 Zhao et al.
(Continued)

FOREIGN PATENT DOCUMENTS

WO 2019/031324 A1 2/2019

OTHER PUBLICATIONS

Invitation to Pay Additional Fees mailed May 6, 2022 for International Application No. PCT/US2022/019430.
(Continued)

*Primary Examiner* — Ramsey Zacharia
(74) *Attorney, Agent, or Firm* — Wolf, Greenfield & Sacks, P.C.

(57) ABSTRACT

Articles and devices comprising fluorinated polymers, as well as methods of preparing fluorinated polymers, are generally described. In some cases, such fluorinated elastomers can be used for sensing neural activity, e.g., by encapsulating electronic circuits, or other applications. Furthermore, according to certain embodiments, polymers can, surprisingly, be directly deposited onto layers comprising low molecular weight fluorinated polymers, e.g., without swelling in the presence of certain solvents. Some embodiments are generally directed to devices and methods for treating fluorinated polymers and subsequently depositing material onto the treated fluorinated polymers. This may (Continued)

allow the fabrication and patterning of multilayered articles comprising fluorinated elastomers.

16 Claims, 33 Drawing Sheets

(56) References Cited

U.S. PATENT DOCUMENTS

| | | | |
|---|---|---|---|
| 7,049,380 | B1 | 5/2006 | Chang et al. |
| 8,355,768 | B2 | 1/2013 | Masmanidis et al. |
| 2007/0219551 | A1 | 9/2007 | Honour et al. |
| 2008/0315459 | A1 | 12/2008 | Zhang et al. |
| 2011/0237921 | A1 | 9/2011 | Askin, III et al. |
| 2012/0157804 | A1 | 6/2012 | Rogers et al. |
| 2013/0004773 | A1 | 1/2013 | Klun et al. |
| 2013/0228950 | A1 | 9/2013 | DeSimone et al. |
| 2013/0245416 | A1 | 9/2013 | Yarmush et al. |
| 2015/0306376 | A1 | 10/2015 | Novotny et al. |
| 2016/0007874 | A1 | 1/2016 | Ma et al. |
| 2017/0209079 | A1 | 7/2017 | Kinser et al. |
| 2020/0235039 | A1* | 7/2020 | Kim ................ H01L 23/293 |
| 2020/0257199 | A1 | 8/2020 | Liu et al. |
| 2020/0362089 | A1* | 11/2020 | Meserole ............ C09D 175/04 |
| 2021/0057750 | A1 | 2/2021 | Yamazaki et al. |
| 2023/0141530 | A1* | 5/2023 | Shi .................. C08G 18/289 528/70 |
| 2024/0041376 | A1 | 2/2024 | Liu et al. |

OTHER PUBLICATIONS

International Search Report and Written Opinion mailed Jul. 20, 2022 for International Application No. PCT/US2022/019430.

International Preliminary Report on Patentability mailed Sep. 21, 2023 for International Application No. PCT/US2022/019430.

Adolphs, The unsolved problems of neuroscience. Trends Cogn Sci. Apr. 2015;19(4):173-5. doi: 10.1016/j.tics.2015.01.007. Epub Feb. 20, 2015.

Agyeman et al., Perspective: Does personalized medicine hold the future for medicine? J Pharm Bioallied Sci. Jul.-Sep. 2015;7(3):239-44. doi: 10.4103/0975-7406.160040.

Ajiboye et al., Restoration of reaching and grasping movements through brain-controlled muscle stimulation in a person with tetraplegia: a proof-of-concept demonstration. Lancet. May 6, 2017;389(10081):1821-1830. doi: 10.1016/S0140-6736(17)30601-3. Epub Mar. 28, 2017.

Angotzi et al., In A low-power, low-area modular architecture for high density neural probes, 2015 7th International IEEE/EMBS Conference on Neural Engineering (NER), Apr. 22-24, 2015; 2015; pp. 521-524.

Barrer, Permeability of organic polymers. J. Chem. Soc. Faraday Trans. Mar. 12, 1940;35:644-648.

Chung et al., High-Density, Long-Lasting, and Multi-region Electrophysiological Recordings Using Polymer Electrode Arrays. Neuron. Jan. 2, 2019;101(1):21-31.e5. doi: 10.1016/j.neuron.2018.11.002. Epub Nov. 27, 2018.

Dalvi et al., Molecular origins of fluorocarbon hydrophobicity. Proc Natl Acad Sci U S A. Aug. 3, 2010;107(31):13603-7. doi: 10.1073/pnas.0915169107. Epub Jul. 19, 2010.

Dayan et al., Theoretical neuroscience: computational and mathematical modeling of neural systems. 2001.

Geise et al., Fundamental water and salt transport properties of polymeric materials. Prog. Polym. Sci. 2014;39 (1):1-42.

Green et al., Elastic and conductive hydrogel electrodes. Nat Biomed Eng. Jan. 2019;3(1):9-10. doi: 10.1038/s41551-018-0342-7.

Guan et al., Elastocapillary self-assembled neurotassels for stable neural activity recordings. Sci Adv. Mar. 27, 2019;5(3):eaav2842. doi: 10.1126/sciadv.aav2842.

Hong et al.,Novel electrode technologies for neural recordings. Nat Rev Neurosci. Jun. 2019;20(6):330-345. doi: 10.1038/s41583-019-0140-6. Erratum in: Nat Rev Neurosci. Apr. 16, 2019.

Hu et al., Optically transparent, amphiphilic networks based on blends of perfluoropolyethers and poly (ethylene glycol). Journal of the American Chemical Society. 2008; 130 (43): 14244-14252.

Hu et al., Photochemically cross-linked perfluoropolyether-based elastomers: Synthesis, physical characterization, and biofouling evaluation. Macromolecules. 2009;42 (18): 6999-7007.

Jun et al., Fully integrated silicon probes for high-density recording of neural activity. Nature. Nov. 8, 2017;551(7679):232-236. doi: 10.1038/nature24636.

Kim et al., Fluoropolymer-Based Flexible Neural Prosthetic Electrodes for Reliable Neural Interfacing. ACS Appl Mater Interfaces. Dec. 20, 2017;9(50):43420-43428. doi: 10.1021/acsami.7b12364. Epub Dec. 7, 2017.

Kim et al., Simultaneous photoadhesion and photopatterning technique for passivation of flexible neural electrodes based on fluoropolymers. Sci Rep. Dec. 7, 2020;10(1):21386. doi: 10.1038/s41598-020-78494-w.

Lacour et al., Materials and technologies for soft implantable neuroprostheses. Nature Reviews Materials. Sep. 27, 2016;1(10):16063.

Le Floch et al., Fundamental Limits to the Electrochemical Impedance Stability of Dielectric Elastomers in Bioelectronics. Nano Lett. Jan. 8, 2020;20(1):224-233. doi: 10.1021/acs.nanolett.9b03705. Epub Dec. 10, 2019.

Le Floch et al., Stretchable Seal. ACS Applied Materials & Interfaces. 2018; 10 (32): 27333-27343.

Li et al., Cyborg Organoids: Implantation of Nanoelectronics via Organogenesis for Tissue-Wide Electrophysiology. Nano Letters 2019;19 (8):5781-5789.

Liu et al., Soft and elastic hydrogel-based microelectronics for localized low-voltage neuromodulation. Nature Biomedical Engineering 2019; 3 (1): 58-68.

Liu et al., Intrinsically stretchable electrode array enabled in vivo electrophysiological mapping of atrial fibrillation at cellular resolution. Proc Natl Acad Sci U S A. Jun. 30, 2020;117(26):14769-14778. doi: 10.1073/pnas.2000207117. Epub Jun. 15, 2020.

Liu et al., Syringe-injectable electronics. Nat Nanotechnol. Jul. 2015;10(7):629-636. doi: 10.1038/nnano.2015.115. Epub Jun. 8, 2015.

Lopez et al., An Implantable 455-Active-Electrode 52-Channel CMOS Neural Probe. IEEE Journal of Solid-State Circuits 2014;49 (1): 248-261.

Markram, Seven challenges for neuroscience. Funct Neurol. Jul.-Sep. 2013;28(3):145-51.

Masciullo et al., Perfluoropolyether (PFPE) Intermediate Molds for High-Resolution Thermal Nanoimprint Lithography. Nanomaterials (Basel). Aug. 10, 2018;8(8):609. doi: 10.3390/nano8080609.

Minev et al., Biomaterials. Electronic dura mater for long-term multimodal neural interfaces. Science. Jan. 9, 2015;347(6218):159-63. doi: 10.1126/science.1260318.

Musk, Neuralink. An Integrated Brain-Machine Interface Platform With Thousands of Channels. J Med Internet Res. Oct. 31, 2019;21(10):e16194. doi: 10.2196/16194.

Nguyen et al., Mechanically-compliant intracortical implants reduce the neuroinflammatory response. J Neural Eng. Oct. 2014;11(5):056014. doi: 10.1088/1741-2560/11/5/056014. Epub Aug. 15, 2014.

Rolland et al., Solvent-resistant photocurable "liquid teflon" for microfluidic device fabrication. Journal of the American Chemical Society. 2004;126 (8): 2322-2323.

Soekadar et al., Hybrid EEG/EOG-based brain/neural hand exoskeleton restores fully independent daily living activities after quadriplegia. Science Robotics. 2016,;1 (1),:1-8.

Steinmetz et al., Neuropixels 2.0: A miniaturized high-density probe for stable, long-term brain recordings. Science. Apr. 16, 2021;372(6539):eabf4588. doi: 10.1126/science.abf4588.

Takeuchi et al., Parylene flexible neural probes integrated with microfluidic channels. Lab on a Chip. 2005; 5(5): 519-523.

Tau et al., Normal development of brain circuits. Neuropsychopharmacology. Jan. 2010;35(1):147-68. doi: 10.1038/npp.2009.115.

(56) References Cited

OTHER PUBLICATIONS

Tringides et al., Viscoelastic surface electrode arrays to interface with viscoelastic tissues. Nat Nanotechnol. Sep. 2021; 16(9):1019-1029. doi: 10.1038/s41565-021-00926-z. Epub Jun. 17, 2021.

Vachicouras et al., Microstructured thin-film electrode technology enables proof of concept of scalable, soft auditory brainstem implants. Sci Transl Med. Oct. 16, 2019;11(514):eaax9487. doi: 10.1126/scitranslmed.aax9487.

Van Amerongen, Influence of structure of elastomers on their permeability to gases. J. Polym. Sci. 1950;5(3):307-332.

Van Den Brand et al., Restoring voluntary control of locomotion after paralyzing spinal cord injury. Science. 2012; 336 (6085):1182-1185.

Van Dommelen et al., Mechanical properties of brain tissue by indentation: Interregional variation. Journal of the Mechanical Behavior of Biomedical Materials. 2010; 3(2): 158-166.

Vitale et al., Direct photolithography of perfluoropolyethers for solvent-resistant microfluidics. Langmuir 2013;29 (50): 15711-15718.

Viventi et al., Flexible, foldable, actively multiplexed, high-density electrode array for mapping brain activity in vivo. Nat Neurosci. Nov. 13, 2011;14(12):1599-605. doi: 10.1038/nn.2973.

Williams et al., High-resolution PFPE-based molding techniques for nanofabrication of high-pattern density, sub-20 nm features: a fundamental materials approach. Nano letters 2010;10(4):1421-1428.

Yang et al., Bioinspired neuron-like electronics. Nat Mater. May 2019;18(5):510-517. doi: 10.1038/s41563-019-0292-9. Epub Feb. 25, 2019.

Yuk et al., 3D printing of conducting polymers. Nat Commun. Mar. 30, 2020;11(1):1604. doi: 10.1038/s41467-020-15316-7.

European Office Action dated Oct. 20, 2023 for Application No. EP 22767842.2.

Extended European Search Report mailed Jan. 9, 2025 for International Application No. EP 22767842.2.

Rolland et al., Solvent-resistant photocurable liquid fluoropolymers for microfluidic device fabrication [corrected]. J Am Chem Soc. Mar. 3, 2004;126(8):2322-3. doi: 10.1021/ja031657y. Erratum in: J Am Chem Soc. Jul. 7, 2004;126(26):8349.

\* cited by examiner $$\sigma = 2\frac{q^2}{kT}D * S * C_{out} \qquad (1)$$

FIG. 11D
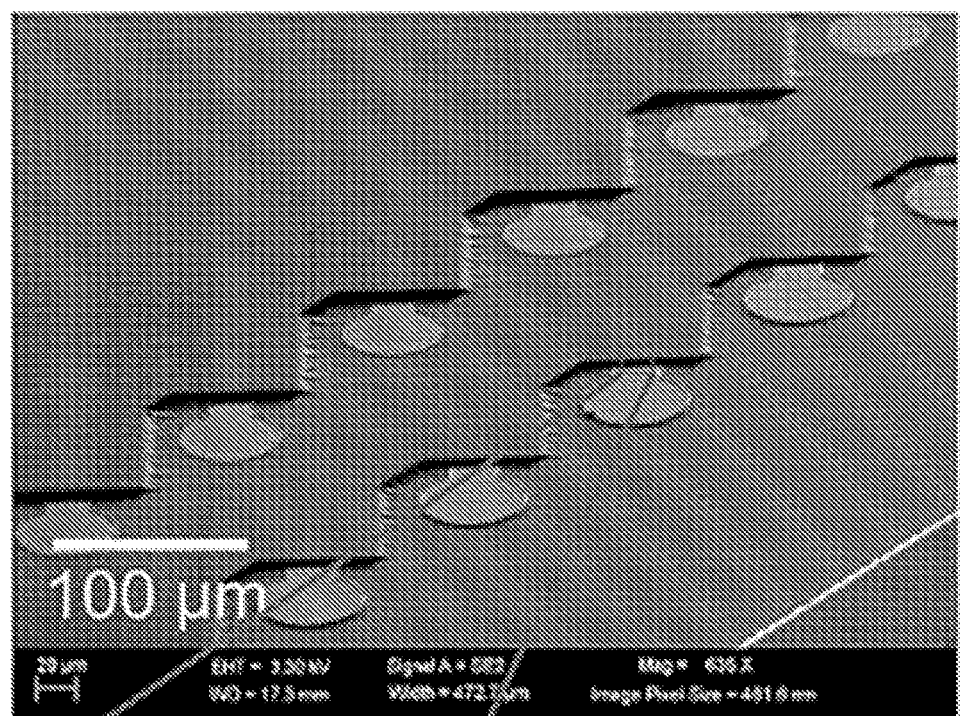
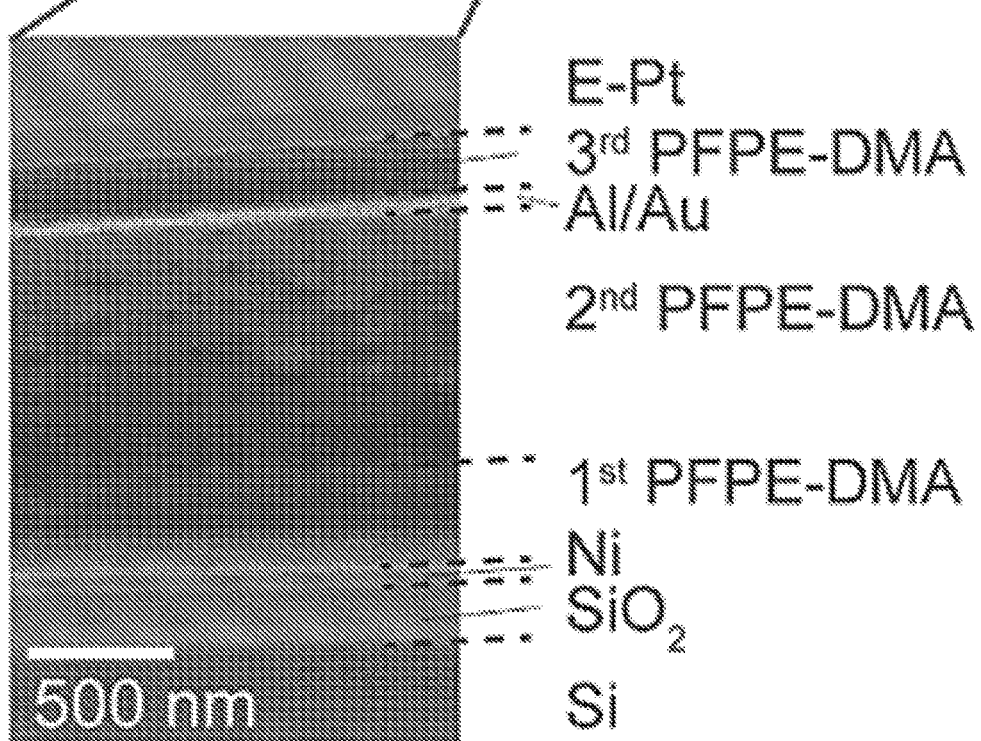
FIG. 11E

Counter Electrode

FLUORINATED ELASTOMERS FOR BRAIN PROBES AND OTHER APPLICATIONS

RELATED APPLICATIONS

This application is a national stage filing under 35 U.S.C. § 371 of International Patent Application Serial No. PCT/US2022/019430, filed Mar. 9, 2022, entitled "Fluorinated Elastomers for Brain Probes and Other Applications," which claims priority to U.S. Provisional Application No. 63/159,623, filed Mar. 11, 2021, and entitled "Perfluorinated Elastomers for Brain Probes and Other Applications"; and to U.S. Provisional Application No. 63/290,732, filed Dec. 17, 2021, and entitled "Fluorinated Elastomers for Brain Probes and Other Applications," which are each incorporated herein by reference in their entirety for all purposes.

GOVERNMENT SUPPORT

This invention was made with government support under 2011754 awarded by National Science Foundation (NSF). The government has certain rights in this invention.

TECHNICAL FIELD

Articles and methods related to fluorinated elastomers are generally described.

BACKGROUND

Decoding neural signals is of fundamental importance to bridge the existing gap of knowledge between our molecular understanding of synaptic circuits and behavioral neurosciences. Understanding neurodegenerative diseases or brain circuitry in general, and increasing the bandwidth of brain-machine interfaces for novel medical devices such as neuroprostheses or deep brain stimulators, are, to name a few, potential applications that would benefit from advanced neural interface technologies. However, probing the dynamic of neural network on a sufficiently large spatial and temporal scale to understand neural encoding requires simultaneous measurements on tens, if not hundreds of thousands of neurons, in vivo, over time. Moreover, each neuron itself can have tens to hundreds of thousands of synaptic connections, which can extend throughout the entire volume of the brain. Therefore, chronically stable and brain-wide activity mapping is needed to understand the connectome of the brain.

Various microelectrode array technologies have been developed to measure single-unit extracellular action potentials of hundreds to thousands of neurons simultaneously and over period of times extending from weeks to months. Nevertheless, further increasing the density of electrical sensors, such as microelectrodes or transistors, has been limited by the immune response caused by the mechanical mismatch between the probes and the brain tissues. Accordingly, improvements are needed.

SUMMARY

Articles and methods related to fluorinated elastomers are generally described. The subject matter of the present invention involves, in some cases, interrelated products, alternative solutions to a particular problem, and/or a plurality of different uses of one or more systems and/or articles.

One aspect is generally directed towards an article. According to some embodiments, the article comprises: a first layer comprising a first fluorinated polymer; a second layer, bonded to the first layer; and a third layer, bonded to the second layer, comprising a second fluorinated polymer.

Another aspect is generally directed towards an article. In some embodiments, the article comprises: a substrate configured to be implanted into an organ of a subject, the substrate comprising a plurality of electrodes, the substrate comprising a first layer comprising a first fluorinated polymer, a second layer bonded to the first layer, and a third layer comprising a second fluorinated polymer bonded to the second layer.

Yet another aspect is generally directed towards an article. In some embodiments, the article comprises: a substrate comprising a plurality of electrodes, the substrate comprising a first layer comprising a first fluorinated polymer, a second layer bonded to the first layer, and a third layer comprising a second fluorinated polymer bonded to the second layer, a ratio of to greater or equal to $10^{-9}$ electrodes/micron$^2$ Still another aspect is generally directed towards an article. In some embodiments, the article comprises: a substrate comprising a plurality of electrodes, the substrate comprising a first layer comprising a first fluorinated polymer, a second layer bonded to the first layer, and a third layer comprising a second fluorinated polymer bonded to the second layer, wherein the electrodes have a number density greater than or equal to $10^{-3}$ electrodes/micron$^2$.

Another embodiment is generally directed towards an article. In some embodiments, the article comprises: a substrate comprising a plurality of electrodes, the substrate comprising a first layer comprising a first fluorinated polymer, a second layer bonded to the first layer, and a third layer comprising a second fluorinated polymer bonded to the second layer, wherein the substrate has an overall elastic modulus of less than or equal to $10^6$ Pa.

Yet another aspect is generally directed towards an article. According to some embodiments, the article comprises: a first layer comprising a first fluorinated polymer; a second layer, bonded to the first layer; and a third layer, bonded to the second layer, and comprising a second fluorinated polymer; wherein the third layer has an average thickness H in microns, wherein the polymer on the substrate exhibits a reduction in specific electrochemical impedance modulus (i.e., the electrochemical impedance modulus, normalized to the geometry of the sample) at 1 kHz of no more than 50% after being immersed for in 10×PBS solution at 65° C. for a period of time of at least 1*H$^2$ days.

One aspect is generally directed to an article, comprising a first layer comprising perfluoropolyether; a second layer, bonded to the first layer; and a third layer, bonded to the second layer, comprising perfluoropolyether.

Another aspect is generally directed to an article, comprising a perfluoropolyether having a weight-average molecular weight of less than 8 kDa, wherein the perfluoropolyether is on a semiconductor substrate.

Yet another aspect is generally directed to an article, comprising a polymer, comprising a cross-linked perfluoropolyether, on a substrate, wherein the polymer, when formed into an article having a minimum dimension of at least 0.3 micrometers that is immersed in 1,3-bis(trifluoromethyl)benzene for a period of greater than or equal to 9 seconds, dried in nitrogen, and measured at 1 kHz, exhibits a specific electrochemical impedance modulus of at least $10^6$ ohm-m.

Still another aspect is generally directed to an article, comprising a polymer, comprising a cross-linked perfluoropolyether, on a substrate, wherein the polymer on the substrate exhibits a reduction in specific electrochemical impedance modulus at 1 kHz of no more than 50% after being immersed for 100 days in phosphate buffer solution.

Another aspect is generally directed towards a method. In some embodiments, the method comprises: inserting, into an organ of a subject, a substrate comprising a plurality of electrodes, the substrate comprising a first layer comprising a first fluorinated polymer, a second layer bonded to the first layer, and a third layer comprising a second fluorinated polymer bonded to the second layer.

Still another aspect is generally directed towards a method. In some embodiments, the method comprises: depositing a fluorinated polymer on a substrate; applying an inert gas plasma to the fluorinated polymer to form a treated fluorinated polymer; and depositing a material onto the treated fluorinated polymer.

Yet another aspect is generally directed towards a method. In some embodiments, the method comprises: depositing a fluorinated polymer on a substrate; treating the fluorinated polymer to render it susceptible to deposition; and depositing a second fluorinated polymer onto the treated fluorinated polymer.

One aspect is generally directed towards a method. In some embodiments, the method comprises: depositing a fluorinated polymer on a substrate; treating the fluorinated polymer to render it susceptible to deposition; depositing a material forming a plurality of electrodes onto the treated fluorinated polymer.

Another aspect is generally directed towards a method. In some embodiments, the method comprises: determining electrical signals from a plurality of electrodes on a substrate at least partially contained within a subject, wherein the substrate comprises a first layer comprising a first fluorinated polymer, a second layer bonded to the first layer, and a third layer comprising a second fluorinated polymer bonded to the second layer.

Still another aspect is generally directed towards a method. In some embodiments, the method comprises: determining electrical activity of a single cell within a living subject using an electrode on a substrate in contact with the cell over at least 5 days, wherein the substrate comprises a layer comprising a fluorinated polymer.

Yet another aspect is generally directed towards a method. In some embodiments, the method comprises: determining electrical signals from a plurality of electrodes on a substrate at least partially contained within a subject, wherein the substrate has an overall elastic modulus of less than or equal to $10^6$ Pa and comprises a layer comprising a fluorinated polymer.

One aspect is generally directed towards a method. In some embodiments, the method comprises: electrically stimulating cells within a subject using a plurality of electrodes on a substrate, wherein the substrate comprises a first layer comprising a fluorinated polymer, a second layer bonded to the first layer, and a third layer comprising a fluorinated polymer bonded to the second layer.

Another aspect is directed to a method, comprising depositing perfluoropolyether on a substrate; applying an argon plasma to the perfluoropolyether to form a treated perfluoropolyether; and depositing a material onto the treated perfluoropolyether.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale unless otherwise indicated. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 11B-11E present images of exemplary article designed for use as a neural sensor, according to certain embodiments;

DETAILED DESCRIPTION

Figure 1:
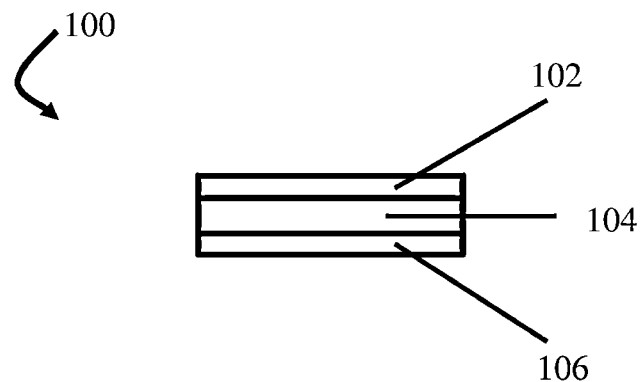
FIG. 1 presents a cross-sectional schematic illustration of an exemplary article comprising a perfluorinated polymer, according to certain embodiments.

Large scale, brain-wide neuron activity mapping is important for deciphering neuron population dynamics for neuroscience, understanding and alleviating neurological disorders, and building high-bandwidth BMIs for neuroprosthetics and communications. Ultimately, brain mapping aims to simultaneously record activities from millions, if not billions, of neurons at single-cell, millisecond spatiotemporal resolution in a chronically stable manner. "Tissue-like" thin-film electronics with subcellular feature size and tissue-level flexibility can allow a gliosis-free implantation, chronically recording stable neuron activity at single-cell, single-spike spatiotemporal resolution for applications in neuroscience, bioelectronic medicine, and brain-machine interface (BMI). One major challenge is scaling up the number of microelectrodes in tissue-like electronics without using rigid materials that are fundamentally mismatched with the mechanical properties of the brain. Another challenge is the tendency of soft electronics to degrade in the brain's chemical environment, which degrades most polymeric materials over time. Articles and sensors comprising fluorinated polymers offer a significant advantage for electronic devices such as neural implants. For example, fluorinated polymers may have desirable electrical and/or mechanical properties for brain implants, and may exhibit exceptional long-term stability under physiological conditions.

The present disclosure recognizes the importance of fluorinated polymers for brain implants, and provides inventive methods of preparing multilayered articles comprising multiple fluorinated polymer layers. These articles may demonstrate some of the outstanding properties of fluorinated polymers. For example, some exemplary, non-limiting articles described herein comprise $10^{-3}$ electrodes per micron$^2$ and/or have an overall elastic modulus of less than or equal to $10^6$ Pa. This number of electrodes per micron$^2$ represents a tenfold increase in the area number density of electrodes, relative to sensors with a comparable elastic modulus, according to some embodiments. Moreover, this elastic modulus represents a thousandfold reduction in the elastic modulus of a brain-sensor having a comparable number of electrodes per micron$^2$, according to some embodiments.

Although nanofabrication techniques can be used to produce bioelectronics for in vivo use, the long-term stability of these devices under physiological conditions, as well as the mismatch between their mechanical properties and the mechanical properties of human tissue, limit the scope of these technologies. In some embodiments, fluorinated polymers (such as perfluorinated polymers) have been identified as a way to address these limitations. Thus, the present disclosure, in certain aspects, generally relates to perfluorinated polymers with long-term stability in near-physiological conditions that can be used in a variety of articles and devices. For example, in some embodiments, these perfluorinated polymers are used for implants, e.g., as coatings. In some embodiments, the present disclosure relates to fluorinated polymers in general, including fluorinated polymers with long-term stability, such as perfluorinated polymers. In some embodiments these fluorinated polymers are used for implants, e.g., as coatings.

Some aspects of the present disclosure are directed to systems and methods of preparing fluorinated polymers, including articles containing such polymers, e.g., devices, sensors, implants, circuits, coated substrates, or the like. In addition, some aspects of the present disclosure are directed to systems and methods of preparing perfluorinated polymers, including articles containing such polymers, e.g., devices, sensors, implants, circuits, coated substrates, or the like. Without wishing to be bound by any theory, it is believed that the superhydrophobicity of perfluorinated polymers can make fabrication of articles and devices comprising perfluorinated polymers challenging. Thus, in one embodiment, the present disclosure is directed towards methods of treating a perfluorinated polymer (e.g., a perfluoropolyether) that unexpectedly allows the deposition of additional material bonded to the perfluorinated polymer. The perfluorinated polymer may be treated by applying a plasma (e.g., argon plasma) to the perfluorinated polymer. The additional material, in some cases, is additional perfluorinated polymer that can increase the overall thickness of a perfluorinated polymer layer. Thus, in some embodiments, the fabrication of surprisingly thick perfluorinated polymer layers (e.g., thicker than 300 nanometers) is disclosed. This surprising thickness may beneficially improve the stability and/or mechanical properties of perfluorinated polymers in electronics. In contrast, other techniques are not able to produce such thick perfluorinated polymer layers on articles or devices.

In certain aspects, the present disclosure is directed towards articles and/or devices comprising fluorinated polymers. One, non-limiting example is provided here, for the purpose of illustration. Other embodiments are possible, as described in greater detail below. In certain aspects, the present disclosure is directed towards articles and/or devices comprising perfluorinated polymers. For instance, some embodiments are directed to the fabrication of articles having perfluorinated polymers. For example, the article may have a first layer of a perfluorinated polymer (e.g., a perfluoropolyether), a second layer (e.g., aluminum, gold, or the like) that is bonded to the first layer, and a third layer of a perfluorinated polymer (e.g., a perfluoropolyether) bonded to the third layer. For example, FIG. 1 presents article 100 with first layer 102 of a perfluorinated polymer, second layer 104 bonded to first layer 102, and third layer 106 of a perfluorinated polymer bonded to second layer 104. Such an article may cover at least a portion of an electronic circuit, or other applications such as described herein. In some cases, such articles and circuits may prove useful as components of bioelectronic devices. As noted above, layered perfluorinated polymers have not previously been described.

It should be understood, however, that these examples are presented by way of explanation and not limitation; other aspects and embodiments are also discussed below.

Certain aspects of the disclosure are directed towards polymers and, in particular, towards perfluorinated polymers. According to certain embodiments, the polymer is a fluorinated polymer. For example, the polymer may be a perfluorinated polymer, e.g., a polymer wherein the carbon atoms within a portion of the polymer are only bound to fluorine and/or other heteroatoms, rather than hydrogen. The polymer may also be a fluorinated but nonperfluorinated polymer, as described in greater detail below. In some embodiments, the polymer comprises or consists essentially of a perfluoropolyether. The polymer may be any suitable perfluoropolyether. For example, the polymer may contain perfluoropolyether (PFPE), polytetrafluoroethylene (PTFE), perfluoropolyether dimethylacrylate (PFPE-DMA), fluorinated ethylene-propylene (FEP), perfluoroalkoxy polymer (PFA), or polychlorotrifluoroethylene (PCTFE). The polymer may be a copolymer, such tetrafluoroethylene propylene (TFE). For example, in some embodiments, the polymer is perfluoropolyether dimethylacrylate.

Articles and devices comprising perfluorinated polymers, as well as methods of preparing perfluorinated polymers, are generally described. In some cases, such perfluorinated elastomers can be used for sensing neural activity, e.g., by encapsulating electronic circuits, or other applications. Furthermore, according to certain embodiments, polymers can, surprisingly, be directly deposited onto layers comprising low molecular weight perfluorinated polymers, e.g., without swelling in the presence of certain solvents. Some embodiments are generally directed to devices and methods for treating perfluorinated polymers and subsequently depositing material onto the treated perfluorinated polymers. This may allow the fabrication and patterning of multilayered articles comprising perfluorinated elastomers.

Such polymers can reduce or inhibit ions from passing therethrough in a variety of applications, such as implants, since ions that are able to enter may cause the degradation of such articles or devices. For instance, a perfluorinated polymer may be present on at least a portion of the substrate of an article or device. As discussed herein, such perfluorinated polymers may be used, in certain embodiments, to inhibit the passage of ions in various articles or devices, e.g., devices that have been implanted into a subject, or are exposed to physiological conditions, etc. The degradation can be quantified in such polymers, for instance, by determining the specific electrochemical impedance modulus (i.e., the electrochemical impedance modulus, normalized to the geometry of the sample) over long periods of time, e.g., while being exposed to physiological conditions. For instance, in one assay, such polymer films, with a thickness equal or less than 1 μm, can surprisingly retain most (e.g., more than 50%) of their specific electrochemical impedance modulus after being immersed for over 100 days in phosphate buffer solution.

Without wishing to be bound by any theory, it is believed that the hydrophobicity of perfluorinated polymers can make fabrication of articles and devices comprising perfluorinated polymers challenging. Thus, in one embodiment, the present disclosure is directed towards methods of treating a perfluorinated polymer (e.g., a perfluoropolyether) that unexpectedly allows the deposition of additional material bonded to the perfluorinated polymer. The perfluorinated polymer may be treated by applying a plasma (e.g., argon plasma) to the perfluorinated polymer. The additional material, in some cases, is additional perfluorinated polymer that can increase the overall thickness of a perfluorinated polymer layer. Thus, in some embodiments, the fabrication of surprisingly thick perfluorinated polymer layers (e.g., thicker than 300 nanometers) is disclosed. For example, polymer layers thicker than 3 micrometers may be fabricated. This surprising thickness may beneficially improve the stability and/or mechanical properties of perfluorinated polymers in electronics. In contrast, other techniques are not able to produce such thick perfluorinated polymer layers on articles or devices.

In another embodiment, certain properties of perfluorinated polymers are controlled by cross-linking the perfluorinated polymers. This control of properties may beneficially improve the performance of perfluorinated polymers as components of articles and devices, in some embodiments. For example, properties such as electrical properties or a decrease in ion transport may be achieved using certain cross-linked polymers, e.g., as described herein. However, it should be understood that cross-linking is not a requirement in all embodiments.

In some embodiments, the polymer is a fluorinated polymer that is not perfluorinated. For example, the fluorinated polymer may be a partially fluorinated polymer. In some embodiments, the fluorinated polymer is greater than or equal to 25%, greater than or equal to 50%, greater than or equal to 75% or more fluorinated. In some embodiments, the fluorinated polymer is less than or equal to 100%, less than or equal to 90%, less than or equal to 75%, less than or equal to 50%, or less fluorinated. Combinations of these ranges are also possible. For example, in some embodiments the fluorinated polymer is greater than or equal to 25% fluorinated and less than or equal to 100% fluorinated.

The polymer may be any of a variety of suitable fluorinated polymers. For example, in some embodiments the polymer may be poly(1,1,1,3,3,3-hexafluoroisopropyl acrylate) (PHFIPA) or poly[2-(perfluorohexyl)ethyl]acrylate (PPFHEA). The polymer may also be a copolymer (e.g., between two or more fluorinated polymers, including both these polymers and the perfluorinated polymers described above.

In the context of the present disclosure, it has been recognized that fluorinated polymers can be difficult to process, and that this can have negative ramifications for the use of fluorinated polymers. Certain aspects are thus directed towards improved processing of fluorinated polymers, such as perfluorinated polymers. For example, according to some embodiments, fluorinated polymers may be coated and photopatterned onto substrates or other polymer layers, e.g., using added spacers and/or a nitrogen diffusor. In some embodiments, materials can be deposited on top of fluorinated polymers, e.g., by treating the fluorinated polymer, which can facilitate bonding between the fluorinated polymer and subsequently deposited material.

Depositing materials onto fluorinated polymer layers is, in some embodiments, important for fabricating relatively thick and/or multilayered articles comprising fluorinated polymers (e.g., perfluorinated polymers), as discussed herein. In some embodiments, the fluorinated polymers may be treated. For example, some embodiments comprise applying a plasma (e.g., an argon plasma) to the fluorinated polymer to form a treated fluorinated polymer, as is described in further detail below. It has been surprisingly recognized that treatment of the fluorinated polymer may advantageously facilitate deposition of material onto the surface of the fluorinated polymer, in some embodiments.

In particular, the present disclosure is directed towards processing of perfluorinated polymers in certain embodiments. It has been recognized that perfluorinated polymers can be difficult to process, and that this can have negative ramifications for the use of perfluorinated polymers. Certain aspects are thus directed towards improved perfluorinated polymers. For example, according to some embodiments, perfluorinated polymers may be coated onto substrates or other polymer layers, e.g., using added spacers and/or a nitrogen diffusor. In some embodiments, materials can be deposited on top of perfluorinated polymers (e.g., perfluoropolyethers), e.g., by treating the perfluorinated polymer, which can facilitate bonding between the perfluorinated polymer and subsequently deposited material.

Depositing materials onto perfluorinated polymer layers is, in some embodiments, important for fabricating relatively thick and/or multilayered articles comprising perfluorinated polymers, e.g., as discussed herein. In some embodiments, for example, the perfluorinated polymers may be treated. For example, some embodiments comprise applying a plasma (e.g., an argon plasma) to the perfluorinated polymer (e.g., perfluoropolyether) to form a treated perfluorinated polymer (e.g., perfluoropolyether), as is described in further detail below. It has been surprisingly recognized that treatment of the perfluorinated polymer may advantageously facilitate deposition of material onto the surface of the perfluorinated polymer, in some embodiments.

Some embodiments are generally directed to relatively thick and/or multilayered articles that may be resistant to degradation. For example, in certain embodiments, thick and/or multilayered articles may be used for implantable devices. In some cases, such articles may be resistant to degradation by aqueous solutions.

For example, a polymer and/or an article comprising a polymer may be immersed in an aqueous solvent (e.g., saline) for a period of time. Certain polymers and/or articles comprising the polymers as discussed herein are able to retain a high specific electrochemical impedance modulus when immersed in an aqueous solvent, which may be used to demonstrate that the polymer and/or article is able to inhibit, partially or completely, the transport of ions therethrough.

Without wishing to be bound by theory, reduced ion transport in the polymer can result in substantially reduced ionic conductivity through the polymer, reducing degradation and resulting in improved dielectric properties of the polymer, according to certain embodiments. In some embodiments, polymers (e.g. perfluorinated polymers) experience phase transitions at phase transition temperatures. For example, according to certain embodiments, the polymers (e.g. perfluoropolyether) comprise more crystalline phases at lower temperatures. Without wishing to be bound by theory, ion transport may be greater in phases found at temperatures above a phase transition temperature. Certain polymers as discussed herein experience phase-transition temperatures near physiological temperatures (e.g. within +/−1° C., +/−2° C., +/−3° C., or +/−5° C. of 37° C.). The presence of a phase transition near physiological temperatures may, according to certain embodiments, be associated with reduced ion transport through the polymer under physiological conditions.

In some cases, a high specific electrochemical impedance modulus may indicate that the polymer and/or article comprising the polymer will be more stable in vivo. This may be determined, according to certain embodiments, by immersing the polymer and/or the article comprising the polymer in aqueous solution (e.g., phosphate buffer solution) for a period of time; according to some embodiments, the polymer may experience only a small reduction in specific electrochemical impedance modulus, even after being immersed for a long period of time, e.g., at least 100 days, or other times as discussed herein.

For example, according to certain embodiments, the polymer, when formed into an article, exhibits a specific electrochemical impedance modulus of greater than or equal to $1 \times 10^6$ ohm-m, greater than or equal to $2 \times 10^6$ ohm-m, greater than or equal to $3 \times 10^6$ ohm-m, greater than or equal to $5 \times 10^6$ ohm-m, or more after immersion in an aqueous solvent. According to certain embodiments, the polymer, when formed into an article, exhibits a specific electrochemical impedance modulus of greater than or equal to 25%, greater than or equal to 50%, greater than or equal to 75%, greater than or equal to 90%, greater than or equal to 95%, or greater than or equal to 99% or more of its original specific electrochemical impedance modulus after immersion in an aqueous solvent. In other words, an article comprising a polymer may exhibit a small reduction in specific electrochemical impedance modulus, even after immersion in an aqueous solvent for a period of time, which may demonstrate that the polymer and/or article is able to inhibit ion transport. For example, according to certain embodiments, an article comprising a polymer may exhibit a reduction in specific electrochemical impedance modulus of less than or equal to 75%, less than or equal to 50%, less than or equal to 25%, less than or equal to 10%, less than or equal to 5%, less than or equal to 1%, etc. of its original specific electrochemical impedance modulus after immersion in an aqueous solvent for a period of time, e.g., at least 100 days, or other times as discussed herein.

Generally, electrical impedance may be expressed as a complex quantity, as is known by those of ordinary skill in the art. For instance, the electrochemical impedance may be described as having an electrochemical impedance modulus (a magnitude of electrical impedance) and a phase (a phase angle of the complex quantity). The electrochemical impedance modulus is geometry dependent and can be normalized by sample geometry to produce the specific electrochemical impedance modulus. For example, in embodiments comprising a homogeneous polymer with an area and a thickness, the specific electrochemical impedance modulus of the homogeneous polymer is the electrochemical impedance modulus of the homogeneous polymer, multiplied by the area of the polymer and divided by the thickness of the polymer. Normalization can allow comparisons between samples of different geometry. According to certain embodiments, the area of the polymer is known. For example, in certain embodiments the area of the polymer used to calculate specific electrochemical impedance modulus may equal the area of a conductive material disposed beneath the polymer. The thickness of the polymer may be determined by any suitable technique, including, for example, the use of a stylus profiler, a scanning electron microscope, an atomic force microscope, or an X-ray reflectometer.

Figure 2:
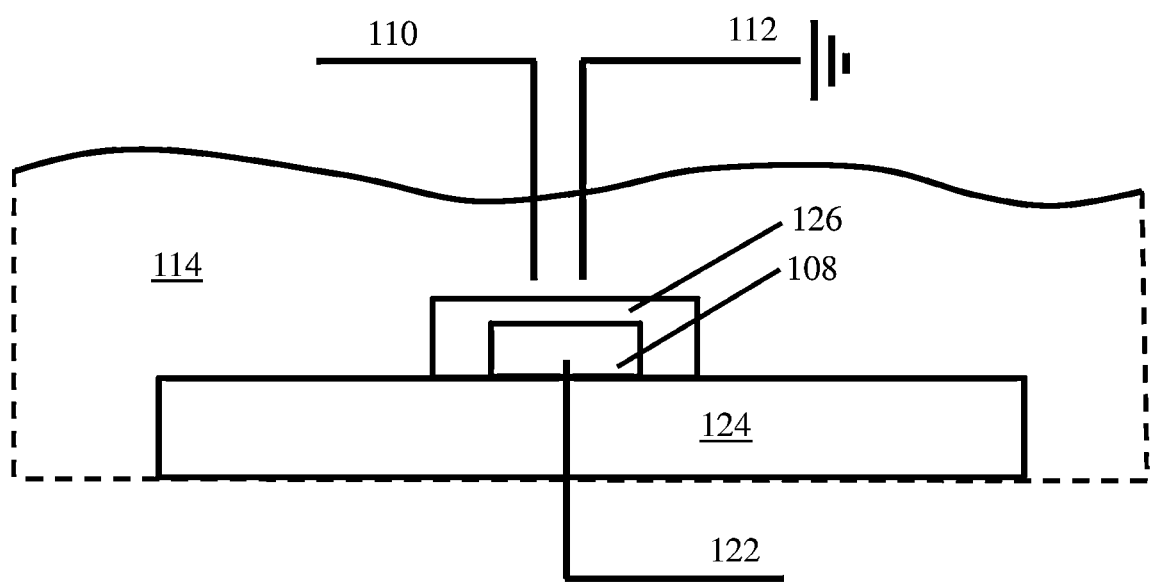
FIG. 2 presents a cross-sectional schematic illustration of an experimental setup for measuring impedance, according to certain embodiments.

The electrochemical impedance is typically measured at a frequency. For example, in some embodiments, electrochemical impedance is measured at 1 kHz, 2 kHz, 5 kHz, or 10 kHz. Electrochemical impedance may be measured by any suitable technique. For example, a person of ordinary skill in the art would know that electrochemical impedance may be measured using a standard three electrode set-up, as illustrated in FIG. 2. An exemplary procedure for measuring electrical impedance is described in Example 2, below.

According to certain embodiments, the aqueous solvent comprises phosphate buffer solution. In some embodiments, the phosphate buffer solution (PBS) has a concentration of greater than or equal to 0.5×, 1×, 2×, 3×, 5×, 8×, or 10× the standard concentration of PBS (0.1 M). In some embodiments, the phosphate buffer solution (PBS) has a concentration of less than or equal to 15×, 12×, 10×, 8×, 5×, or 3× the standard concentration of PBS (0.1 M). Herein, a solution of phosphate buffer solution that is 10× the standard concentration of PBS is denoted 10× phosphate buffer solution or 10×PBS. Combinations of these ranges are possible. For example, according to certain embodiments, the phosphate buffer solution has a concentration of greater than or equal to 0.5× and less than or equal to 15×. According to certain embodiments, the aqueous solution is 1×PBS. In some embodiments, the aqueous solution is 10×PBS.

In some embodiments, immersion occurs at a temperature. According to certain embodiments, the temperature of immersion is greater than or equal to 20° C., greater than or equal to 25° C., greater than or equal to 30° C., greater than or equal to 35° C., greater than or equal to 37° C., greater than or equal to 40° C., greater than or equal to 45° C., greater than or equal to 50° C., greater than or equal to 60° C., greater than or equal to 70° C., or greater. According to certain embodiments, the temperature of immersion is less than or equal to 90° C., less than or equal to 80° C., less than or equal to 70° C., less than or equal to 60° C., less than or equal to 50° C., less than or equal to 40° C., less than or equal to 37° C., or less. Combinations of these ranges are possible. For example, according to certain embodiments the temperature of immersion is greater than or equal to 20° C. and less than or equal to 90° C.

The polymer may, according to some embodiments, experience a small reduction in specific electrochemical impedance modulus after being immersed in an aqueous solvent for a period of time, e.g., a reduction of less than 5%, or other reductions such as described herein. For example, the polymer may experience a small reduction in specific electrochemical impedance modulus after being immersed for greater than or equal to 5 days, greater than or equal to 6 days, greater than or equal to 7 days, greater than or equal to 8 days, greater than or equal to 9 days, greater than or equal to 10 days, greater than or equal to 15 days, greater than or equal to 25 days, greater than or equal to 50 days, greater than or equal to 100 days, greater than or equal to 150 days, greater than or equal to 200 days, greater than or equal to 250 days, greater than or equal to 300 days, greater than or equal to 350 days, greater than or equal to 400 days, greater than article 450 days, greater than or equal to 500 days, or longer. Combinations of these ranges with previously stated ranges are possible. For example, according to some embodiments, the polymer exhibits a reduction in specific electrochemical impedance modulus at 1 kHz of less than or equal to 50% after being immersed for greater than or equal to 100 days in phosphate buffer solution. As another example, according to certain embodiments, the polymer exhibits a reduction in specific electrochemical impedance modulus at 1 kHz of no more than 50% after being immersed for 450 days in phosphate buffer solution. As yet another example, according to certain embodiments, the polymer exhibits a reduction in specific electrochemical impedance modulus at 1 kHz of no more than 50% after being immersed for 5 days in 10× phosphate buffer solution at 70° C.

The polymer may, according to some embodiments, experience a small reduction in specific electrochemical impedance modulus after being immersed in an aqueous solvent for a period of time related to an average thickness H (in microns) of the polymer within an article. For example, in some embodiments, the polymer experiences a small reduction in specific electrochemical impedance modulus after being immersed in an aqueous solvent for greater than or equal to $1*H^2$ days, greater than or equal to $2*H^2$ days, greater than or equal to $3*H^2$ days, greater than or equal to $4*H^2$ days, greater than or equal to $5*H^2$ days, greater than or equal to $10*H^2$ days, or greater. In some embodiments, the polymer experiences a small reduction in specific electrochemical impedance modulus after being immersed in an aqueous solvent of less than or equal to $100*H^2$ days, less than or equal to $50*H^2$ days, less than or equal to $20*H^2$ days, less than or equal to $10*H^2$ days, or less. Combinations of these ranges are possible. For example, in some embodiments, the polymer experiences a small reduction in specific electrochemical impedance modulus after being immersed in an aqueous solvent of greater than or equal to $2*H^2$ days and less than or equal to $100*H^2$ days. Combinations of these ranges with the preceding ranges are also possible. For example, according to some embodiments, the polymer exhibits a reduction in specific electrochemical impedance modulus at 1 kHz of less than or equal to 50% after being immersed for greater than or equal to $1*H^2$ days in 10× phosphate buffer solution at 65° C.

A polymer's resistance to degradation may, according to certain embodiments, be related to the cross-linking of the polymer. Any suitable cross-linking chemistry may be present within the polymer. Thus, the polymer (e.g., the perfluoropolyether) may, according to certain embodiments, comprise a cross-linker. For example, in accordance with one set of embodiments, perfluoropolyether dimethylacrylate (PFPE-DMA) comprises two methylacrylate species, each of which can undergo a cross-linking reaction, according to certain embodiments. Thus, for example, perfluoropolyether dimethylacrylate (PFPE-DMA) may be cross-linked via free-radical polymerization of the methylacrylate species of the PFPE-DMA, resulting in the formation of a cross-linked network comprising a perfluorinated polymer in some embodiments.

In some embodiments, perfluorinated polymers with a higher degree of cross-linking are more resistant to degradation. Such resistance to degradation can be determined, for example, by exposing the perfluorinated polymer to a solvent, such as a fluorinated solvent. The degree of cross-linking may be measured by any suitable method. In some cases, the degree of cross-linking can be measured directly, e.g., by spectroscopically detecting a concentration of cross-links of the polymer. In other embodiments, the degree of cross-linking may be determined indirectly. For example, in some cases, the degree of cross-linking may be determined by determining the degradation of the polymer in a solvent capable of dissolving the polymer when it is not cross-linked. Generally, polymers that are more heavily cross-linked are less soluble in a given solvent than polymers that are less heavily cross-linked.

According to certain embodiments, a cross-linked polymer will experience very little degradation, when immersed in a solvent capable of dissolving the polymer when it is not cross-linked. Any solvent capable of dissolving the polymer when it is not cross-linked may be used to determine the degree of cross-linking of the polymer. According to certain embodiments, a fluorinated solvent may be used to determine the cross-linking of a fluorinated polymer. For example, according to certain embodiments, a fluorinated solvent may be used to determine the cross-linking of a perfluorinated polymer (e.g., a perfluoropolyether). In some embodiments, 1,3-bis(trifluoromethyl)benzene is a suitable solvent to determine the degree of cross-linking of the polymer.

In some embodiments, the fluorinated polymer has a high specific electrochemical impedance modulus, as previously described (e.g., a specific electrochemical impedance modulus of at least $10^6$ ohm-m), even after being immersed in a solvent as described above. Similarly, in some embodiments, the fluorinated polymer may have a low reduction in specific electrochemical impedance modulus, as previously described (e.g., a reduction in specific electrochemical impedance modulus of less than or equal to 50%), after being immersed in a solvent.

In addition, in some embodiments, the perfluorinated polymer has a high specific electrochemical impedance modulus, as previously described (e.g., a specific electrochemical impedance modulus of at least $10^6$ ohm-m), even after being immersed in a solvent as described above. Similarly, in some embodiments, the perfluorinated polymer may have a low reduction in specific electrochemical impedance modulus, as previously described (e.g., a reduction in specific electrochemical impedance modulus of less than or equal to 50%), after being immersed in a solvent.

According to some embodiments, the cross-linking of the polymer may be determined by measuring the specific electrochemical impedance modulus of the polymer after exposing the polymer to the solvent capable of dissolving the polymer when it is not cross-linked. For example, in some embodiments, more heavily cross-linked polymers retain exhibit a high specific electrochemical impedance modulus when first formed into an article and subsequently immersed in a fluorinated solvent (e.g., 1,3-bis(trifluoromethyl)benzene) for a period of time.

According to certain embodiments, the period of time during which the polymer is immersed in the solvent capable of dissolving the un-cross-linked polymer is greater than or equal to 5 seconds, greater than or equal to 6 seconds, greater than or equal to 7 seconds, greater than or equal to 8 seconds, greater than or equal to 9 seconds, greater than or equal to 10 seconds, greater than or equal to 15 seconds, greater than or equal to seconds, greater than or equal to 30 seconds, greater than or equal to 45 seconds, greater than or equal to 60 seconds, greater than or equal to 90 seconds, or more.

In order to measure the specific electrochemical impedance modulus of the polymer after immersing the polymer in the solvent capable of dissolving the polymer when it is not cross-linked, the polymer is first dried according to certain embodiments. The polymer may be dried by any suitable method. For example, the polymer may be dried in nitrogen, dried in air, or dried in vacuum.

Combinations of impedance frequencies measurement, reductions in specific electrochemical impedance modulus and/or values of specific electrochemical impedance modulus, polymer thicknesses, times of polymer immersion, drying methods, and solvents capable of dissolving the polymer when it is not cross-linked are also possible. For example, according to certain embodiments the polymer, when formed into an article having a minimum dimension of at least 0.3 micrometers that is immersed in 1,3-bis(trifluoromethyl)benzene for a period of greater than or equal to 9 seconds, dried in nitrogen, and measured at 1 kHz, exhibits a specific electrochemical impedance modulus of at least $10^6$ ohm-m. As another example, according to certain embodiments the polymer, when formed into an article having a minimum dimension of at least 0.3 micrometers and a minimum dimension of less than or equal to 3.0 micrometers that is immersed in 1,3-bis(trifluoromethyl)benzene for a period of greater than or equal to 30 seconds, dried in nitrogen, and measured at 1 kHz, exhibits a specific electrochemical impedance modulus of at least $10^6$ ohm-m.

In some embodiments, the polymer has a molecular weight prior to cross-linking (e.g., a weight average molecular weight) that, according to certain embodiments, is less than or equal to 1000 kDa, 500 kDa, 200 kDa, 100 kDa, 50 kDa, 40 kDa, 30 kDa, 20 kDa, 15 kDa, 10 kDa, 8 kDa, 5 kDa, or less. The weight average molecular weight of the polymer, according to certain embodiments, is greater than or equal to 1 kDa, 2 kDa, 3 kDa, 4 kDa, 5 kDa, 8 kDa, 10 kDa, 15 kDa, 20 kDa, 30 kDa, 40 kDa, or greater. Combinations of these ranges are possible. For instance, the weight average molecular weight of the polymer may be greater than or equal to 1 kDa and less than or equal to 8 kDa, according to certain embodiments. According to other embodiments, the weight average molecular weight of the polymer may be greater than 20 kDa. The weight average molecular weight of the polymer may be determined by any suitable method, e.g., by gel permeation chromatography.

According to certain embodiments, the polymer may be an elastomer. For instance, in some embodiments, the polymer may exhibit a low elastic modulus. For example, the polymer has an elastic modulus below 10 MPa, below 5

MPa, below 2 MPa, below 1 MPa, or lower, according to certain embodiments. In some embodiments, the polymer can exhibit a high elastic tensile deformation. For example, in some embodiments, the polymer can exhibit elastic tensile deformation at or above 20% strain, 30% strain, 50% strain, or 100% strain. In some embodiments, combinations of these mechanical properties are possible. For example, in some embodiments, the polymer has an elastic modulus below 1 MPa and can exhibit elastic tensile deformation at or above 20% strain. The elastic modulus and/or the elastic tensile deformation may be determined by any suitable method. For example, the elastic modulus and the elastic tensile deformation could be measured using a tensile tester.

Some aspects are directed towards methods for preparing articles comprising fluorinated polymers. In some embodiments, a fluorinated polymer is deposited on a substrate. Certain aspects are directed towards methods for preparing articles comprising perfluorinated polymers. In some embodiments, a perfluorinated polymer (e.g., a perfluoropolyether) is deposited on a substrate. The substrate may, according to certain embodiments, provide mechanical support for the article. In some embodiments, the substrate may functionally interact with the article, e.g., if the article overlaps a portion of a circuit of the substrate.

The substrate may comprise any suitable material. For example, the substrate may be a semiconductor substrate. The semiconductor may comprise any suitable material. According to certain embodiments, the substrate may comprise silicon, germanium, gallium arsenide, or combinations thereof. Other substrates, e.g., comprising semiconductors, are also possible.

In certain embodiments, the substrate is coated. In some embodiments, the coating of the substrate may act as a release layer. A release layer is a layer that can facilitate the separation of an article from a substrate, e.g., via its degradation. In some embodiments, spacers are added to the substrate. The spacers may comprise, for example, photoresist. According to certain embodiments, the addition of spacers to the substrate may advantageously protect the article. For example, spacers of the substrate are, according to certain embodiments, used to protect the article from contact with a mask (e.g. a photoaligner mask), or from contact with a nitrogen diffuser.

For example, in some embodiments the substrate is coated with a photoresist. Examples of photoresists include epoxy-based photoresists, such as mixtures of bisphenol A Novolac epoxy and triarylsulfinium/hexafluoroantimonate salts (SU-8 photoresists), and mixtures of diazonapthoquinone (DNQ) and phenol formaldehyde resins (DNQ-Novolacs). In certain embodiments, the substrate is coated with metal (e.g., nickel).

A polymer may be treated using a plasma. For example, in some embodiments, a plasma is applied to a fluorinated polymer to for a treated fluorinated polymer. In some embodiments, a plasma is applied to the perfluorinated polymer to form a treated perfluorinated polymer. Any suitable plasma may be used. According to certain embodiments, the plasma is or comprises atoms that form inert gases. For example, according to certain embodiments, the plasma comprises nitrogen. According to certain embodiments, the plasma comprises argon. Treatment of the fluorinated polymer may advantageously prepare a surface of the fluorinated polymer for interaction with external materials. For example, treatment of the fluorinated polymer may introduce reactive, charged, and/or polarized sites on the surface of the fluorinated polymer, which can form chemical or physical bonds with subsequently deposited materials, according to certain embodiments. In some embodiments, treatment of the perfluorinated polymer advantageously prepares the surface of the perfluorinated polymer for interaction with external materials. For example, treatment of the perfluorinated polymer may introduce reactive, charged, and/or polarized sites on the surface of the perfluorinated polymer, which can form chemical or physical bonds with subsequently deposited materials, according to certain embodiments.

The treatment of the perfluorinated polymer using plasma formed from an inert gas can, in some embodiments, advantageously exclude oxygen from the treated perfluorinated polymer. This may prevent the reaction of oxygen with the treated surface, advantageously enhancing the ability of the perfluorinated polymer to adhere to other materials. More generally, a fluorinated polymer may be treated in some embodiments in a way that, advantageously, excludes oxygen from the treated fluorinated polymer. This may prevent the reaction of oxygen with the treated surface, advantageously enhancing the ability of the fluorinated polymer to adhere to other materials. As a result, arbitrarily thick and/or multilayered articles comprising perfluorinated polymers may be fabricated in certain embodiments. Similarly, arbitrarily thick and/or multilayered articles comprising fluorinated polymers may be fabricated, in some embodiments. Fabrication of multilayered articles comprising fluorinated polymers may provide a substantial advantage for the preparation of articles comprising a high number density of electrodes. For example, as described in greater detail elsewhere herein, fabricating additional rows of electrodes on a sensor may comprise fabricating additional layers of a device.

After the formation of the treated fluorinated polymer, additional material may be deposited onto the treated fluorinated polymer. In some embodiments, after the formation of the treated perfluorinated polymer (e.g., perfluoropolyether), additional material is deposited onto the treated perfluorinated polymer. The deposited additional material may be a conductive material, or other materials. For example, in some embodiments, the deposited additional material may comprise a metal or metal alloy. The ability to deposit a conductive material is advantageous, according to certain embodiments, because it can be used to fabricate portions of electronic circuits (e.g., sensors). For example, conductive materials may be used to fabricate electrodes.

In some embodiments, the additional material is a polymer. In certain embodiments, the polymer is not a perfluorinated polymer. In some embodiments, the additional material is not a fluorinated polymer. In certain embodiments, the additional material is a photoresist.

According to certain embodiments, polymers may be deposited onto treated perfluorinated polymers via solution processing. More generally, polymers may deposited onto treated fluorinated polymers via solution processing. Due to the hydrophobic nature of the perfluorinated polymers, according to some embodiments, the perfluorinated polymer does not swell in the presence of non-fluorinated solvents. Similarly, in some embodiments fluorinated polymers may not swell in the presence of non-fluorinated solvents, owing to their hydrophobicity. Fluorinated polymers may experience a low volumetric swelling during solution processing of additional materials. The perfluorinated polymer may experience a volumetric swelling of less than or equal to 5%, less than or equal to 2%, less than or equal to 1%, less than or equal to 0.5%, less than or equal to 0.2%, or less, in some embodiments. For example, the perfluorinated polymer may experience a volumetric swelling of less than or equal to 5%, less than or equal to 2%, less than or equal to 1%, less than or equal to 0.5%, less than or equal to 0.2%, or less. According to certain embodiments, the low volumetric swelling of the perfluorinated polymer may advantageously preserve a pattern with a high lateral resolution, which nonetheless comprises multiple layers of chemically distinct polymers. More generally, fluorinated polymers may, advantageously, preserve a pattern with a high lateral resolution, which nonetheless comprises multiple layers of chemically distinct polymers as a result of their low volumetric swelling.

The deposited additional material may be additional fluorinated polymer (e.g., an additional layer of a fluorinated polymer). This may result in a thicker layer of the fluorinated polymer. In some embodiments, the fluorinated polymer layer, has a minimum dimension of at least 0.3 micrometers, at least 0.5 micrometers, at least 0.7 micrometers, or more exhibits a high degree of cross-linking. In some embodiments, the fluorinated polymer layer has a minimum dimension of less than or equal to 3 micrometers, less than or equal to 2.5 micrometers, less than or equal to 2 micrometers, less than or equal to 1 micrometer. Combinations of these ranges are possible. For example, according to certain embodiments, the fluorinated polymer layer has a minimum dimension of at least 0.3 micrometers and less than or equal to 3 micrometers.

In some embodiments, the deposited additional material is an additional layer of perfluorinated polymer. In certain embodiments, depositing an additional layer of the perfluorinated polymer may result in a thicker layer of the perfluorinated polymer. In some embodiments, the perfluorinated polymer layer, has a minimum dimension of at least 0.3 micrometers, at least 0.5 micrometers, at least 0.7 micrometers, or more exhibits a high degree of cross-linking. In some embodiments, the perfluorinated polymer layer has a minimum dimension of less than or equal to 3 micrometers, less than or equal to 2.5 micrometers, less than or equal to 2 micrometers, less than or equal to 1 micrometers. Combinations of these ranges are possible. For example, according to certain embodiments, the perfluorinated polymer layer has a minimum dimension of at least 0.3 micrometers and less than or equal to 3 micrometers.

Figure 3:
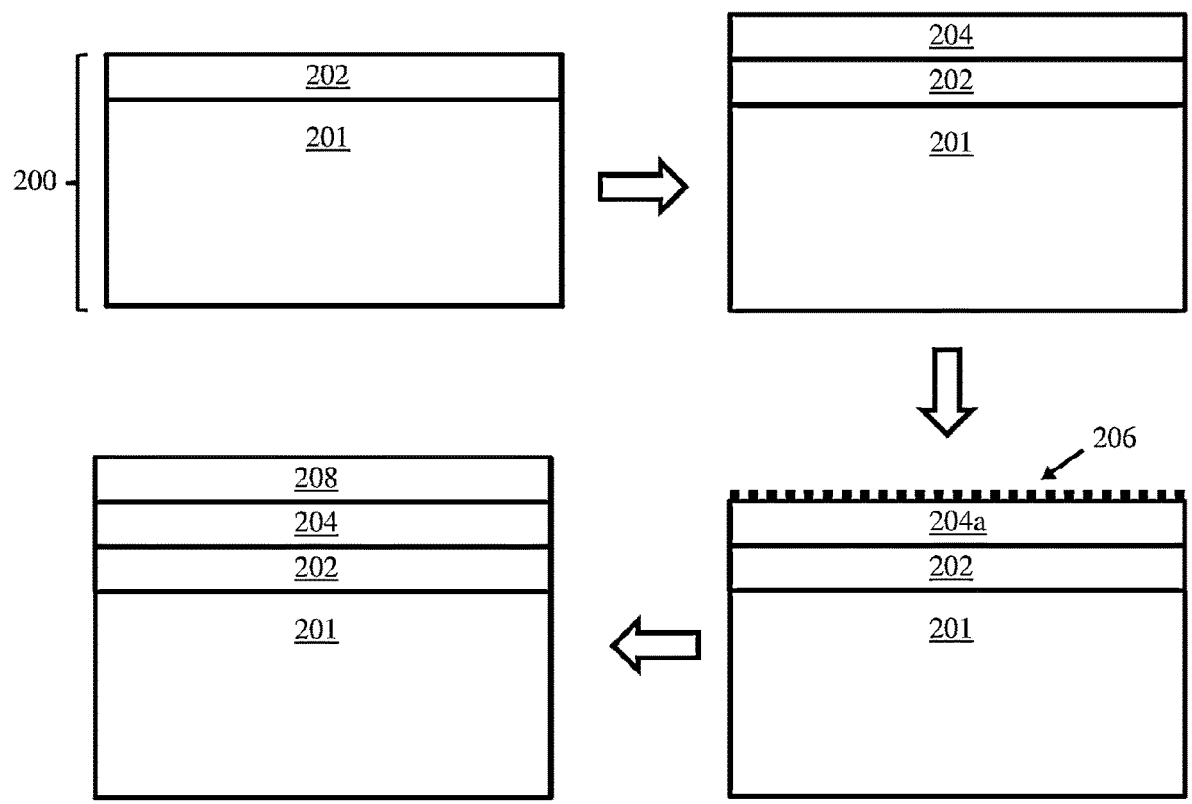
FIG. 3 presents a method of preparing an article comprising a perfluorinated polymer, according to certain embodiments.

FIG. 3 presents an exemplary representation of a method. First, perfluorinated polymer 204 is deposited on substrate 200, which comprises semiconductor 201 coated with release layer 202. Next, plasma is applied to perfluorinated polymer 204 to form treated perfluorinated polymer 206. After the formation of treated perfluorinated polymer layer 204a, material 208 is deposited onto treated perfluorinated polymer layer 204a. It should, of course, be understood that the same method could be performed for any of a variety of fluorinated polymers as described above, and is not limited to perfluorinated polymers, in particular.

In addition, certain aspects of the present disclosure are directed to articles formed from methods such as those described herein. According to one aspect, for instance, an article may comprise one or more layers, e.g., formed as described above. For example, in some embodiments, the article comprises a first layer, a second layer, and a third layer. According to certain embodiments, the first layer comprises a polymer. The first layer may comprise a fluorinated polymer. For example, the first layer may comprise a perfluorinated polymer (e.g., perfluoropolyether). In some embodiments, the second layer is bonded to the first layer. In some embodiments, the third layer is bonded to the second layer. The third layer may comprise a fluorinated polymer. Layers that are bonded may be directly bonded, or they may be separated by one or more intervening layers that connect them.

In one aspect, the present disclosure is directed towards articles comprising perfluorinated polymers (e.g., perfluoropolyether). In some embodiments, the article comprises a first layer comprising a perfluorinated polymer (e.g., a perfluoropolyether). According to certain embodiments, the article comprises a second layer, bonded to the first layer. In some embodiments, the article comprises a third layer, bonded to the second layer, and comprising a perfluorinated polymer (e.g., perfluoropolyether). According to certain embodiments, the article comprises one or more additional layers (e.g., on top of the third layer). These can be formed, e.g., as discussed herein.

In another aspect, the present disclosure is directed towards articles comprising fluorinated polymers. In some embodiments, the article comprises a first layer comprising a fluorinated polymer. According to certain embodiments, the article comprises a second layer, bonded to the first layer. In some embodiments, the article comprises a third layer, bonded to the second layer, and comprising a fluorinated polymer. According to certain embodiments, the article comprises one or more additional layers (e.g., on top of the third layer). These can be formed, e.g., as discussed herein.

Some embodiments may further comprise one or more additional layers. For example, embodiments may contain additional layers to facilitate adhesion between the first, second, and/or third layers; layers to modify dielectric properties of the article; sensing layers; and/or layers to insulate (e.g., electrically insulate, thermally insulate, chemically insulate, etc.) the article. The one or more additional layers may include intervening layers, such as layers between the first layer and the second layer, and/or they may be external layers, such as layers deposited on top of the third layer.

According to certain embodiments, the first layer has a thickness of greater than or equal to 50 nanometers, greater than or equal to 100 nanometers, greater than or equal to 200 nanometers, greater than or equal to 300 nanometers, greater than or equal to 400 nanometers, greater than or equal to 500 nanometers, or greater. According to certain embodiments, the first layer has a thickness of less than or equal to 5000 nanometers, less than or equal to 4000 nanometers, less than or equal to 3000 nanometers, less than or equal to 2000 nanometers, less than or equal to 1000 nanometers, less than or equal to 500 nanometers, or less. Combinations of these ranges are possible. For example, according to certain embodiments the first layer has a thickness of greater than or equal to 50 nanometers and less than or equal to 5000 nanometers. As another example, according to some embodiments, the first layer has a thickness of greater than or equal to 300 nanometers and less than or equal to 2000 nanometers.

According to certain embodiments, the second layer has a thickness of greater than or equal to 50 nanometers, greater than or equal to 100 nanometers, greater than or equal to 200 nanometers, greater than or equal to 300 nanometers, greater than or equal to 400 nanometers, greater than or equal to 500 nanometers, or greater. According to certain embodiments, the second layer has a thickness of less than or equal to 5000 nanometers, less than or equal to 4000 nanometers, less than or equal to 3000 nanometers, less than or equal to 2000 nanometers, less than or equal to 1000 nanometers, less than or equal to 500 nanometers, or less. Combinations of these ranges are possible. For example, according to certain embodiments the second layer has a thickness of greater than or equal to 50 nanometers and less than or equal to 5000 nanometers. As another example, according to some embodiments, the second layer has a thickness of greater than or equal to 300 nanometers and less than or equal to 2000 nanometers.

According to certain embodiments, the third layer has a thickness of greater than or equal to 50 nanometers, greater than or equal to 100 nanometers, greater than or equal to 200 nanometers, greater than or equal to 300 nanometers, greater than or equal to 400 nanometers, greater than or equal to 500 nanometers, or greater. According to certain embodiments, the third layer has a thickness of less than or equal to 5000 nanometers, less than or equal to 4000 nanometers, less than or equal to 3000 nanometers, less than or equal to 2000 nanometers, less than or equal to 1000 nanometers, less than or equal to 500 nanometers, or less. Combinations of these ranges are possible. For example, according to certain embodiments the third layer has a thickness of greater than or equal to 50 nanometers and less than or equal to 5000 nanometers. As another example, according to some embodiments, the third layer has a thickness of greater than or equal to 300 nanometers and less than or equal to 2000 nanometers.

According to certain embodiments, the second layer overlaps greater than or equal to 5%, greater than or equal to 10%, greater than or equal to 25%, greater than or equal to 50%, greater than or equal to 75%, greater than or equal to 90%, greater than or equal to 95%, greater than or equal to 99%, or more of the surface area of the first layer. According to certain embodiments, the second layer overlaps less than or equal to 100%, less than or equal to 95%, less than or equal to 90%, less than or equal to 75%, less than or equal to 50%, less than or equal to 25%, or less of the surface area of the first layer. Combinations of these ranges are possible. For example, according to certain embodiments the second layer overlaps greater than or equal to 5% and less than or equal to 100% of the surface area of the first layer.

According to certain embodiments, the second layer overlaps greater than or equal to 5%, greater than or equal to 10%, greater than or equal to 25%, greater than or equal to 50%, greater than or equal to 75%, greater than or equal to 90%, greater than or equal to 95%, greater than or equal to 99%, or more of the surface area of the third layer. According to certain embodiments, the second layer overlaps less than or equal to 100%, less than or equal to 95%, less than or equal to 90%, less than or equal to 75%, less than or equal to 50%, less than or equal to 25%, or less of the surface area of the third layer. Combinations of these ranges are possible. For example, according to certain embodiments the second layer overlaps greater than or equal to 5% and less than or equal to 100% of the surface area of the third layer.

In some embodiments, two layers may be considered to overlap in a region if a ray orthogonal to the surface of, and pointing away from, one layer would extend through the other layer. Overlapping layers need not directly contact each other. They may directly contact each other, or they may be separated (e.g., by one or more intervening layers). In addition, it should be understood that although in various embodiments, one or more (or all) of the layers may be substantially planar and/or rectangular, this is not necessarily a requirement.

According to certain embodiments, portions of the second layer do not overlap with the first layer and/or the third layer. For example, according to certain embodiments, a portion of the second layer is exposed (e.g., to form an electrode). According to some embodiments, a portion of the second layer is covered by a polymer that is not fluorinated. For example, according to certain embodiments, a portion of the second layer (e.g., an electrode) may be covered by a layer of conductive polymer (e.g., PEDOT:PSS).

While articles described herein may comprise at least 3 layers, in some embodiments, the articles describe herein may comprise one or a plurality of layers. For example, an article described herein may comprise 1, 2, 3, 4, 5, 8, 10, 15, 20, 25, or more layers. In some embodiments, an article described herein may comprise less than or equal to 100, less than or equal to 50, less than or equal to 25, or fewer articles. Combinations of these ranges are also possible. For instance, an article described herein may comprise greater than or equal to 1 layer and less than or equal to 100 layers. In some embodiments, the article comprises a plurality of polymer layers (e.g., fluorinated polymer layers). As one example, the article may comprise alternating conductive layers and polymer layers.

In some embodiments, an article comprises a conducting layer adjacent to a plurality of layers of an article (e.g., adjacent to fluorinated polymer layers of an article). For example, in some embodiments, the article comprises an electrode. The electrode may be a surface electrode of the article. The article may comprise a plurality of electrodes (e.g., a plurality of surface electrodes). In some embodiments, the article comprises a substrate (e.g., a substrate designed to be implanted in a subject). The substrate may comprise the plurality of the electrodes. According to some embodiments, the electrodes may be formed on the article by depositing a material onto a treated fluorinated polymer of the article, as described above. For example, an electrode may be formed by depositing a metal layer on top of a treated fluorinated polymer layer, as described above. In some embodiments, the electrodes may be electrically connected to conductive layers of an article. For example, an electrode may contact a metal layer of an article, such that the electrode can be electrically connected to an external circuit.

An article may be used to determine electrical activity using a plurality of electrodes on a substrate of the article at least partially contained within a subject. In some embodiments, the electrode may be used to determine electrical activity. For example, a plurality of electrodes may be used to determine electrical activity. The electrical activity may be neural activity. For example, the electrode may be used to determine electrical activity of a single cell within a subject (e.g., a living subject). For example, the cell may be a neuron. The electrode may be configured to contact the cell for a period of time. For example, in some embodiments, the electrode is configured to contact the cell for a period of greater than or equal to 1 days, greater than or equal to 5 days, greater than or equal to 7 days, greater than or equal to 14 days, greater than or equal to 3 weeks, greater than or equal to 4 weeks, or greater. In some embodiments, the electrode is configured to contact the cell for a period of less than or equal to 6 months, less than or equal to 3 months, less than or equal to 6 weeks, less than or equal to 5 weeks, less than or equal to 4 weeks, less than or equal to 14 days, or less. Combinations of these ranges are possible. For example, in some embodiments, the electrode is configured to contact the cell for a period of greater than or equal to 1 day and less than or equal to 6 months. In some embodiments, the electrode is configured to continuously monitor electrical activity from the vicinity of the cell over the period of time (e.g., for a period of at least 5 days). In some embodiments, the electrode is configured to intermittently monitor electrical activity from the vicinity of the cell over the period of time.

In some embodiments, the electrode may be used to electrically stimulate cells. For example, a plurality of electrodes may be used to stimulate cells. The electrode may be used to stimulate neural activity. For example, the electrode may be used to stimulate electrical activity of neurons of subject (e.g., a living subject). In some embodiments, the electrode may be used to stimulate neurons in the vicinity of the brain probe.

An article may comprise electrodes having an electrode number density. The electrode number density may be an area-density of electrodes situated on an implanted portion of the article (e.g., the substrate of the article). In some embodiments, the electrodes have an electrode number density of greater than or equal to $10^{-5}$ electrodes/micron$^2$, greater than or equal to $10^{-4}$ electrodes/micron$^2$, greater than or equal to $10^{-3}$ electrodes/micron$^2$, greater than or equal to $10^{-2}$ electrodes/micron$^2$, greater than or equal to $10^{-1}$ electrodes/micron$^2$, or greater. In some embodiments, the electrodes have an electrode number density of less than or equal to $10^1$ electrodes/micron$^2$, less than or equal to $10^0$ electrodes/micron$^2$, less than or equal to $10^{-1}$ electrodes/micron$^2$, or less. Combinations of these ranges are possible. For example, in some embodiments, the electrodes have an electrode number density of greater than or equal to $10^{-5}$ electrodes/micron$^2$ and less than or equal to $10^1$ electrodes/micron$^2$.

In some embodiments, the article may be patterned (e.g., by a mask), as is described in more detail below. The article may have a resolution (e.g., a spatial resolution). In some cases, the resolution may be determined as a lateral resolution. One advantage of certain articles described herein is their high lateral resolution. For example, in some embodiments an article has a lateral resolution at or below 30 micrometers, at or below 20 micrometers, at or below 10 micrometers, at or below 5 micrometers at or below 2 micrometers, or below. The lateral resolution of the structure may be determined by any suitable technique, e.g., by scanning electron microscopy.

In some embodiments, the article is on a substrate (e.g., a semiconductor substrate). In some embodiments, the article is not on the substrate, e.g., because it has been separated from the substrate. According to certain embodiments, the substrate comprises (e.g., is coated with) a release layer as described above. In some embodiments, preparing an article on a substrate comprising a release layer may facilitate separation of the article from the photoresist.

The perfluoropolyether may have any suitable molecular weight. According to certain embodiments, it may be advantageous for the perfluorinated polymer (e.g., perfluoropolyether) to have a low molecular weight (e.g., a weight average molecular weight of less than 8 kDa, or other molecular weights such as those described herein). The low molecular weight of the perfluorinated polymer, in some embodiments, may ensure that the perfluoropolyether remains rigid when it is cross-linked on a substrate, resulting in rigid perfluoropolyether.

According to certain embodiments, it may be advantageous for a perfluorinated polymer to have a high molecular weight (e.g., a weight average molecular weight of greater than or equal to 20 kDa). The high molecular weight of the perfluorinated polymer may, according to certain embodiments, provide the perfluorinated polymer with advantageous physical properties for sensing applications. For example, according to certain embodiments, the high molecular weight of the perfluorinated polymer may mean that the perfluorinated polymer is an elastomer.

In some embodiments, the second layer comprises a conductive material. This may be advantageous in certain embodiments, e.g., when the article is a part of a device as described below, since it allows the article to be electronically connected to a device. This can also allow the article to act as a sensor for such a device, according to certain embodiments, since an electrical signal received by a portion of the article can be conducted through the article to the device. In some embodiments, the second layer comprises a metal or metal alloy, such as aluminum, silver, copper, gold, etc. The second layer may be deposited by any suitable method. For example, the second layer may be deposited by vapor deposition (e.g., physical vapor deposition, chemical vapor deposition). According to certain embodiments, the second layer may be electronically connected to an electrode (e.g., a working electrode).

Articles described herein may have suitable mechanical properties. For example, in some embodiments the electrode has an overall elastic modulus of greater than or equal to $10^3$ Pa, greater than or equal to $10^4$ Pa, greater than or equal to $10^5$ Pa, greater than or equal to $10^6$ Pa, or greater. In some embodiments, the electrode has an overall elastic modulus of less than or equal to $10^9$ Pa, less than or equal to $10^8$ Pa, less than or equal to $10^7$ Pa, less than or equal to $10^6$ Pa, or less. Combinations of these ranges are possible. For example, in some embodiments, electrode has an overall elastic modulus of greater than or equal to $10^3$ Pa and less than or equal to $10^9$ Pa.

In some embodiments an article comprises a substrate having a ratio of a number density of electrodes to an overall elastic modulus of greater than or equal to $10^{-11}$ electrodes/micron$^2$-Pa, greater than or equal to $10^{-10}$ electrodes/micron$^2$-Pa, greater than or equal to $10^{-9}$ electrodes/micron$^2$-Pa, greater than or equal to $10^{-8}$ electrodes/micron$^2$-Pa, or greater. In some embodiments, the article comprises a substrate having a ratio of a number density of electrodes to an overall elastic modulus of less than or equal to $10^{-6}$ electrodes/micron$^2$-Pa, less than or equal to $10^{-7}$ electrodes/micron$^2$-Pa, less than or equal to $10^{-8}$ electrodes/micron$^2$-Pa, less than or equal to $10^{-9}$ electrodes/micron$^2$-Pa, or less. Combinations of these ranges are possible. For example, in some embodiments, the article comprises a substrate having a ratio of a number density of electrodes to an overall elastic modulus of greater than or equal to $10^{-11}$ electrodes/micron$^2$-Pa and less than or equal to $10^{-6}$ electrodes/micron$^2$-Pa.

Another aspect of the present disclosure is directed towards various devices. In certain embodiments, these devices may be exposed to physiological conditions. For example, in some embodiments, these devices may be implanted into a subject. According to certain embodiments, a device comprises an electronic circuit. In some embodiments, an article covers at least a portion of the electronic circuit of the device. For example, according to some embodiments, an electrode of an article covers an electrode of the electronic circuit. According to certain embodiments, the article and the electronic circuit are in electronic communication. In some cases, the electronic circuit may be configured to receive a signal (e.g., an electronic signal) from the article. In some cases, the electronic circuit may be configured to amplify the signal from the article for example, according to certain embodiments, the article may be used as a sensor (e.g., a sensor of neural activity).

In certain embodiments, a method comprises applying light to a substrate. For example, according to certain embodiments light may be applied to a substrate comprising a photoresist. According to certain embodiments, light is applied through a mask. In some cases, the mask defines a pattern. For example, in some embodiments the mask defines a pattern of light on the substrate. A method may comprise aligning and patterning a fluorinated polymer (e.g., a perfluorinated polymer). The method may, according to certain embodiments, comprise aligning and patterning the perfluoropolyether. The fluorinated polymer may be aligned relative to a mask. For example, according to certain embodiments, the perfluoropolyether is aligned relative to a mask (e.g., a photoaligner mask). According to certain embodiments, the aligning comprises moving the mask relative to the substrate. In some embodiments, photoresist spacers are deposited on a substrate comprising the polymer, as described above. The addition of spacers may, according to certain embodiments, allow the mask to contact the spacers without contacting the polymer. Advantageously, the addition of spacers can prevent the mask from damaging the polymer during alignment, according to certain embodiments. In some embodiments, material is deposited onto the substrate and/or the photoresist based on the pattern of the mask. For example, the material may be metal. In some embodiments, a portion of the photoresist is removed to produce a substrate patterned with the deposited material.

In certain embodiments, the pattern has a lateral resolution. For example, in some embodiments the pattern has a lateral resolution at or below 30 micrometers, at or below 20 micrometers, at or below 10 micrometers, at or below 5 micrometers at or below 2 micrometers, or below.

According to certain embodiments the light has an average wavelength. The average wavelength of the light, in some embodiments, is less than or equal to 1500 nanometers, less than or equal to 1000 nanometers, less than or equal to 800 nanometers, less than or equal to 750 nanometers, less than or equal to 600, or less. The average wavelength of the light, in some embodiments, is greater than or equal to 100 nanometers, greater than or equal to 200 nanometers, greater than or equal to 300 nanometers, or greater. Combinations of these ranges are possible. For example, according to certain embodiments, the average wavelength of the light is greater than or equal to 100 nanometers and less than or equal to 1500 nanometers.

In some embodiments, at least a portion of an article (e.g., a sensor, a substrate, etc.) is implanted in a subject. For example, part or the entire article may be implanted in a subject. The article may be implanted in a location of a subject. For example, the article may be implanted in the brain. In some embodiments, the article is configured for long-term internal residence to a subject. The article may, for instance, be configured for long-term internal residence in an organ of a subject. For example, the article may be configured for long-term internal residence in the brain of subject. In some embodiments the article may be a brain probe or a neural sensor.

The following applications are each incorporated herein by reference, in their entirety, for all purposes: U.S. Provisional Application No. 63/159,623, filed Mar. 11, 2021, and entitled "Perfluorinated Elastomers for Brain Probes and Other Applications,"; and U.S. Provisional Application No. 63/290,732, filed Dec. 17, 2021, and entitled "Fluorinated Elastomers for Brain Probes and Other Applications."

The following examples are intended to illustrate certain embodiments of the present invention, but do not exemplify the full scope of the invention.

Example 1

This example describes the preparation of metal interconnects on the surface of a perfluoropolyether layer. In this example, the perfluoropolyether is perfluoropolyether dimethylacrylate (PFPE-DMA), which is an elastomer. First, a layer of the PFPE-DMA was prepared on a substrate. A photoresist was then deposited on the PFPE-DMA layer. Using a nitrogen chamber and a mask aligner, the photoresist was photo-degraded to pattern the surface, revealing a patterned portion of the PFPE-DMA layer. The patterned portion of the PFPE-DMA had a lateral resolution below 5 micrometers. The patterned portion of the PFPE-DMA was exposed to argon plasma to form treated PFPE-DMA, and an aluminum adhesion layer was sputtered onto the exposed surface. Next, gold was deposited onto the aluminum, producing a layer of gold interconnects and electrodes atop the patterned portion of the PFPE-DMA layer. Finally, excess metal was removed by the lift-off method. In this example, the remaining photoresist was photodegraded to remove excess metal deposited on the photoresist. The result was a patterned gold circuit portion, comprising gold interconnects and electrodes, deposited on the surface of a PFPE-DMA layer with a lateral resolution below 5 micrometers.

In some cases, a second argon plasma exposure was used in the absence of a mask to allow the deposition of additional layers. For example, in one case, a PFPE-DMA layer was deposited on top of the of the circuit, forming a third layer that encapsulated the conductive layer. In some cases, the first argon plasma exposure can be used in the absence of a mask, to deposit a PFPE-DMA layer atop a previously deposited PFPE-DMA layer. By iterating this process, it was possible to fabricate PFPE-DMA layers with thicknesses exceeding 300 nanometers. In turn, this allowed fabrication of electronics on PFPE-DMA layers with thicknesses exceeding 300 nanometers. By iterating this approach, multi-layered encapsulated circuits may be fabricated inside PFPE-DMA layers.

These results demonstrate the production of multilayered articles comprising perfluoropolyether layers. In particular, these results demonstrate that such multilayered articles may be used to produce circuits comprising gold electrodes and gold interconnects encapsulated within PFPE-DMA.

Example 2

In some cases, deposited perfluoropolyether layers may exhibit a high specific electrochemical impedance modulus after prolonged exposure to aqueous salt solutions. This example compares the decrease in measured specific electrochemical impedance modulus of polymers after prolonged immersion in a solution of 1× or 10× phosphate buffer solution at 37° C. or 70° C. Layers of perfluoropolyethers such as PFPE-DMA were compared to layers of polydimethylsiloxane (PDMS), styrene-ethylene-butylene-styrene (H-SEBS), polyimide (PI), and SU-8 2000.5 epoxy photoresist, which in this example serve as comparisons.

Electrochemical impedance measurements were performed in the phosphate buffer solution, using a standard three-electrode setup for measuring electrochemical impedance. FIG. 2 illustrates the setup for a three-electrode electrochemical impedance measurement. In these experiments, working electrode (gold) 122 was connected to a conductor 108 deposited on substrate 124 and encapsulated within dielectric layer 126 comprising one of the polymers. Two other electrodes, counter electrode 110 (platinum) and reference electrode 112 (silver/silver chloride), were connected to the other side of the dielectric layer, allowing electrochemical impedance measurement using a SP-150 potentiostat from Bio-logic©, along with its commercial software (EC-lab). The experiments were performed in buffer solution 114. This technique provides an estimation of the ionic diffusivity based on the time required to observe the impedance drop, and an estimation of the ionic conductivity based on the Nyquist plots obtained.

For each measurement, three sweeps in frequency were measured, from 1 MHz down to 0.1 Hz. A sinusoidal voltage of 100 mV peak-to-peak was applied. Five points per frequency decade, logarithmically spaced, were measured. For each data point, the response to 10 consecutive sinusoids (but spaced out by 10% of the period duration) was accumulated and averaged. The thickness of each layer, H, was determined as a fraction of a micrometer (e.g., a sample 3 micrometers thick is described by H=3.0). All the thickness measurements have been carried out using a Bruker Dektak Xt Stylus profiler. The force applied was set to 1 milligram, and the scan speed to 0.67 micrometers per second. Two-points surface leveling was applied using the commercial software of the tool.

Figure 4A:
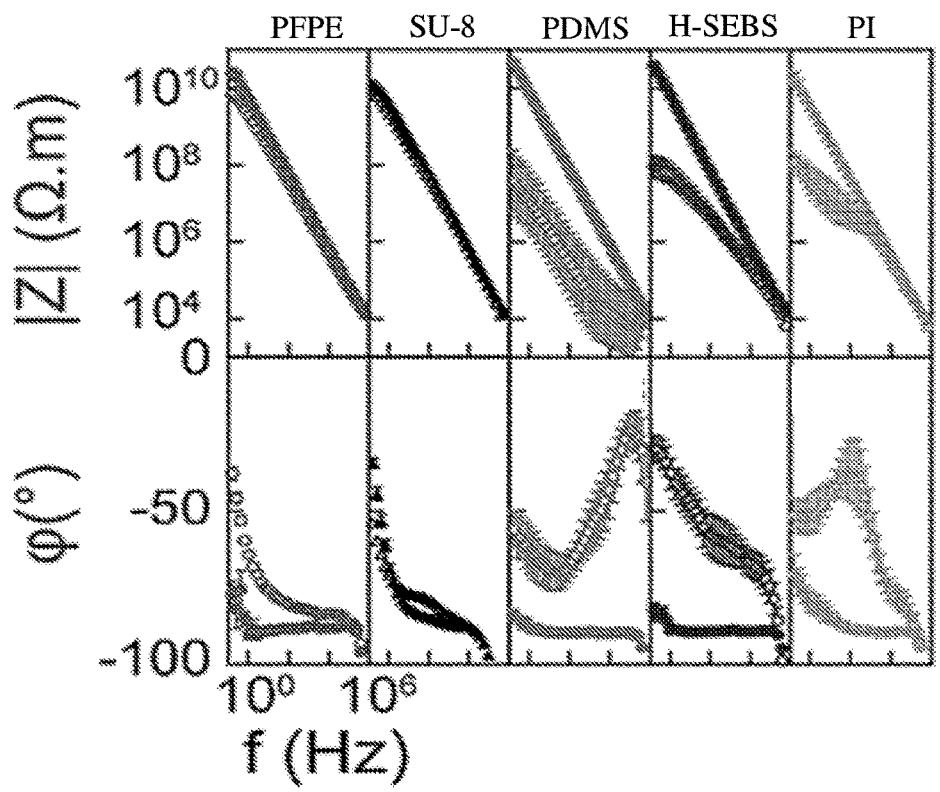
FIGS. 4A-4D present specific electrochemical impedance measurements of polymer films, according to certain embodiments.
Figure 4B:
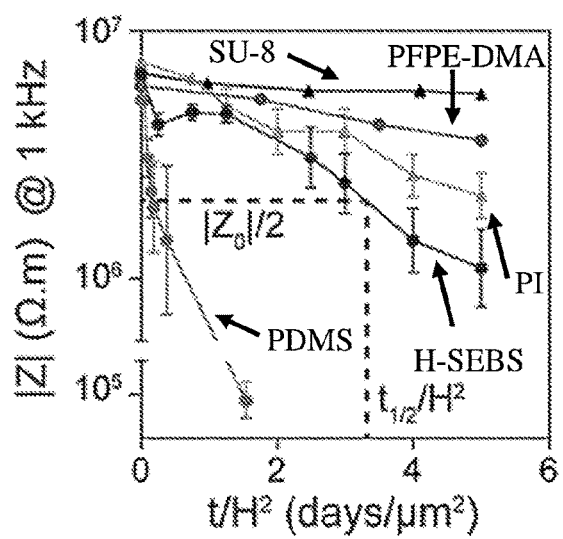
Figure 4C:
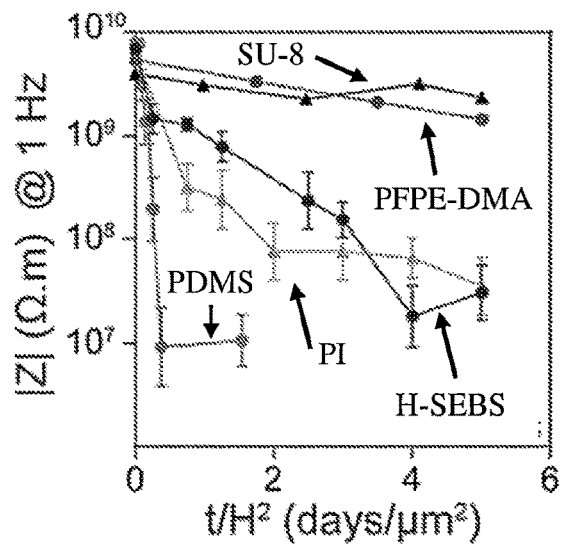
Figure 4D:
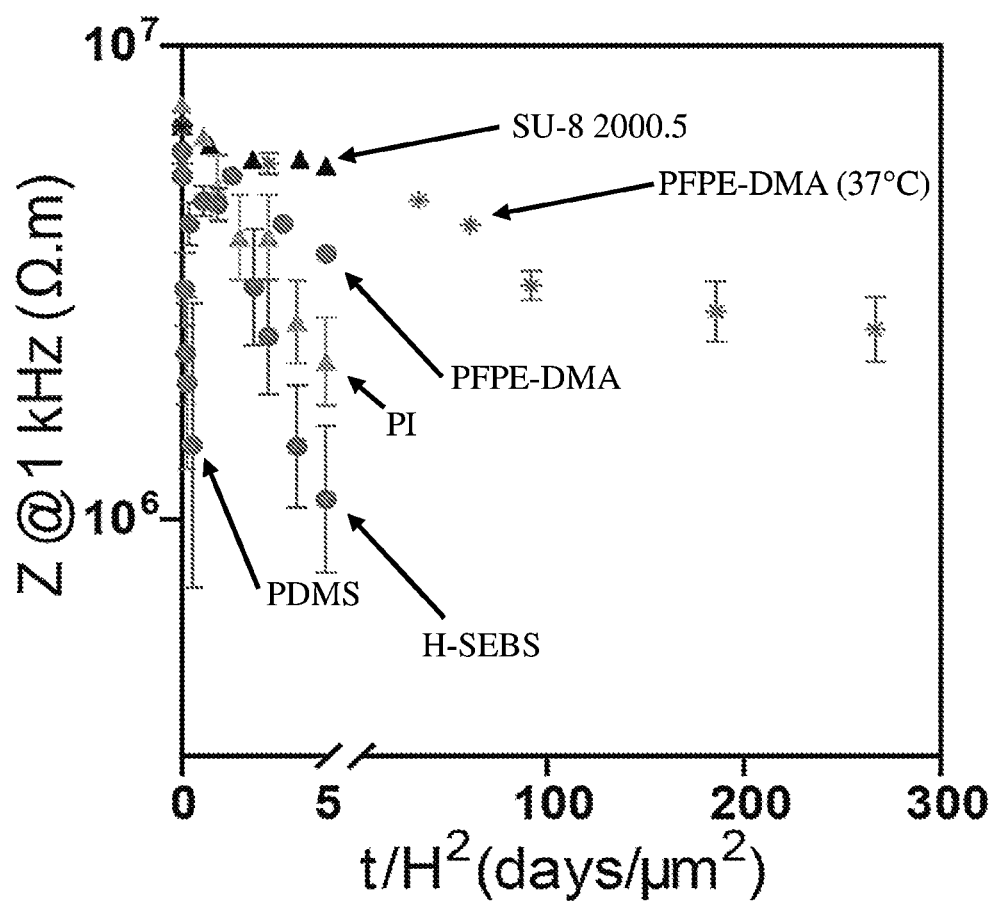

Polymer layers were immersed under rapid aging conditions at 70° C. in 10× phosphate buffer solution (PBS). FIG. 4A plots the specific electrochemical impedance modulus (top) and phase (bottom) of dielectric polymers under pristine conditions and after aging in 10×PBS at 70° C. (at $t/H^2=5$ days/micrometers$^2$ for PFPE, SU-8, H-SEBS, PI, and $t/H^2=1.55$ days/micrometers$^2$ for PDMS). FIGS. 4B and 4C present the specific electrochemical impedance modulus of the immersed layer as a function of time (normalized by $H^2$), determined at 1 kHz and at 1 Hz, respectively. Under rapid aging conditions, all polymers experienced decreases in specific electrochemical impedance modulus. However, the specific electrochemical impedance modulus of the PFPE-DMA layer, much like the specific electrochemical impedance modulus of the SU-8 layer, decreased very slowly, compared to the specific electrochemical impedance modulus of the other polymers. These data demonstrate the long-term stability of perfluoropolyether layers under physiological salt conditions. FIG. 4D is similar to FIG. 4B, but adds electrochemical impedance measurements recorded for a PFPE-DMA layer under physiological conditions (37° C., 1×PBS). This visualization demonstrates the stability of the PFPE-DMA layer for over 250 days under physiological conditions.

These results were further validated by a conductance measurement. In these measurements, large areas (ranging from 150 to 300 centimeters$^2$) of dielectric thin films were prepared on glass slides according to the protocols used to prepare films for electrochemical impedance measurements, then immersed in deionized water to facilitate their peel off. After being peeled off, the crumpled films were transferred to glass vials for the remaining of the experiment. The crumpled thin films were first immersed for 3 weeks in deionized water, replaced regularly, at ambient temperature to remove any impurities which could contribute to the ionic conductivity. A conductometer (a Traceable® Conductivity Pocket Tester with Calibration) was used to confirm that the surrounding solution's conductivity remained negligible after 3 weeks, ensuring that the wash out process was over. The two electrodes of the conductometer had an area of 1 centimeters$^2$ and were separated by 1 centimeters. The resolution of the sensor was 1 microsiemens, and temperature-dependence of the conductance in the range, −5-50° C., was automatically compensated to give the value at 25° C.

Samples were transferred to new glass vials in a large volume of 10×PBS solution, at a fixed temperature (4° C., 37° C. or 65° C.) for 3 weeks, to be fully immersed by ions. It was verified a posteriori that 3 weeks was a long time compared to the characteristic diffusion time of ions in the materials. After reaching the equilibrium immersing in biofluids, samples were thoroughly rinsed in two successive deionized water solutions (30 seconds in each) to remove ions on the surface, then dried at 65° C. for 30 minutes, before mass measurements were collected.

Figure 5A:
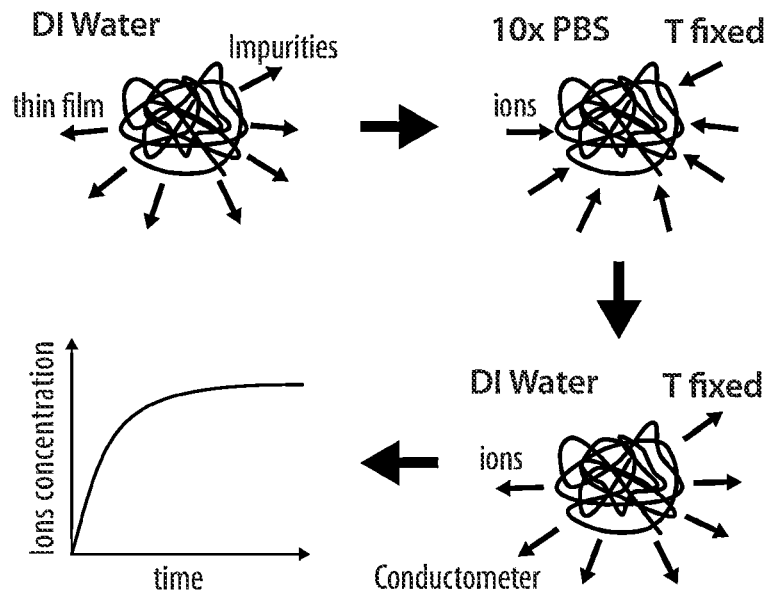
FIG. 5A presents an illustrated method of determining ion concentration of a polymer, according to certain embodiments.
Figure 5B:
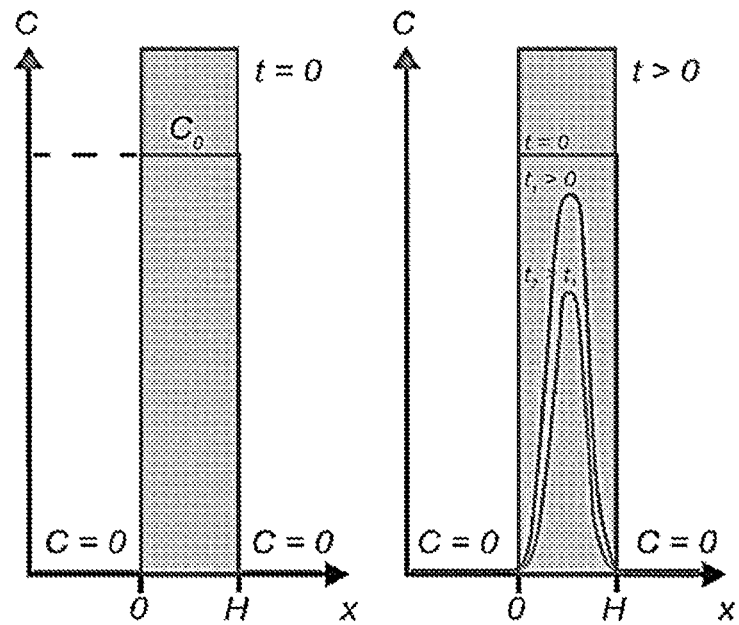
FIG. 5B present exemplary concentration profiles of ions after exposing a polymer that had previously equilibrated with a buffer to deionized water.
Figure 5C:
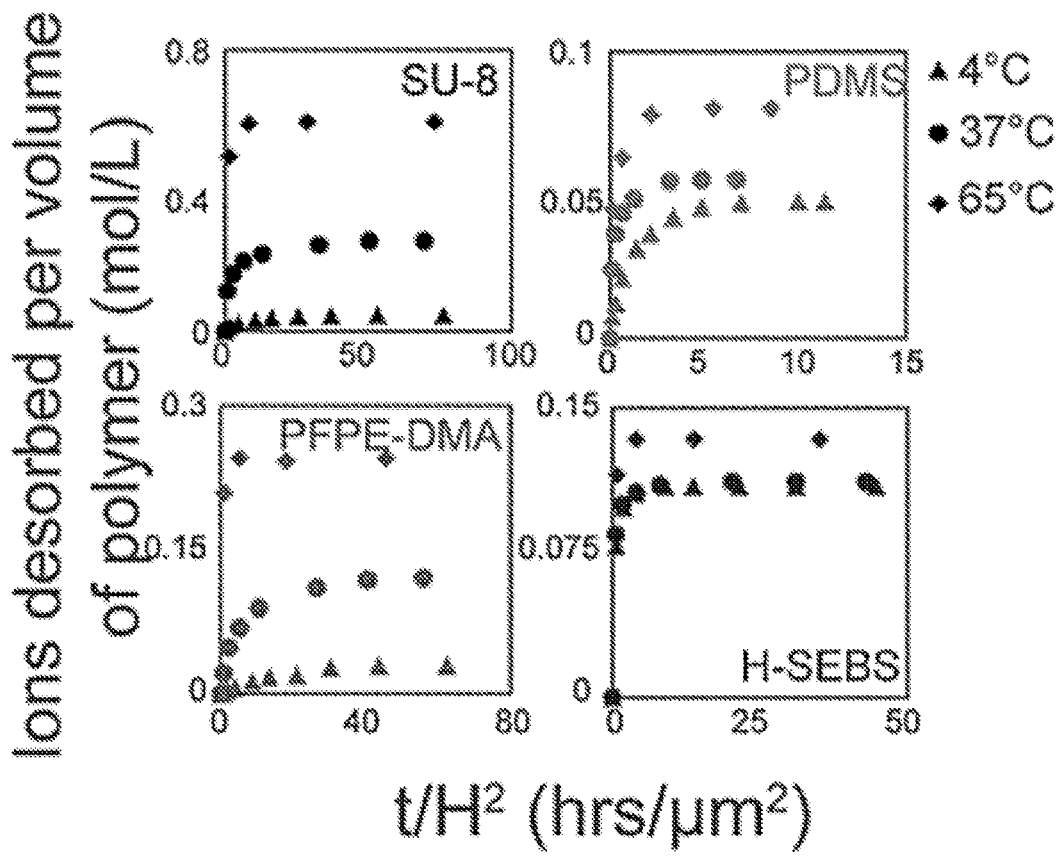
FIGS. 5C-5D compare the ion desorption of polymer layers at various temperatures, according to certain embodiments.

Next, samples were transferred to new glass vials containing 4.00 mL of deionized water and stored at a fixed temperature (4° C., 37° C. or 65° C.). The water contained a conductimetry cell to monitor temperature and conductance. Conductance of the deionized water solution was measured regularly, to determine the quantity of ions desorbed by each material over time. This process is schematized in FIG. 5A, which illustrates the perfluoropolyether equilibrating in deionized (DI) water, then absorbing ions as it equilibrates in 10× phosphate buffer solution, and then emitting ions as it equilibrates once again in DI water, in the presence of a conductometer. FIG. 5B illustrates the boundary conditions and diffusion profile that result from such conditions, illustrating the evolution of the concentration profile at different time-points. The change in conductance allowed determination of the concentration of ions desorbed by each dielectric polymer over time, at various temperatures. FIG. 5C presents the results of these experiments, illustrating the ion concentration in the initially deionized water for each polymer at 4° C., 37° C., and 65° C. as a function of time (normalized by $H^2$).

Figure 5D:
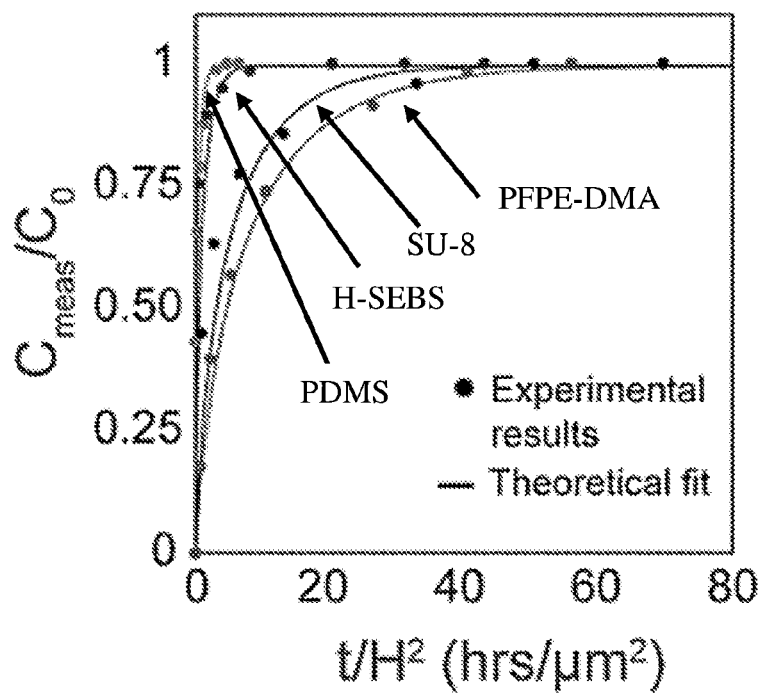
Figures 5E, 6:
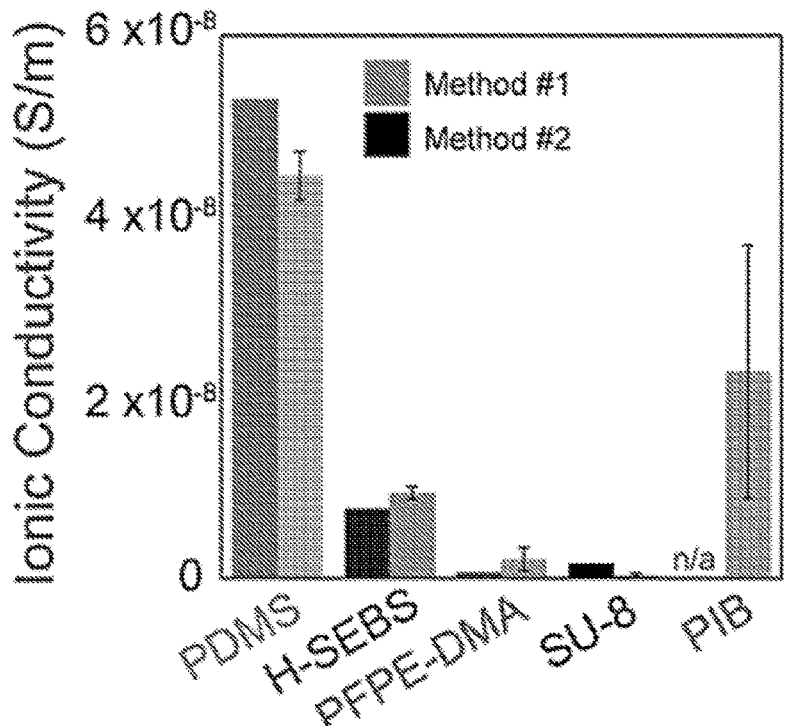
FIG. 5E compares the ionic conductivity of polymer layers determined by different measurements, according to certain embodiments.
FIG. 6 presents an equation used to determine ionic conductivity, according to certain embodiments.

The plateau in concentration is directly proportional to the ionic solubility, S, of the polymer, while the theoretical solution of the corresponding diffusion, one-dimensional, boundary problem was fitted to the experimental data to obtain ionic diffusivity, D. FIG. 5D presents the experimental results and the theoretical fits for each polymer at 37° C. The ionic conductivity was then determined using equation (1), presented in FIG. 6, $$\sigma = 2\frac{q^2}{kT} D * S * C_{out} \tag{1}$$

where σ (sigma) is the ionic conductivity, q, the unit charge, k, the Boltzmann constant, T, the temperature, D, the ionic diffusivity, S, the ionic solubility and $C_{out}$ the concentration of ions in the surrounding biofluids at equilibrium. The ionic conductivity determined by electrochemical impedance measurements (Method #1) is compared with the ionic conductivity determined by conductance measurements (Method #2) in FIG. 5E, showing good agreement. Both methods agreed, in terms of both general trends and order of magnitude. According to both measurements, PFPE-DMA stood out from other dielectric elastomers by its low ionic conductivity, which results from its low ionic diffusivity (Table 2).

TABLE 1

Ionic conductivity, diffusivity and solubility in dielectric polymers obtained by conductance.

| Material | σ (S/m) | D (m²/s) | S |
|---|---|---|---|
| PDMS | 5.30 10⁻⁸ | 2.55 10⁻¹⁵ | 0.0404 |
| H-SEBS | 7.62 10⁻⁹ | 1.82 10⁻¹⁶ | 0.0814 |
| PFPE-DMA | 6.34 10⁻¹⁰ | 1.4 10⁻¹⁷ | 0.0881 |
| SU-8 | 1.62 10⁻⁹ | 1.69 10⁻¹⁷ | 0.187 |

Figure 7A:
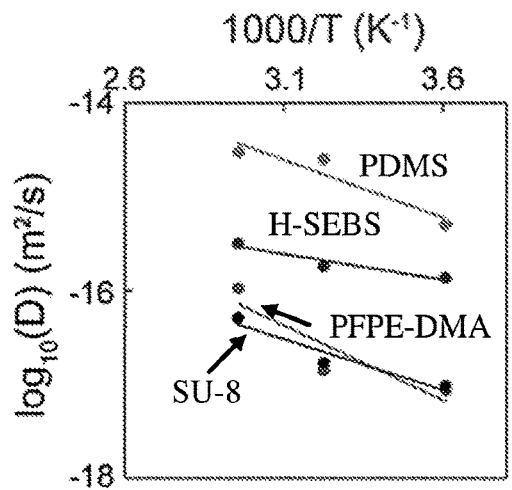
FIGS. 7A-7C compare the temperature dependence of ion behavior within polymers, according to certain embodiments.
Figure 7B:
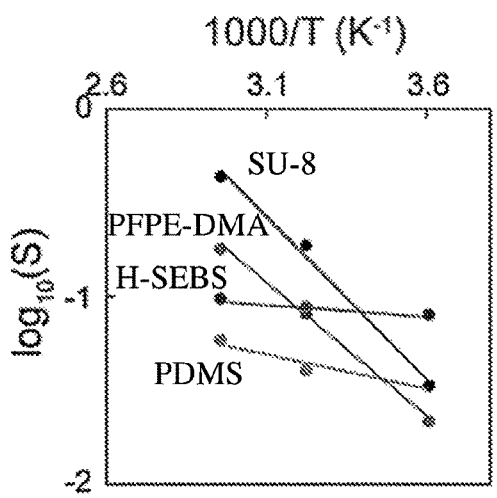
Figure 7C:
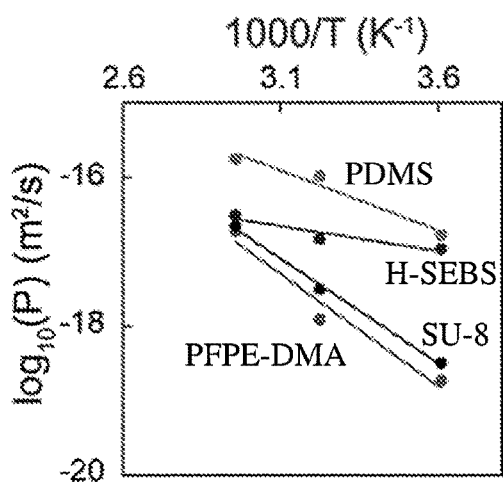

To further understand the nature of the low ionic conductivity in PFPE-DMA, conductance was measured at various temperatures to determine the average activation energy for diffusion and the heat of solution of ions in the range 4° C.-65° C. using an Arrhenius relationship. FIGS. 7A-7C are Arrhenius plots of ionic diffusivity D (FIG. 7A), ionic solubility S (FIG. 7B), and ionic permeability P (FIG. 7C) measured for each polymer. The linear fits were used to obtain energy parameters in Table 2. Both in terms of diffusivity and solubility trends, PFPE-DMA is closer to SU-8 than to the other elastomers.

TABLE 2

Average activation energy $E_a$ for ionic diffusivity, and heat of solution $H_s$ for ionic solubility calculated from the Arrhenius model.

| Material | PDMS | H-SEBS | PFPE | SU8 |
|---|---|---|---|---|
| $E_a$ (kJ/mol) | 10.32 | 4.56 | 13.25 | 9.02 |
| $H_s$ (kJ/mol) | 3.03 | 1.04 | 11.83 | 14.35 |

Example 3

This example demonstrates a method of characterizing the cross-linking of perfluoropolyether layers using specific electrochemical impedance measurements. To do this, an as-deposited layer of a perfluoropolyether, in this case PFPE-DMA, with a thickness of H (as described in Example 2), was immersed in 1,3-bis(trifluoromethyl)benzene for a period of 30 s/$H^2$ while gently agitating to remove uncross-linked polymer chains. Next, the sample was dried using nitrogen air flow. Finally, the sample was immersed in 1× phosphate buffer solution, and its electrochemical impedance was measured according to the protocol of Example 2. In general, films known to have a greater degree of cross-linking were observed to have substantially higher specific electrochemical impedance modulus, demonstrating that specific electrochemical impedance modulus may be used as an indirect test of cross-linking in these films.

Example 4

This example describes the preparation of a perfluoropolyether dimethylacrylate (PFPE-DMA) photolithography precursor. All chemicals were obtained from Sigma-Aldrich unless otherwise mentioned and used without further purification. All descriptions of the volume fraction corresponded to the volume of 1,1,1,3,3-pentafluorobutane.

First, 0.8 g/mL PFPE diol was dissolved in 1,1,1,3,3-pentafluorobutane (Alfa Aesar, H33737). The solution was mixed for 3 hours. Then the solution was added with 22 mg/mL isophorone diisocyanate (IPDI, 317624), 0.8 mg/mL dibutyltin diacetate (DBTDA, 290890) and reacted in nitrogen environment for 48 hours. The product could be thick or solid. Then the product was added with 30 mg/mL 2-isocyanatoethyl methacrylate (IEM, 477060) and 0.8 mg/mL DBTDA and further reacted at room temperature in nitrogen environment for 48 hours. The final product solution was filtered with a 0.2 micrometer glass fiber syringe filter to yield clear and colorless oil. The IPDI solvent in the oil was removed by rotary evaporation to get pure PFPE-DMA. Finally, 0.5-1.5 g/mL PFPE-DMA and 1 wt % photoinitiator bis(2,4,6-trimethylbenzoyl)-phenylphosphineoxide (511447) were dissolved in bis(trifluoromethyl)benzene (251186) to yield the precursor.

Example 5

Figure 8:
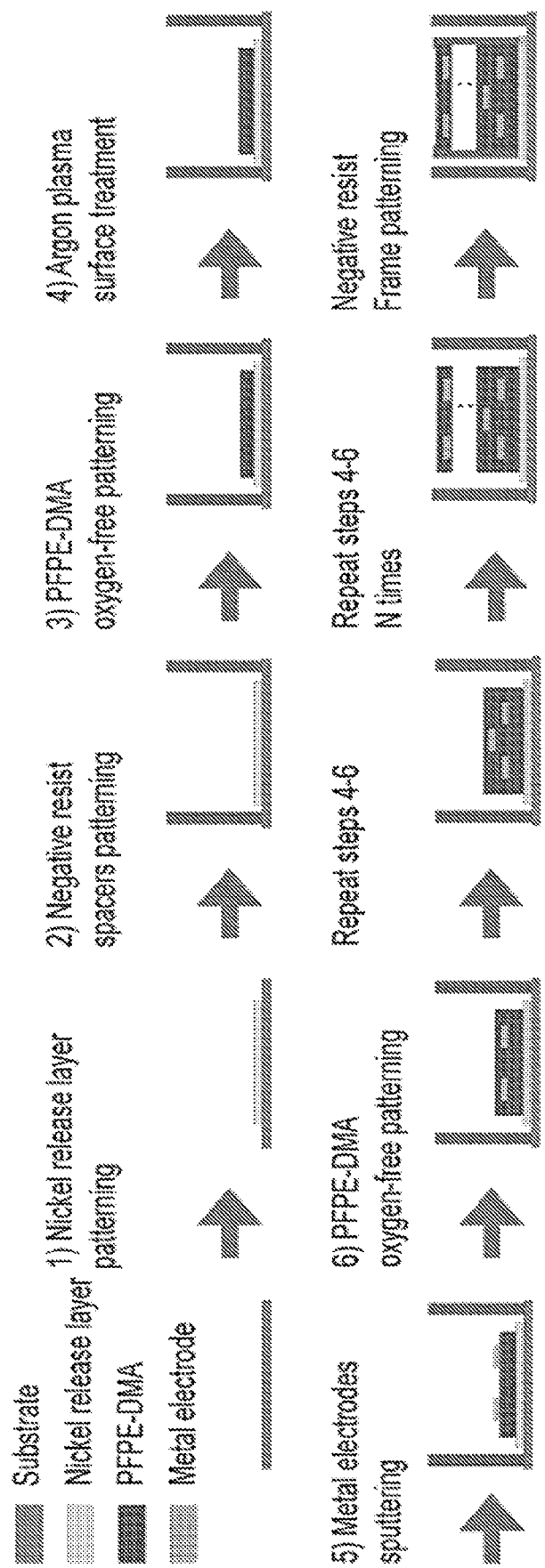
FIG. 8 presents an exemplary method of preparing an article comprising a perfluorinated polymer, according to certain embodiments.

This example demonstrates an exemplary method used to fabricate certain articles comprising perfluoropolyethers. In a more specific embodiment, this method was used to fabricate PFPE-DMA encapsulated brain probes. FIG. 8 presents a schematic representation of this exemplary method. All photoresist and developers were obtained from MicroChem Corporation unless otherwise mentioned.

1. The device fabrication began with the preparation of the Ni sacrificial layer (FIG. 8, step 1). A 3-inch thermal oxide silicon wafer (2005, University wafer) was rinsed with acetone, rinsed with isopropyl alcohol (IPA), rinsed with water and blown dry. Then, the 3-inch thermal oxide silicon wafer was baked at 110° C. for 3 minutes and treated with oxygen ($O_2$) plasma at 100 W, 40 standard cubic centimeters per minute (sccm) of $O_2$ for 30 s. Layers of hexamethyldisilazane, LOR 3A photoresist, and S1805 photoresist were spin-coated on the wafer at 4000 rpm for 1 minute. The LOR 3A photoresist was hard-baked at 180° C. for 5 minutes following its deposition. After this, the S1805 photoresist was applied and hard-baked at 115° C. for 1 minute. Then the photoresists were exposed under 40 mJ/centimeters$^2$ UV light and developed with CD 26 developer for 50 s, rinsed with DI water and blown dry. After that, a 100 nanometers Ni layer was thermally deposited on the wafer and lifted off in Remover PG, an N-methyl-2-pyrrolidone (NMP) based solvent stripper, for 3 hours.

2. Next, negative photoresist was used to make spacers. SU-8 2010 epoxy photoresist was spin-coated on the wafer at 3000 rpm for 2 minutes, and pre-baked at 60° C. for 2 minutes, then 95° C. for 4 minutes. The SU-8 2010 epoxy photoresist was exposed with 200 mJ/centimeters$^2$ UV light, then post-baked at 60° C. for 2 minutes, 95° C. for 2 minutes 30 s. Finally, the SU-8 2010 epoxy photoresist was developed in SU-8 developer (1-methoxy-2-propanol acetate) for 2 minutes, rinsed with IPA and blown dry.

Figure 9B:
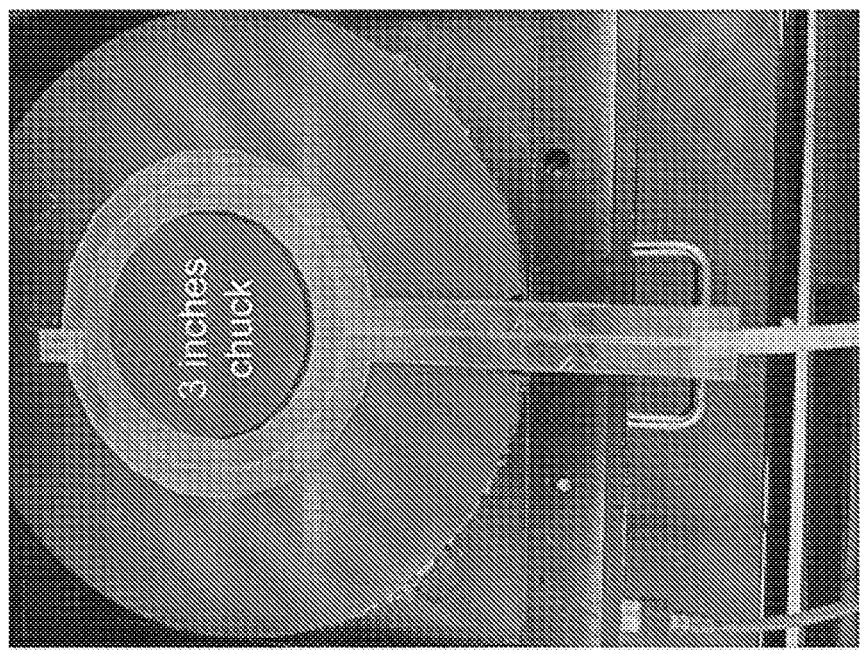
FIGS. 9A-9B present an exemplary nitrogen diffuser, according to certain embodiments.
Figure 9A:
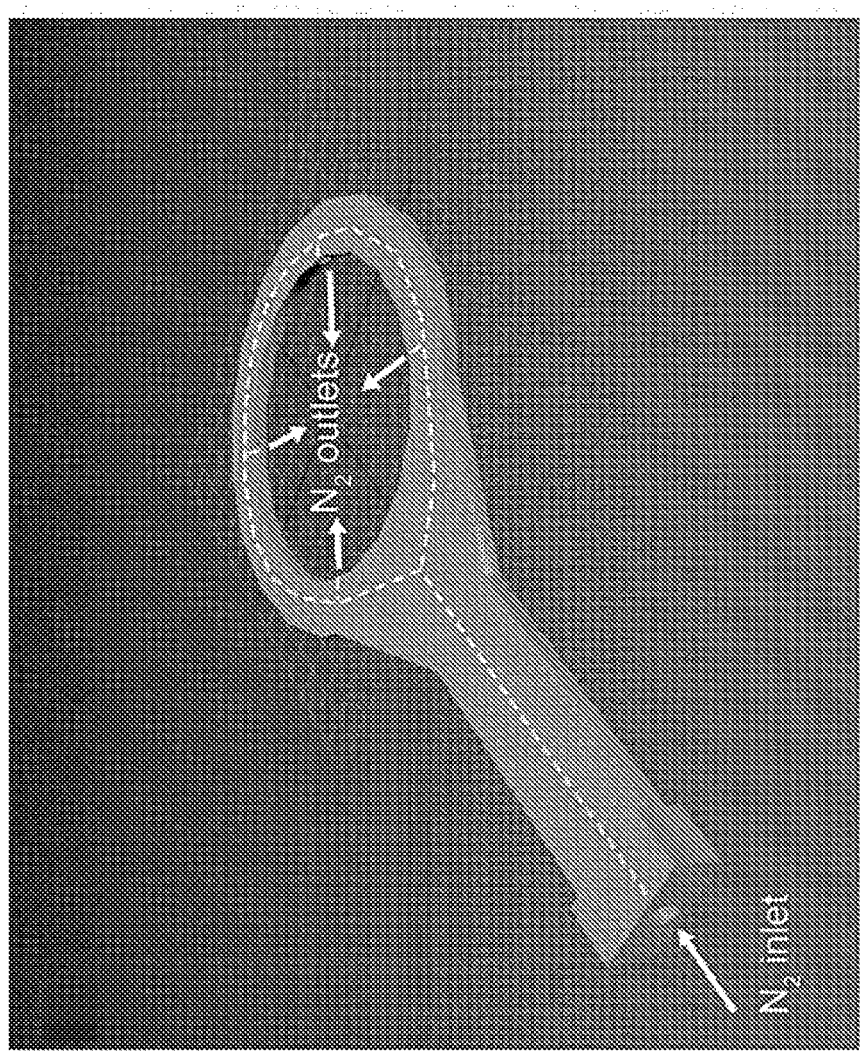

3. The bottom PFPE-DMA layer was fabricated (FIG. 8, step 3). The wafer was firstly cleaned with acetone, IPA, water and blown dry. Then the PFPE-DMA precursor described in Example 4 was spin-coated on the wafer in the range of 2000-6000 rpm for 1 minute and pre-baked at 95° C. for 1 minute, to obtain a thickness ranging between 500 nanometers and 3 micrometers, depending on the rotation speed and precursor concentration. The PFPE-DMA was aligned in a photomask aligner and patterned with 20 mJ/centimeters$^2$ UV, using an exemplary, customized nitrogen diffuser. FIG. 9A presents a schematic representation of the exemplary nitrogen diffuser, while FIG. 9B presents a photograph of the exemplary nitrogen diffuser, disposed on a Karl Suss MA6 mask aligner. Then the PFPE was post-baked at 95° C. for 1 minute and developed in developer (bis(trifluoromethyl)benzene:1,1,1,3,3-pentafluorobutane=1:3) for 1 minute and blown dry. The PFPE pattern was hard baked at 150° C. for 50 minutes.

4. Metal traces were fabricated on the top of the bottom PFPE-DMA (FIG. 8, step 4). The bottom PFPE was first surface treated with argon plasma at 20-30 W, 40 sccm argon, for 2-6 minutes.

5. Positive photoresists, LOR 3A and S1805 or S1813, were patterned on the wafer as described in step 1, to prepare the sacrificial layer. After that, the surface was treated again with argon plasma (20-30 W, 40 sccm argon, for 2-6 minutes), then aluminum-gold, or aluminum-gold-aluminum, or aluminum-gold-platinum, or chromium-gold, or chromium-gold-chromium metal layers were sequentially deposited by sputtering, with thicknesses in the range 20-100 nanometers for each layer. Finally, the metal layers were lifted off in Remover PG overnight (FIG. 8, step 5).
6. A subsequent PFPE-DMA layer was deposited (FIG. 8, step 6), following the method described in step 3.
7. Steps 4 to 6 can be repeated multiple times to obtain the desired number of metal electrodes layers, fully encapsulated by perfluorinated elastomer.
8. Negative photoresist was used to make the microfabricated plastic frame that holds the perfluorinated elastomer-encapsulated brain probe flat during release. One method used SU-8 2010 spacers (FIG. 8, step 2), as described here. SU-8 2010 was spin-coated on the wafer at 3000 rpm for 2 minutes, and pre-baked at 60° C. for 2 minutes, then 95° C. for 4 minutes. SU-8 was exposed with 200 mJ/centimeters$^2$ UV light, then post-baked at 60° C. for 2 minutes, 95° C. for 2 minutes and 30 seconds. Finally, SU-8 2010 was developed in SU-8 developer for 2 minutes, rinsed with IPA and blown dry. Different SU-8's can be used depending on the final thickness desired for the microfabricated plastic frame, which has to be thicker than the total thickness of the brain probe. This fabrication process has been successfully applied using SU-8 2010, SU-8 2025 and SU-8 2050.
9. A low electrochemical impedance material was, in some embodiments, plated on the tip of the electrodes by following a procedure analogous to steps 4-5, replacing the metal by platinum, aluminum-platinum, or chromium-platinum with a thickness in the range of 20-80 nanometers. A SP-150 potentiostat from Bio-Logic©, along with its commercial software (EC-lab), was used in voltage or current control for electrodeposition. Electrodes from devices were connected to the working electrode. The counter electrode was a platinum wire, also serving as voltage reference, which was immersed in the precursor solution. For platinum black, the precursor is a 0.8 wt % chloroplatinic acid solution, and the current applied was −1 mA/centimeters$^2$ for 5-10 minutes. For PEDOT-PSS deposition, electrolyte consisting of 0.01 M 3,4-ethylenedioxylthiophene (EDOT) (Sigma-Aldrich, USA) and 0.1 M sodium PSS (Sigma-Aldrich, USA) aqueous solution was used. The electrochemically polymerized reaction was performed under constant voltage conditions. In the constant voltage mode, the polymerization was carried out under a constant current of 1 V for 30 seconds.

Example 6

Figure 10A:
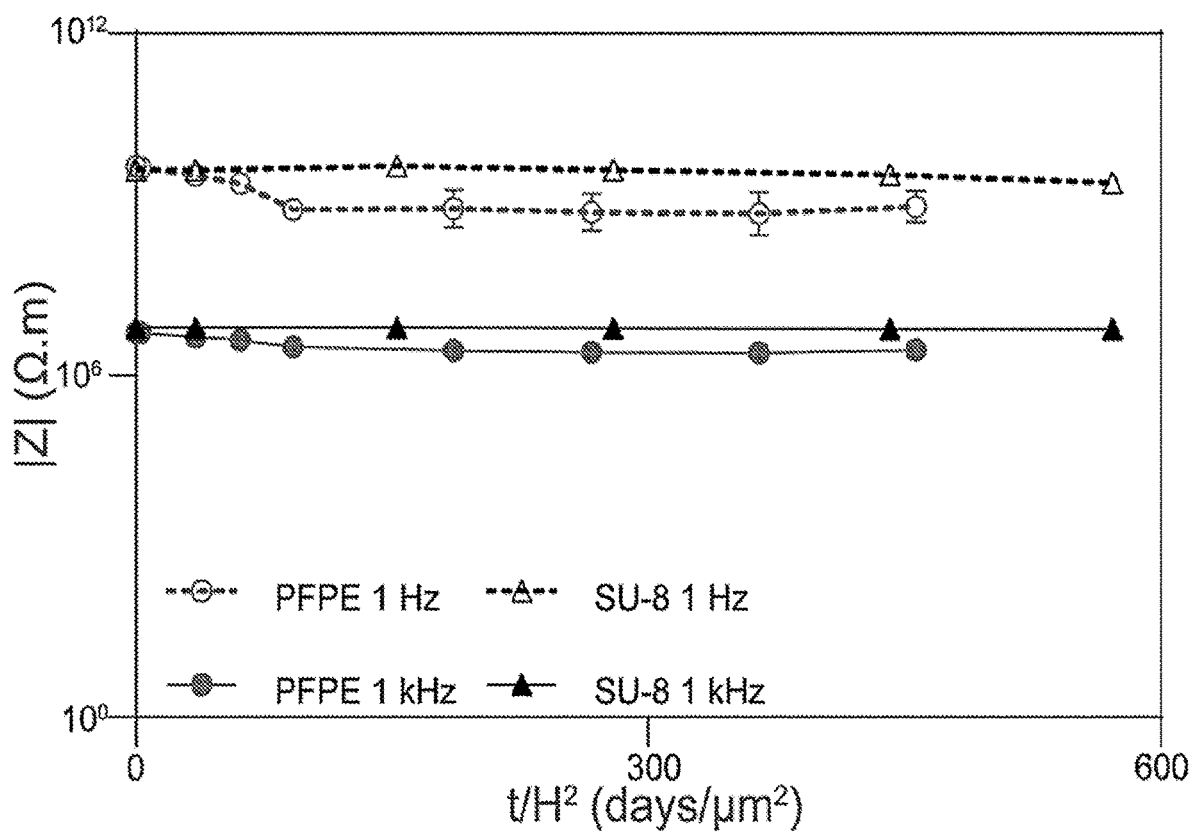
FIG. 10A compares the specific electrochemical impedance modulus of polymers, according to certain embodiments.
Figure 10B:
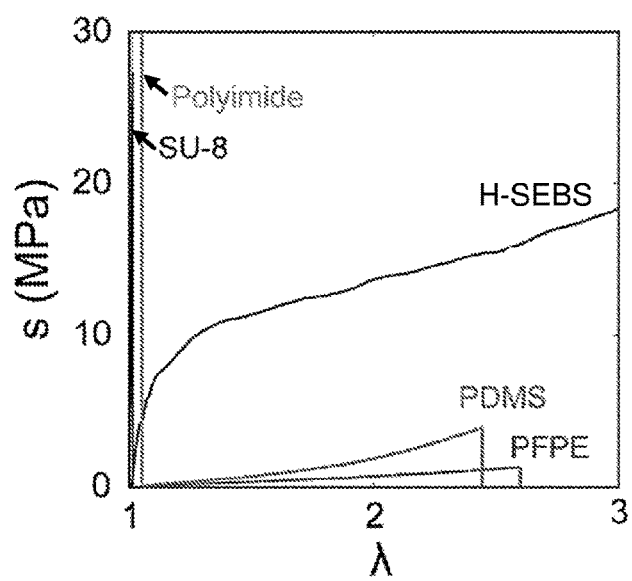
FIG. 10B presents mechanical properties of polymers, according to certain embodiments.
Figure 10C:
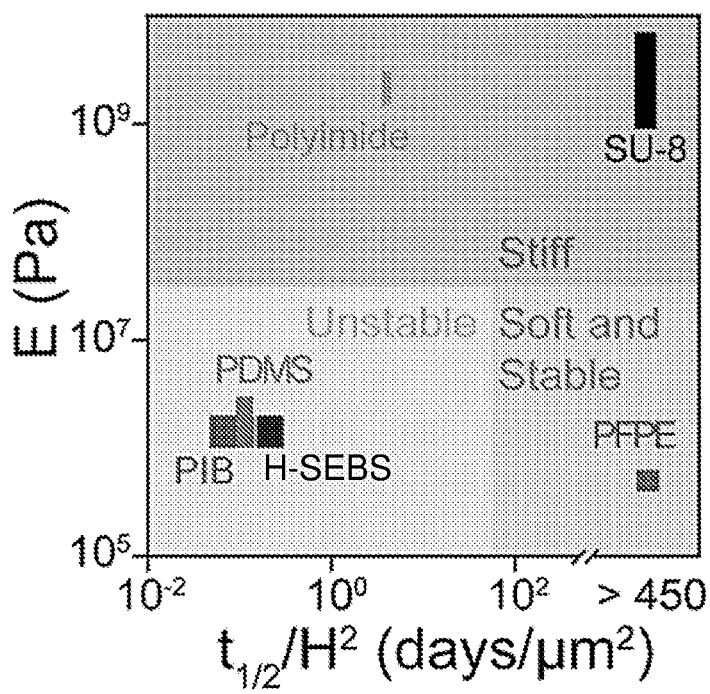
FIG. 10C compares the elastic modulus with the electrochemical stability of polymer materials, according to certain embodiments.

This example demonstrates the properties of an article comprising PFPE-DMA. A long-term immersing experiment in physiological conditions (1× phosphate buffer solution at 37° C.) was used to compare the electrochemical impedance stability of PFPE-DMA and SU-8. The results of these electrochemical impedance measurements are presented in FIG. 10A. After more than 15 months (more than 450 days), PFPE-DMA maintained a high specific electrochemical impedance modulus, sufficient to electrically insulate brain probes, and comparable to the specific electrochemical impedance modulus of SU-8. However, SU-8 is a stiff polymer with an elastic modulus in the order of 2 gigapascals, while PFPE-DMA is, according to certain embodiments, an elastomer with an elastic modulus of only 0.50 megapascals, more than 4000 times softer. Stress-stretch curves were obtained using a Instron machine in uniaxial tension for specimens in the pure shear test geometry. FIG. 10B presents the stress-stretch curves for each polymer. FIG. 10C compares elastic modulus (E) to the normalized half-life of the specific electrochemical impedance modulus ($t_{1/2}/H^2$) at 1 kHz (defined as the immersing time required to decrease the initial specific electrochemical impedance modulus by 50%) for various polymers, perfluoropolyether elastomers were the only materials with a high normalized half-life. A graphical representation of the determination of $t_{1/2}H^2$ is shown in FIG. 4B.

Example 7

This example demonstrates the nanofabrication of brain probes comprising perfluoropolyether elastomers, and demonstrates that PFPE-DMA will not swell will maintain a nanometer scale smoothness when immersed in organic solutions commonly used in photolithography.

PFPE-DMA was photopatterned using the exemplary, customized nitrogen diffuser described in Example 4 to create an inert atmosphere during UV exposure, allowing for nanoscale photo-patternability. To preserve the nanometer smoothness of PFPE-DMA, a negative photoresist spacer was patterned on the wafer to prevent the direct contact between non-cross-linked PFPE-DMA precursor and the photomask. Finally, the exposed surface of the PFPE-DMA was treated with inert gas (e.g., $N_2$, argon, etc.) plasma to enhance the adhesion of metals and other, subsequently deposited materials to the PFPE-DMA.

Figure 11A:
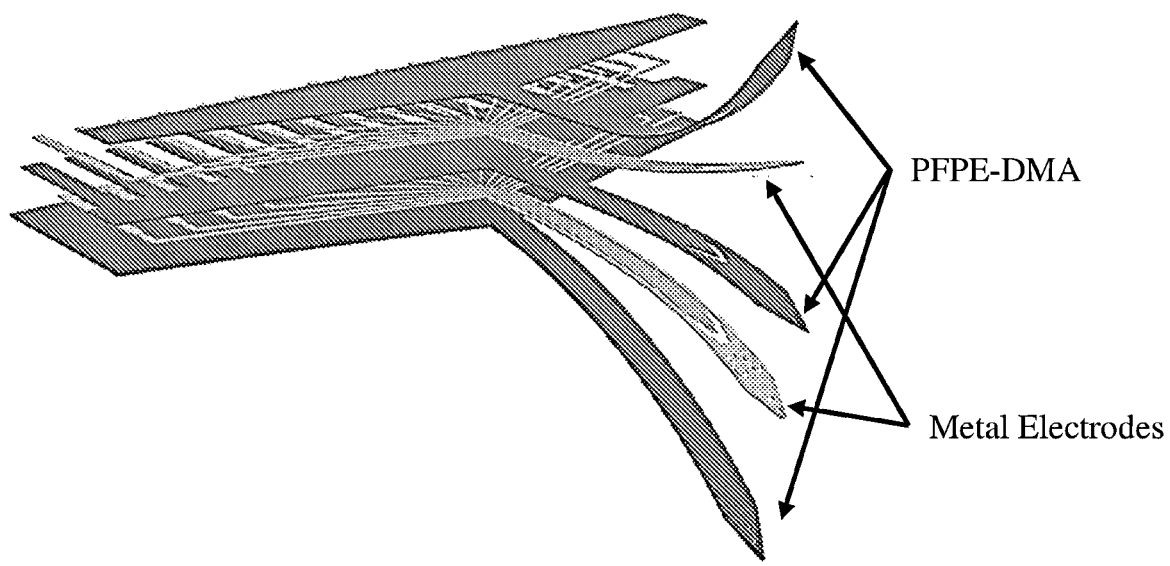
FIG. 11A presents an exploded perspective illustration of an exemplary article designed for use as a neural sensor, according to certain embodiments.
Figure 11B:
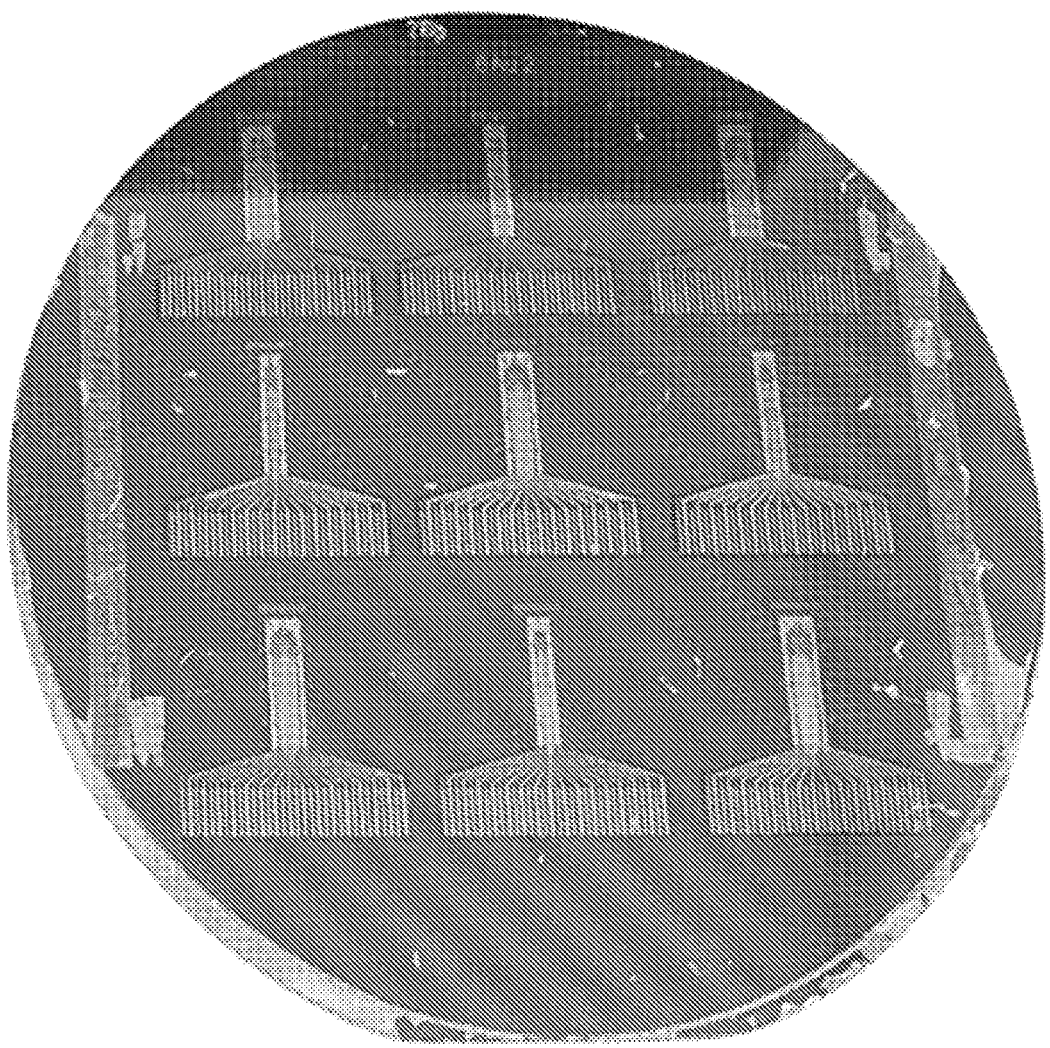
Figure 11C:
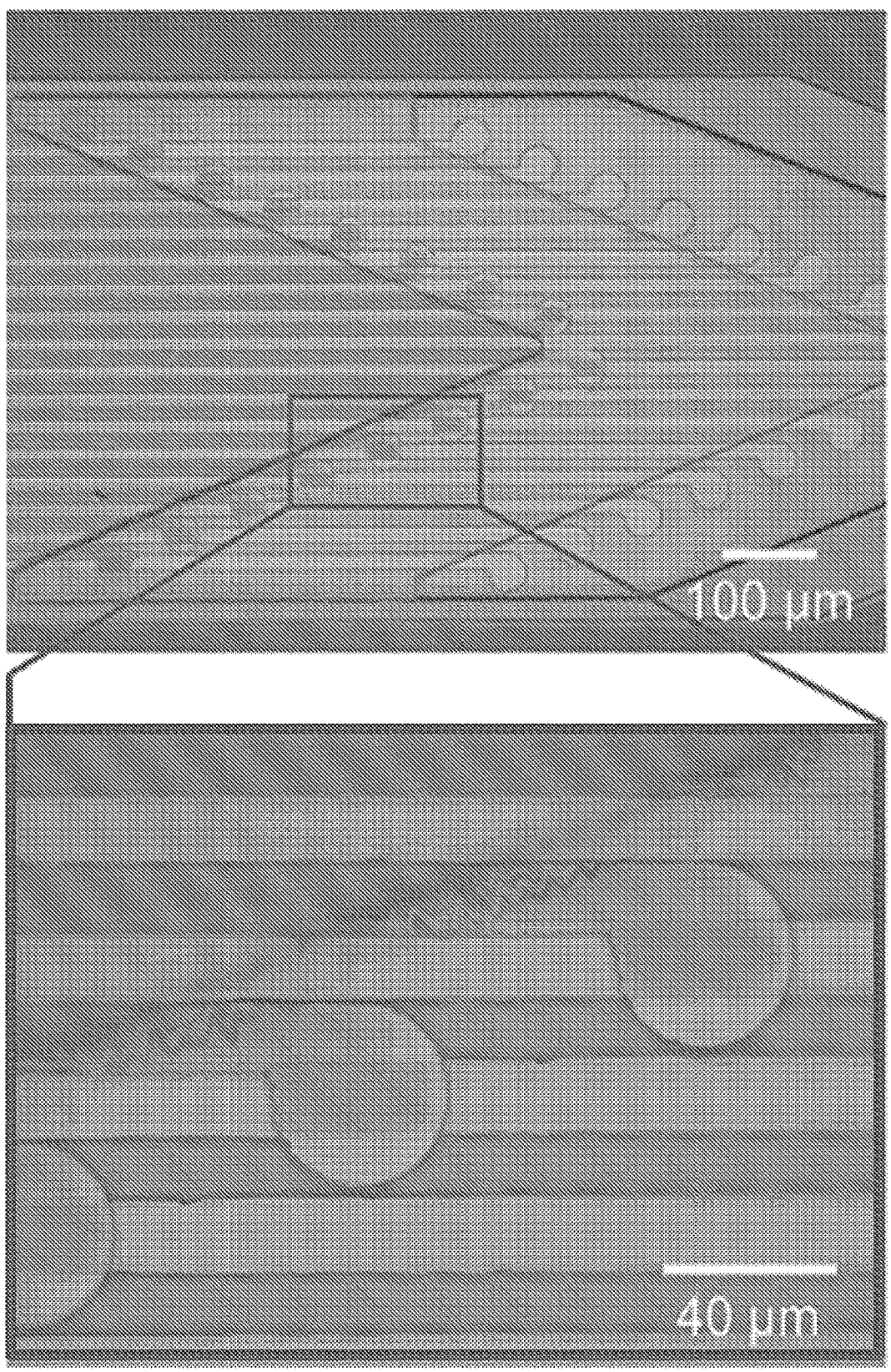
Figure 12A:
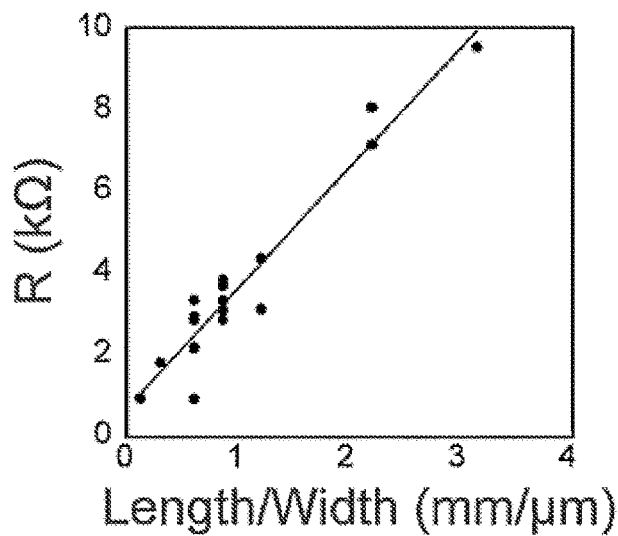
FIGS. 12A-12B present the resistance of metal electrodes, according to certain embodiments.
Figure 12B:
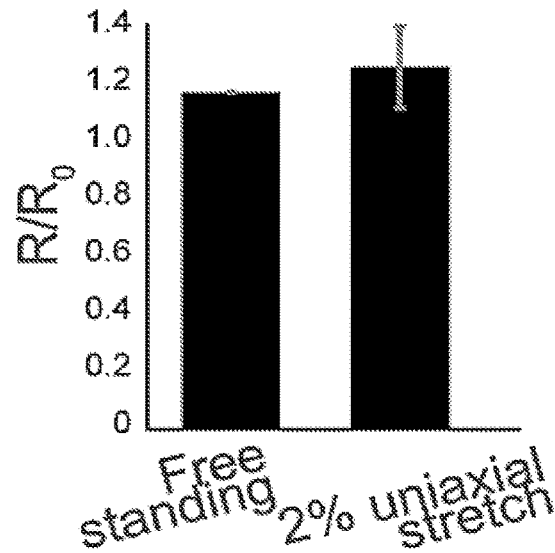
Figure 13A:
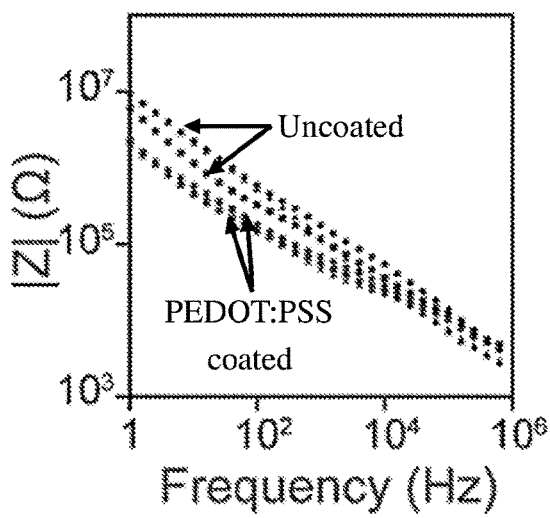
FIGS. 13A-13B compare impedance behavior of articles comprising uncorrected electrodes and electrodes coated with PEDOT:PSS, according to certain embodiments.
Figure 13B:
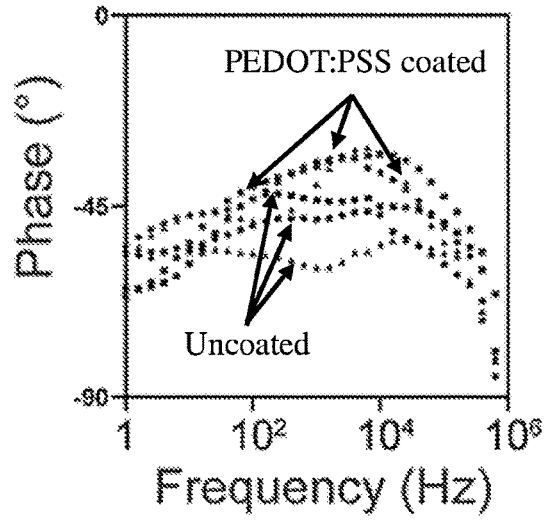

An exemplary device produced by this method, with three layers of PFPE-DMA sandwiching two layers of metal interconnects, is shown in FIG. 11A. This fabrication workflow is compatible with wafer-scale fabrication, and FIG. 11B presents exemplary devices fabricated on a 3 inch wafer (7.62 centimeters). FIG. 11C presents bright-field optical imaging that highlights the high quality of the PFPE-DMA and metal lines, patterned in an alternating sequence. FIG. 11D presents a scanning electron microscopic (SEM) image that reveals the uniform patterns across the device, while FIG. 11E presents a focused ion beam (FIB) cross-sectional image that shows (i) no delamination from PFPE-DMA layers, and (ii) sputtered metal interconnects formed tight bonding to the PFPE-DMA layers. The conductivity of the metal electrodes was verified quantitatively by measuring electrical resistance as a function of their aspect ratio. FIG. 12A presents the dependence of the experimentally observed resistance, R, on aspect ratio. For typical aluminum/gold (40 nanometers/100 nanometers) interconnects, the conductivity was observed to be 2.25+/−0.55 10$^7$ S/m, a result comparable to the conductivity predicted using standard values. Upon releasing the electrode array from the fabrication substrate and applying a uniaxial strain of 2%. As illustrated in FIG. 12B, the resistance of interconnects was not observed to change following the application of uniaxial strain. Standard electroplating techniques were applied to coat electrode tips with PEDOT:PSS or platinum black, according to certain embodiments. FIGS. 13A-13B present the specific electrochemical impedance modulus (FIG. 13A) and phase (FIG. 13B), with and without PEDOT:PSS coatings on the electrode tips, as a function of frequency.

Example 8

Figure 14:
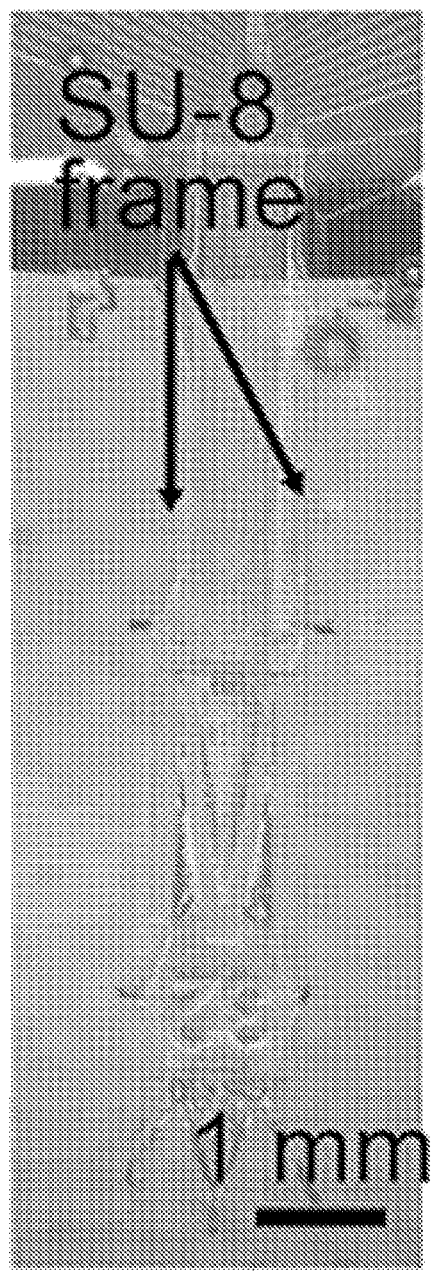
FIG. 14 presents a photograph of a plastic frame used to hold a device, according to certain embodiments.
Figure 15A:
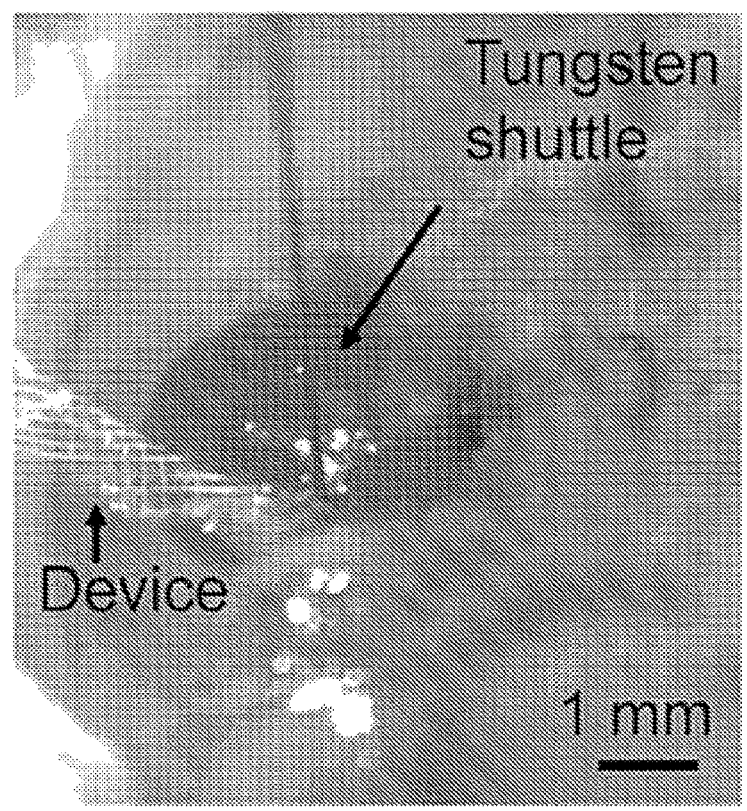
FIGS. 15A-15B present the insertion of a device into the brain of a living, moving mouse, according to certain embodiments.
Figure 15B:
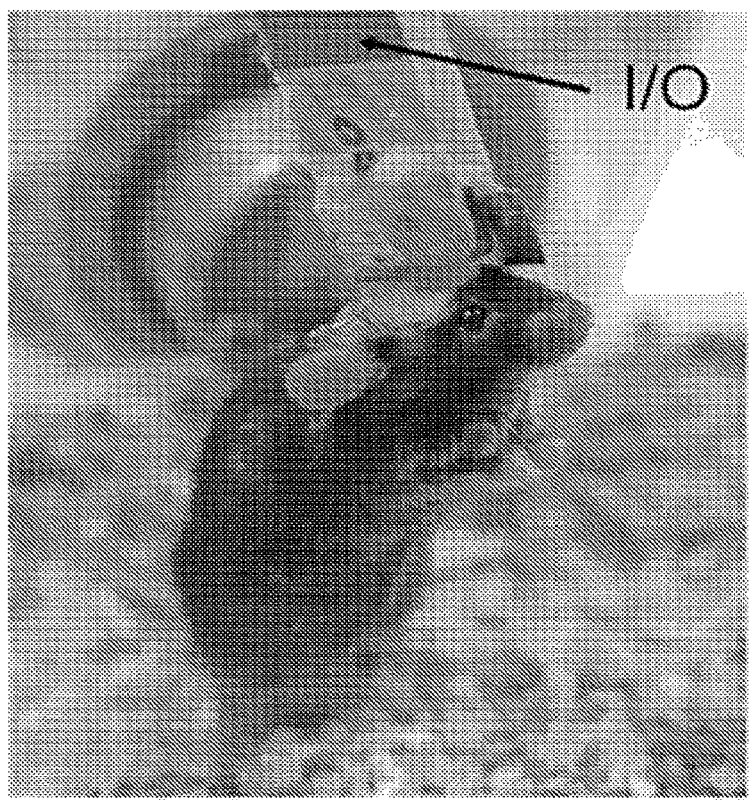

This example demonstrates the successful implantation of brain probes comprising a perfluorinated elastomer. Brain probes were synthesized as previously described. FIG. 14 presents a photograph of a microfabricated plastic frame that was used to hold the devices flat during their release from the substrate. The microfabricated plastic frame was produced as described in Example 5. Next, the microfabricated plastic frame was removed, before implantation. A tungsten shuttle with a 70 micrometer diameter, etched at the tip, was used to guide the perfluorinated elastomer-based brain probe into the brain tissue of a mouse. FIG. 15A is a photograph that shows implantation of the perfluorinated elastomer-based brain probe into the brain tissue of a mouse, according to one embodiment. The shuttle was removed, leaving the device inside the brain tissue of the mouse. FIG. 15B is a photograph of a freely moving mouse with a perfluorinated elastomer-based brain probe implanted into each hemisphere of its brain.

Figure 16A:
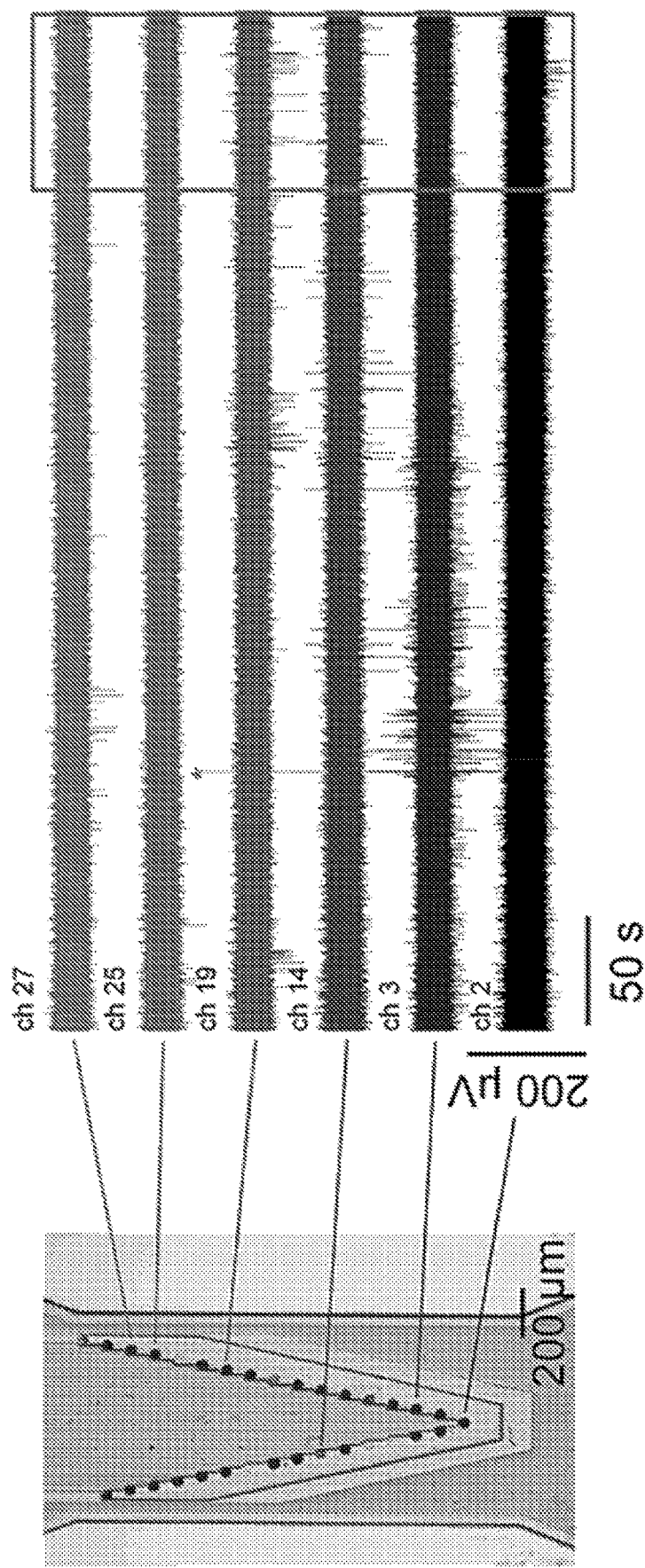
FIGS. 16A-16E present the signal collected from a device implanted into the brain of a living mouse.
Figure 16B:
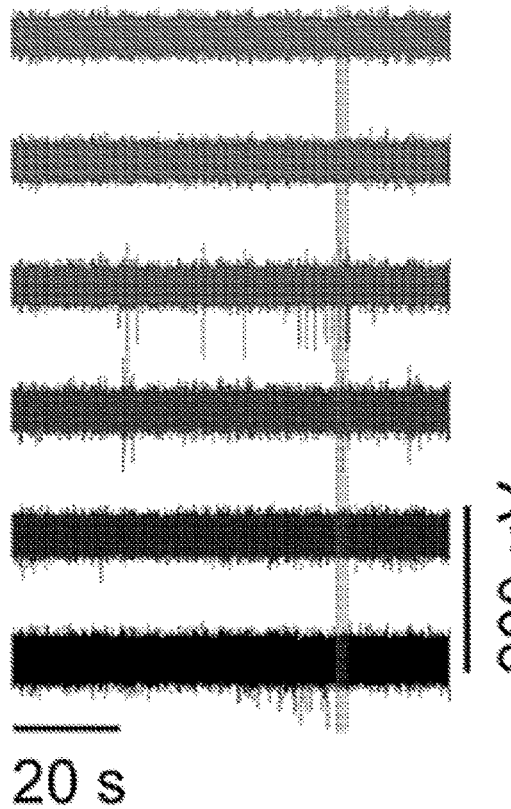
Figure 16C:
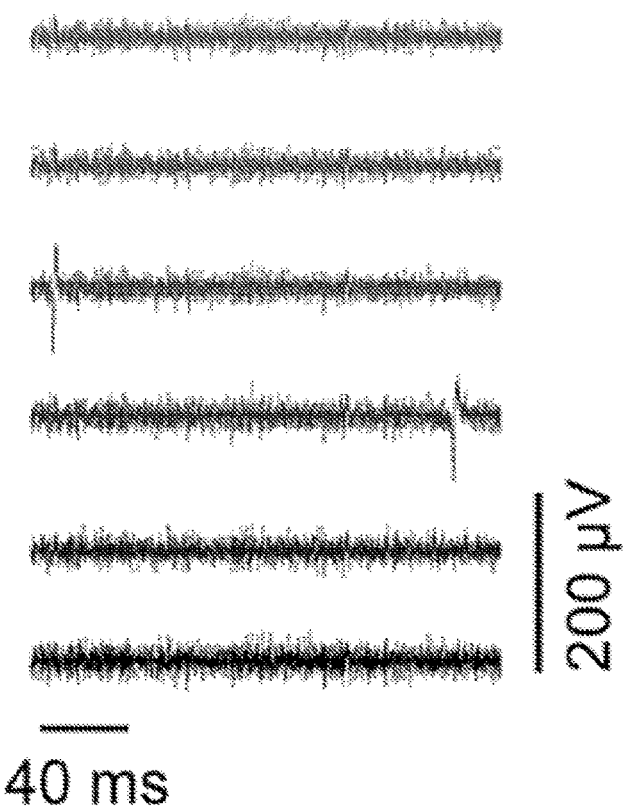
Figure 16D:
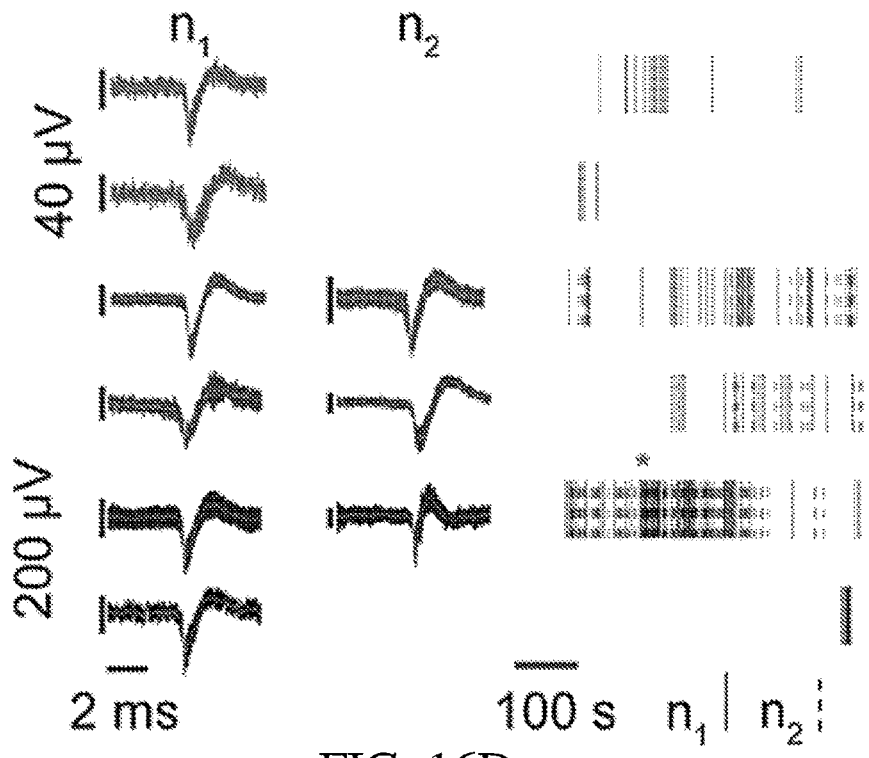
Figure 16E:
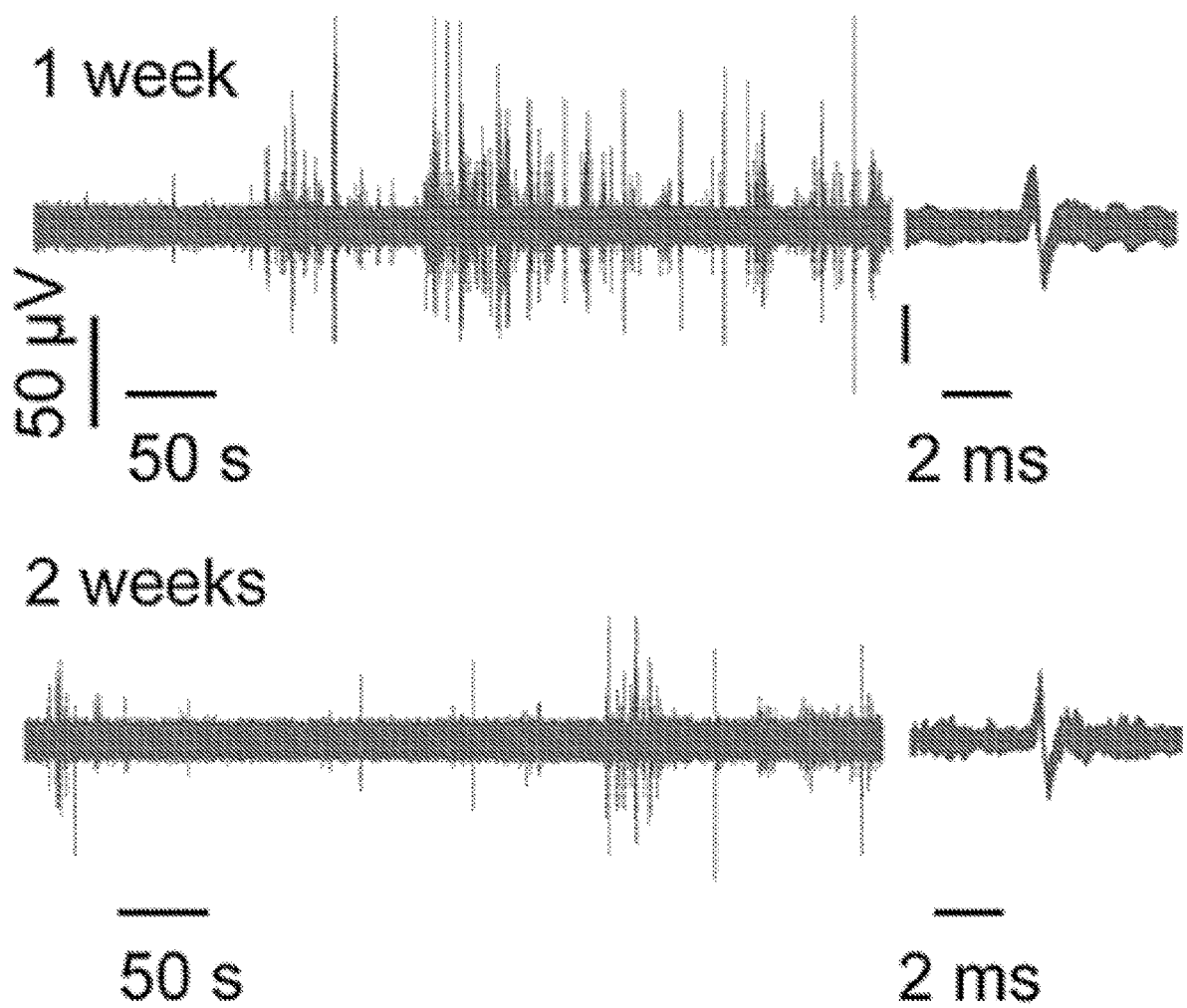

A flat, flexible cable, connected at one end to the device, was interfaced with a voltage amplifier to record electrophysiological data. The neural activity from freely moving mice (such as the mouse of FIG. 15B) was measured at different sites of the devices. A Blackrock Microsystems® Cereplex μ headstage was connected to the flat flexible cable on the head of the mice. A Cereplex™ Direct data acquisition card and the Cereplex software were used to record and filter electrophysiological recordings. FIG. 16A presents exemplary sites of the devices, and illustrates the filtered signals (bandpass filter 300-6000 Hz) show bursting activity on multiple electrodes, recorded 3 days after implantation. FIG. 16B presents an enlargement of the boxed region of FIG. 16A, while FIG. 16C presents an enlargement of the boxed regions of 16C. As illustrated in FIG. 16C, the spikes detected were not synchronous and did not crosstalk between adjacent channels. A custom spike sorting algorithm was used to identify single neuron activity. The threshold for spikes detection was set at five times the standard deviation of the filtered (300-6000 Hz bandpass) time series, and principal component analysis was used for dimension reduction. MATLAB's "kmeans" function was used to cluster the extracted waveforms and to exclude noise artefacts. FIG. 16D presents spike sorting analysis showing the waveforms (left) and raster plots (right) of multiple neurons recorded simultaneously by such brain probe. Meanwhile, FIG. 16E presents evolution of the signal recorded by the same electrode at 1- and 2-weeks post-implantation (left shows the filtered voltage recordings and right shows the average waveform detected). The recorded activity of single neurons was stable after more than two weeks, without qualitative change in the signal-to-noise ratio. Stars in all panels of FIGS. 16A-16E denote voltage artefacts.

Example 9

This example demonstrates preparation of fluorinated polymer precursor solutions of the fluorinated polymers poly(1,1,1,3,3,3-hexafluoroisopropyl acrylate) (PHFIPA) and poly[2-(perfluorohexyl)ethyl]acrylate (PPFHEA). Fluorolink® MD700, a bifunctional PFPE-urethane methacrylate, was obtained from Solvay and used as a crosslinker. 2-Hydroxy-2-methylpropiophenone was used as a photoinitiator. The monomer of each polymer, the crosslinker, and photoinitiator were mixed at a weight ratio of 100/1/0.5 to prepare precursor solutions for spin coating of PHFIPA and PPFHEA. A UV exposure dose (at 365 nm wavelength) of between 100 and 200 mJ/cm$^2$ was used to crosslink PHFIPA and PPFHEA thin films.

Example 10

This example demonstrates the high electrochemical impedance modulus of fluorinated polymer (e.g., perflouoropolyether) layers after prolonged exposure to aqueous salt solutions. This example compares the decrease in measured specific electrochemical impedance modulus of polymers after prolonged immersion in a solution of 10× phosphate buffer solution at 65° C., and is analogous to the tests described under these conditions in Example 4. Layers of fluorinated polymers such as poly(1,1,1,3,3,3-hexafluoroisopropyl acrylate) (PHFIPA), poly[2-(perfluorohexyl)ethyl]acrylate (PPFHEA), and PFPE-DMA were compared to layers of polydimethylsiloxane (PDMS), styrene-ethylene-butylene-styrene (H-SEBS), polyimide (PI), polyisobutylene (PIB), and SU-8 2000.5 epoxy photoresist, which in this example serve as comparisons.

Figure 17A:
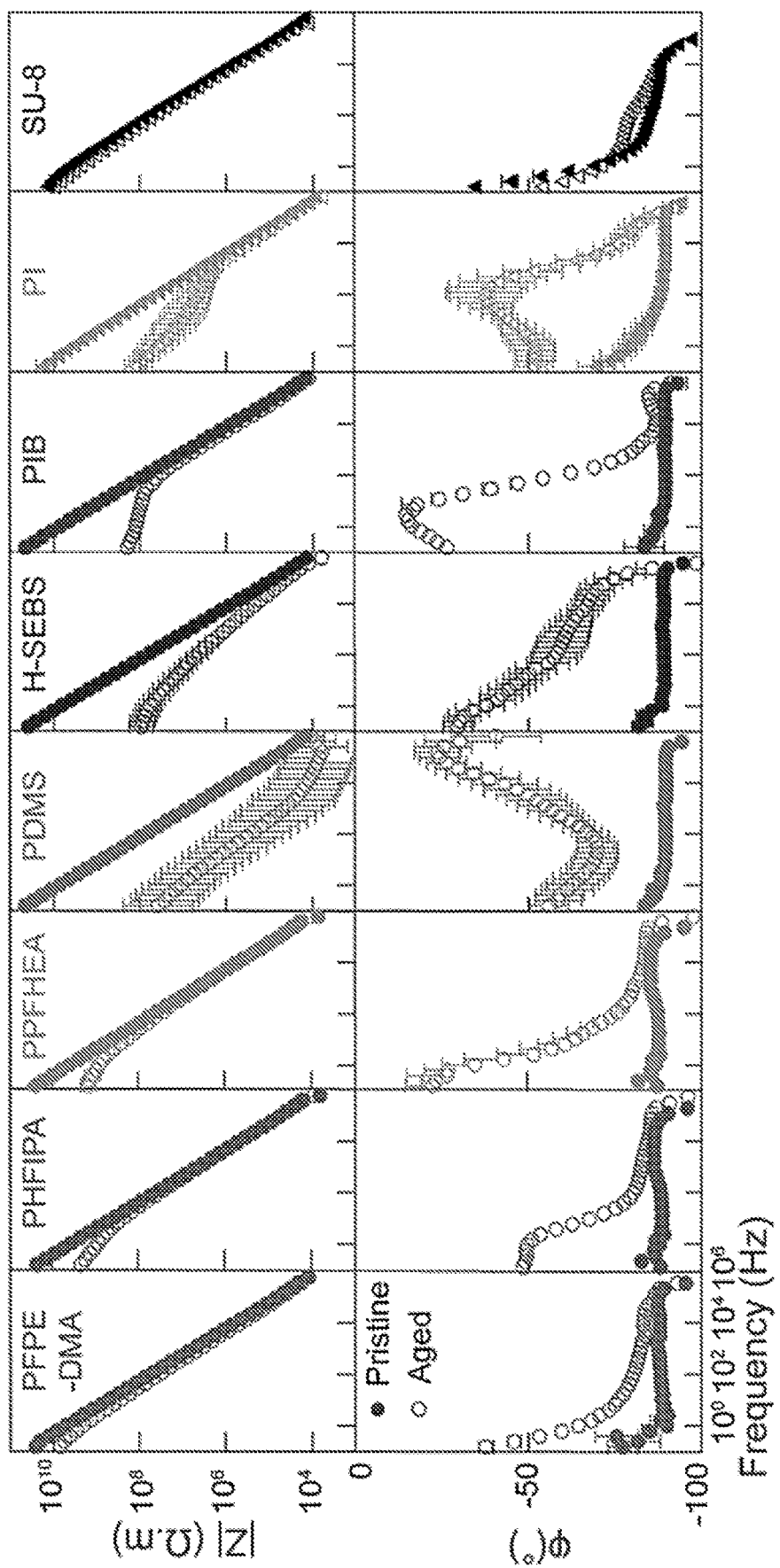
FIGS. 17A-17C present specific electrochemical impedance measurements of polymer films, according to certain embodiments.
Figure 17B:
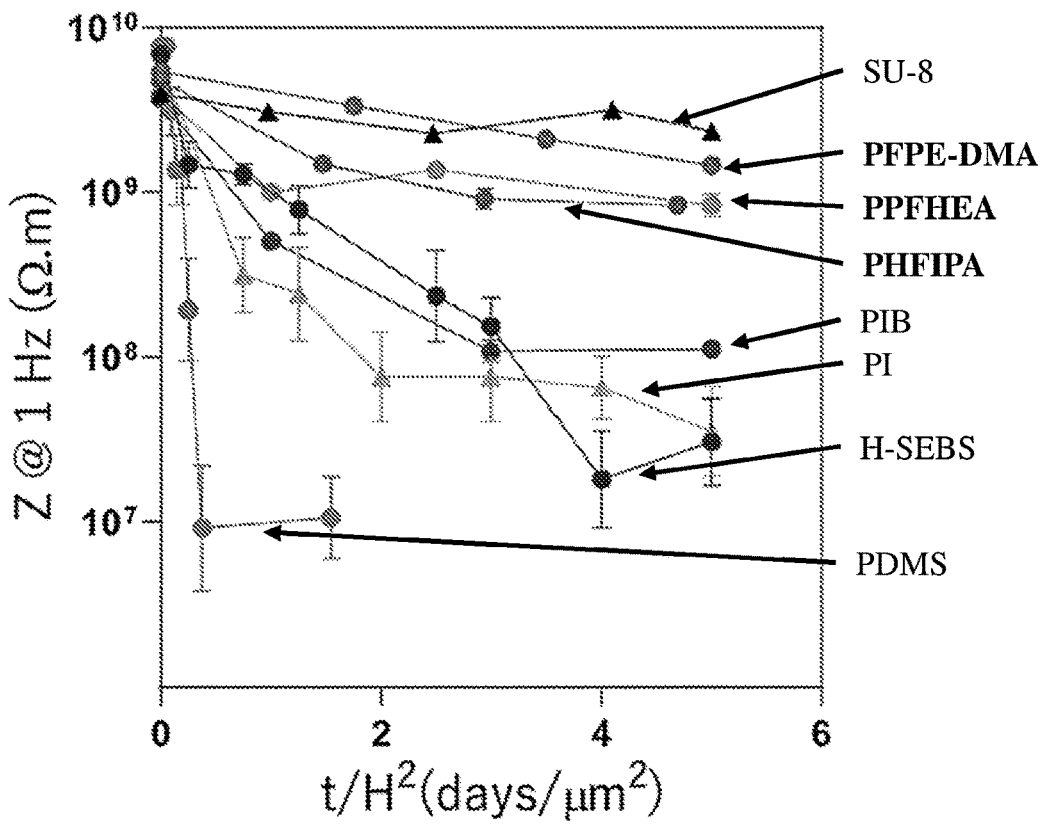
Figure 17C:
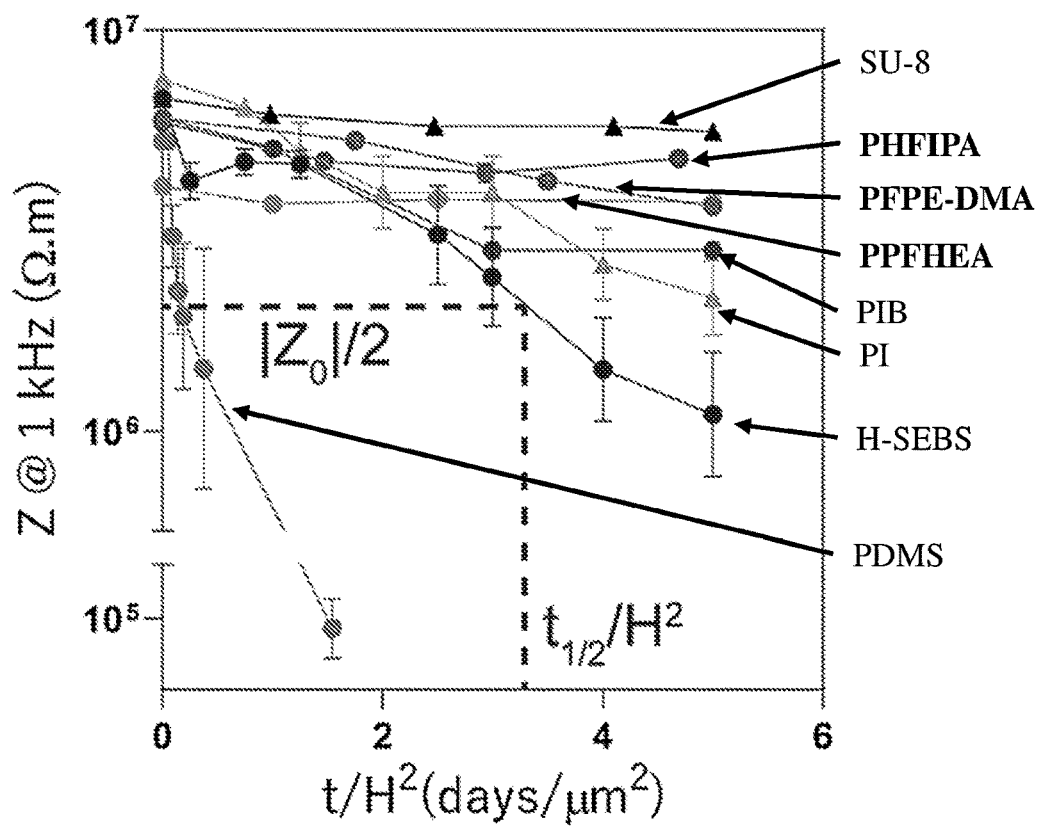

Electrochemical impedance measurements were performed as described above. Polymer layers were immersed under rapid aging conditions at 65° C. in 10× phosphate buffer solution (PBS). FIG. 17A plots the specific electrochemical impedance modulus (top) and phase (bottom) of dielectric polymers under pristine conditions and after aging in 10×PBS at 65° C. (at $t/H^2=5$ days/micrometers$^2$ for PFPE-DMA, PHFIPA, PPFHEA, PDMS, H-SEBS, PI, SU-8 and $t/H^2=1.55$ days/micrometers$^2$ for PDMS). FIGS. 17B and 17C present the specific electrochemical impedance modulus of the immersed layer as a function of time (normalized by $H^2$), determined at 1 kHz and at 1 Hz, respectively. Under rapid aging conditions, all polymers experienced decreases in specific electrochemical impedance modulus. However, the specific electrochemical impedance modulus of the fluorinated polymer layers (PFPE-DMA, PPFHEA, and PHFIPA, labeled in FIGS. 17B-17C in bold), much like the specific electrochemical impedance modulus of the SU-8 layer, decreased very slowly, compared to the specific electrochemical impedance modulus of the other polymers (PIB, PI, H-SEBS, and PDMS). These data demonstrate the long-term stability of fluorinated polymers in general under physiological salt conditions.

Example 11

Figure 18:
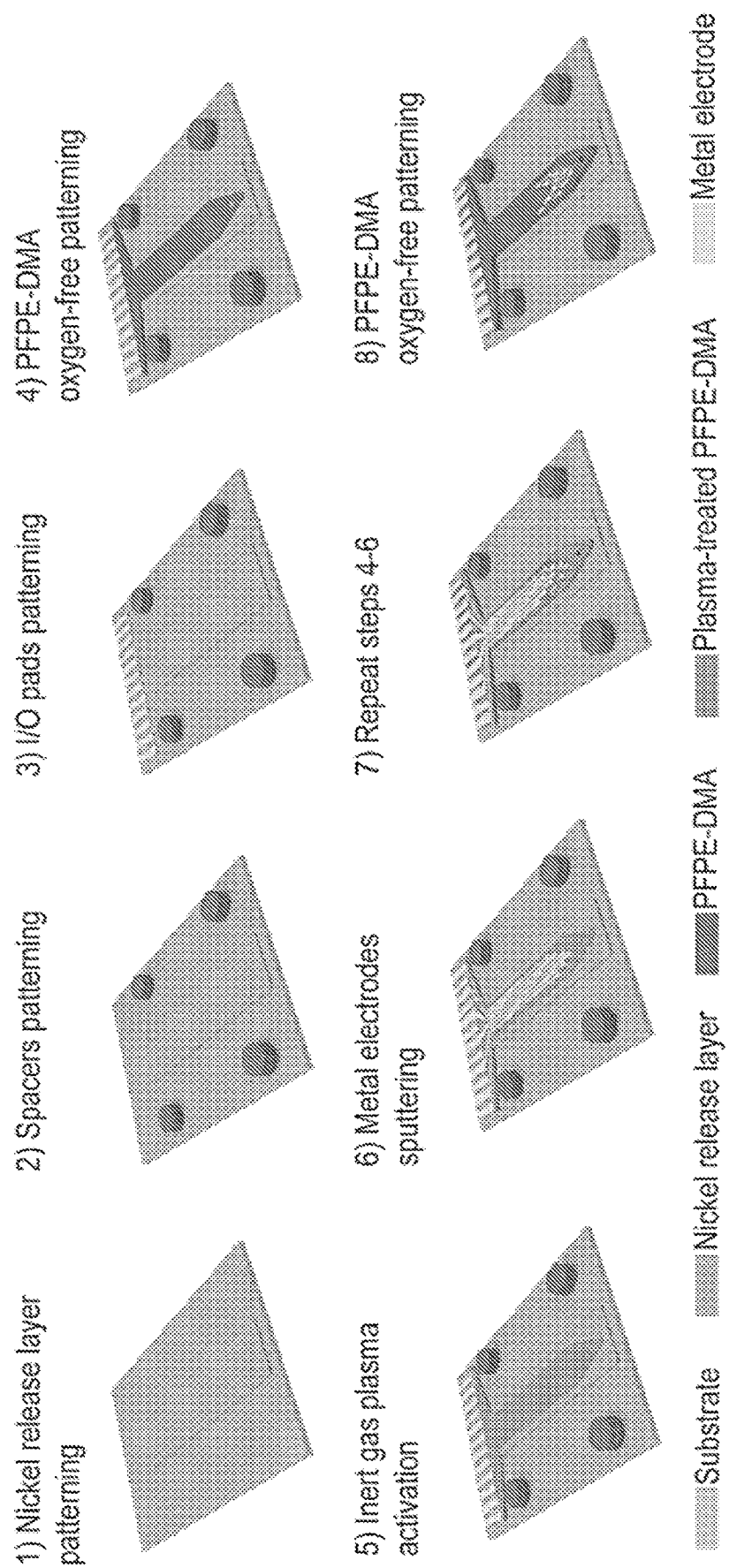
FIG. 18 presents a method of preparing an article comprising a fluorinated polymer, according to certain embodiments.

This example demonstrates an exemplary method of fabricating a brain probe comprising a fluorinated polymer such as a perfluoropolyether, according to certain embodiments. The exemplary method is presented in FIG. 18. The method is similar to the method described in Example 5 above. All photoresist and developers were obtained from MicroChem Corporation unless otherwise mentioned.

1. A 3-inch thermal oxide silicon wafer (from UniversityWafer) was rinsed with acetone, IPA, water and blown dry. Then it was dehydrated at 110° C. for 3 min and treated with 02 plasma at 100 W, 40 sccm 02 for 1 min. Hexamethyldisilazane (HMDS), an adhesion promotor, LOR 3A photoresist, and S1805 photoresist were spin-coated on the wafer at 4000 rpm/s for 1 min. The LOR 3A photoresist was hard-baked at 180° C. for 5 min, after which the S1805 photoresist was applied and hard-baked at 115° C. for 1 min. Then the photoresists were exposed under 40 mJ/cm$^2$ UV light and developed with CD-26 developer for 70 s, rinsed with DI water, and blown dry. After that, a 100 nm Ni layer was deposited on the wafer with a thermal evaporator and lifted off in Remover PG for 3 hours.
2. SU-8 2010 epoxy was used to create spacers. SU-8 2010 was spin-coated on the wafer at 3000 rpm/s for 2 min, and pre-baked at 60° C. for 2 min and 95° C. for 4 min. The SU-8 2010 epoxy was exposed with 170 mJ/cm$^2$ UV light, then post-baked at 60° C. for 2 min and 95° C. for 2 min 30 s. Finally, the SU-8 2010 epoxy was developed in SU-8 developer for 2 min, rinsed with IPA, blown dry and hard baked at 180° C. for 1 hour.
3. Cr/Au (15/100 nm) I/O pads of the brain probe were deposited by e-beam evaporation using the same lift-off method described in step 1.
4. The wafer was firstly cleaned with IPA, water and blown dry. Then PFPE-DMA precursor was spin-coated on the wafer in the range of 2000-6000 rpm/s for 1 min and pre-baked at 115° C. for 2 min to obtain a thickness ranging from 500 nm to 3 μm depending on the rotation speed and precursor concentration. The spincoated PFPE-DMA film was aligned in a photomask aligner and patterned with $10^{-30}$ mJ/cm² UV, using the exemplary, customized nitrogen diffuser described in Example 5. Then the PFPE-DMA was post-baked at 115° C. for 1 min and developed in developer (bis(trifluoromethyl)benzene:1,1,1,3,3-pentafluorobutane in a 1:3 volume ratio) for 1 min and blown dry. $O_2$ plasma was used to clean the pattern. Finally, PFPE-DMA patterns were hard baked at 150° C. for 1 hour.
5. The PFPE-DMA surface was activated with plasma with a power in the range 20-W, 40 sccm Argon flow rate, for 2-6 min.
6. LOR3A photoresist and S1805 photoresist or S1813 photoresist were patterned on the wafer as described in step 1. A subsequent plasma treatment was applied again before metal sputtering. different combinations of metal films such as Al/Au, Al/Au/Al, Al/Au/Pt, Cr/Au, and Cr/Au/Cr were deposited by sputtering, with thicknesses in the range 20-100 nanometers for each layer. Finally, the metal layers were lifted off in Remover PG overnight. To remove lift-off residues, an airbrush gun loaded with remover PG was used.
7. PFPE-DMA was spincoated and UV-cured, followed by plasma surface treatment, lift-off resist patterning, and metal sputtering to create an additional layer of interconnects, as in steps 4-6.
8. Using the method described in step 4, the top PFPE-DMA layer was patterned.
9. (Optional step not shown in FIG. 18). SU-8 2010 (having a thickness that selected based on the total thickness of the brain probe) was used to define a framework for holding the soft brain probe during release. An exemplary plastic frame is described in Example 8, above, with reference to FIG. 14.
10. (Optional step not shown in FIG. 18). To connect the soft brain probes to the recording set-up, isotropic deposition of metal was used to continuously deposit the metal electrodes from PFPE-DMA to a silicon dioxide substrate, which allowed for standard flip chip bonding of flexible cables.

Example 12

Figure 19:
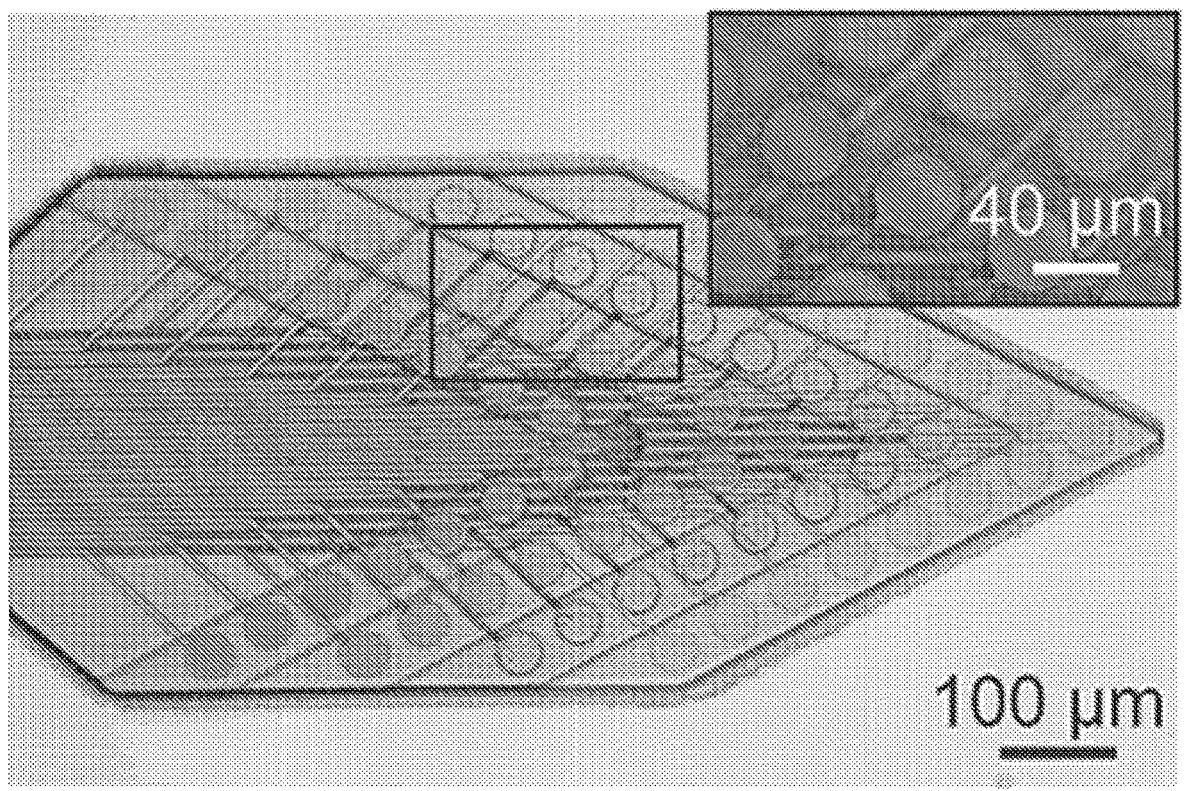
FIG. 19 presents an image of an exemplary article designed for use as a neural sensor, according to certain embodiments.

This example demonstrates the properties of an exemplary brain probe fabricated using the method of Example 9. FIG. 19 presents a bright-field (BF) optical image showing an exemplary brain probe comprising six layers of PFPE-DMA sandwiching four layers of exemplary metal electrodes. The inset of FIG. 19 presents the electrodes in greater detail. The lateral resolution of this exemplary brain probe was approximately 1 micron for PFPE-DMA features, with controllable thickness in the range of 0.3-3 microns. Focused ion beam (FIB)-milled SEM of a cross-section of the exemplary brain probe showed no delamination among PFPE-DMA and metal layers, even after a uniaxial stretch to 20% elongation.

The brain probe was then chip-bonded to connect it to a recording set-up. After chip bonding, standard electroplating techniques were used to coat electrode tips with PEDOT:PSS or Pt Black to verify the conductivity of the electrodes. An SP-150 potentiostat from Bio-logic along with its commercial software EC-lab in voltage or current control was used for electrodeposition. Electrodes from brain probes were connected to the working electrode. A platinum wire immersed in the precursor solution was used as the counter electrode, which also serves as the voltage reference. For Platinum black deposition, the precursor solution consists of 1 mM chloroplatinic acid solution and 25 mM sodium nitrate. Cyclic voltammetry with a potential varying from −1.0V to 0.2V at 0.05 V/s for $10^{-15}$ cycles was used. For PEDOT-PSS deposition, an electrolyte consisting of 0.01 M PEDOT (Sigma-Aldrich, USA) and 0.1 M sodium PSS (Sigma-Aldrich, USA) aqueous solution was used. The electrochemically polymerized reaction was performed under constant voltage conditions. In the constant voltage mode, the polymerization was carried out under a constant current of 1 V for 30 s.

Figure 20:
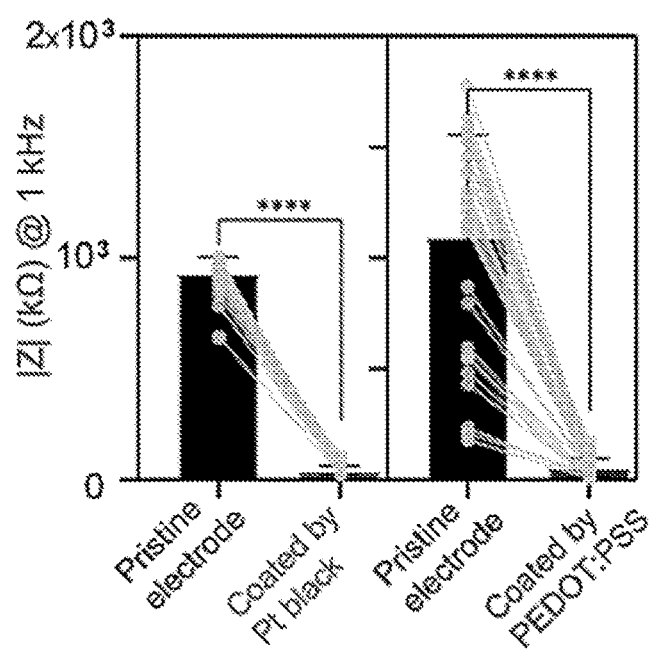
FIG. 20 presents a change in electrochemical impedance modulus of an electrode upon coating with conductive materials, according to some embodiments.

FIG. 20 presents the change in the impedance modulus at 1 kHz before and after PEDOT:PSS and Pt black electroplating for 40-μm-diameter electrodes of brain probes (n=32, bar plots show mean±S.D.). In both cases, P<0.0001 for the two-tailed, paired t-test, showing that coating by PEDOT:PSS or Pt Black caused a significant drop in impedance, indicating proper function of the contact.

Figure 21:
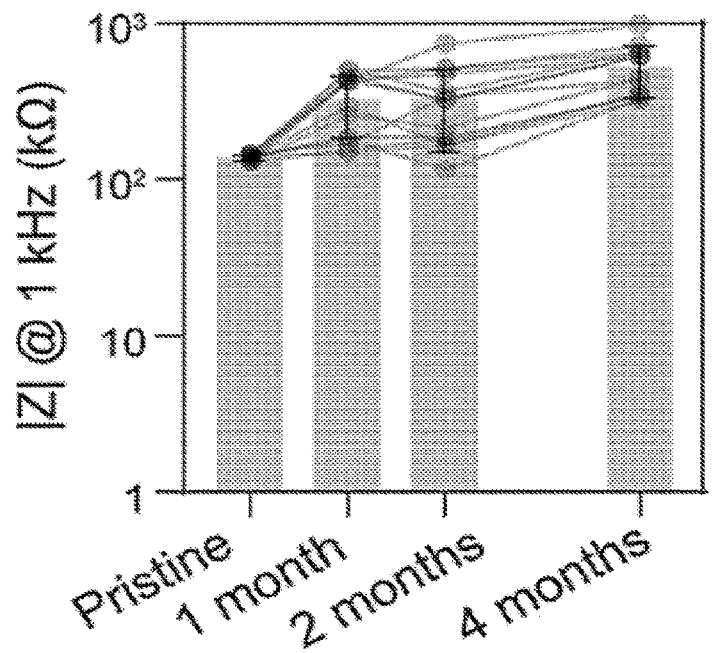
FIG. 21 presents the change in electrochemical impedance modulus of polymers on exemplary electrodes over time, according to some embodiments.

Impedance of sputtered Al/Au interconnects and Pt electrodes was measured over time to confirm the stability of the exemplary brain probes. The results are presented in FIG. 21, and as shown, the exemplary brain probes did not experience a large change in impedance over time. The stability of the impedance of the interconnects demonstrates the long-term stability of the electrodes.

Figure 22:
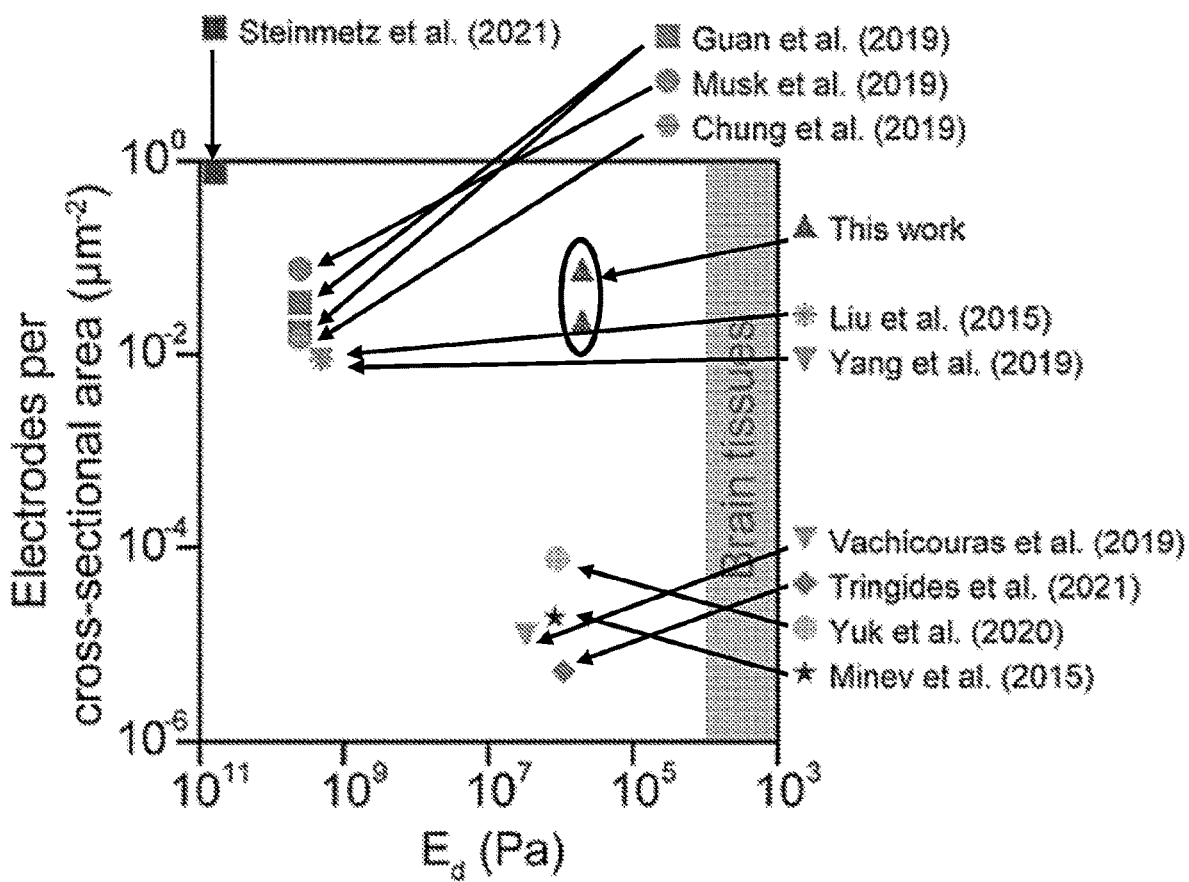
FIG. 22 compares electrode number density and elastic modulus for various neural sensors, with neural sensors prepared according to the embodiments described herein, according to some embodiments.

The elastic modulus of the exemplary brain probes was determined, and the exemplary brain probes were compared against other, state-of-the-art brain probes in terms of their elastic modulus ($E_d$) and their electrode number density (the number of electrodes created per square micron of the brain probe). FIG. 22 illustrates the comparison of the elastic modulus and the electrode number density of the brain probes, and illustrates the elastic modulus of typical brain tissues as a shaded region. As shown in FIG. 22, the exemplary electrodes described herein had the lowest elastic modulus of all the brain probes. Furthermore, the exemplary brain probes described herein had a 100× higher electrode number density, relative to state-of-the-art electrodes with a similar elastic modulus. The elastic modulus of the exemplary brain probes described herein was approximately 1000× lower than the elastic modulus of state-of-the-art brain probes having a similar electrode number density. The ratio between the electrode number density and the elastic modulus of the exemplary brain probes described herein exceeded $10^{-8}$ electrodes/micron²-Pa. In contrast, the state-of-the-art brain probes had a ratio between the electrode number density and the elastic modulus of the exemplary brain probes of between $10^{-12}$ electrodes/micron²-Pa and $10^{-10}$ electrodes/micron²-Pa. This demonstrates that the exemplary brain probes described herein achieved both superior mechanical properties and a high sensor density, relative to other state-of-the-art brain probes.

Example 13

Figure 23:
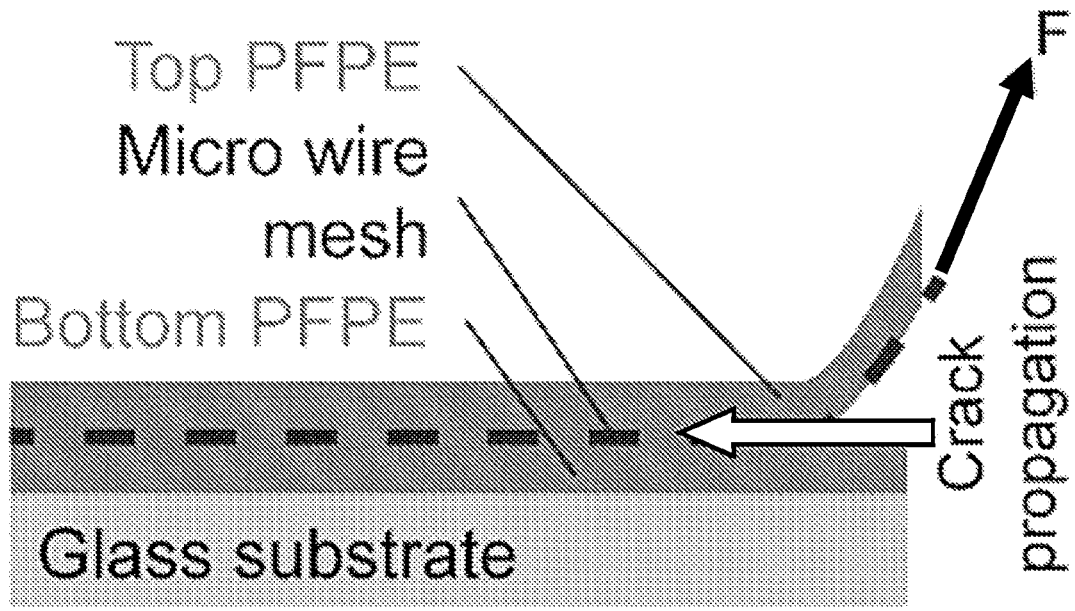
FIG. 23 presents a schematic illustration of an exemplary peel test, according to some embodiments.
Figure 24:
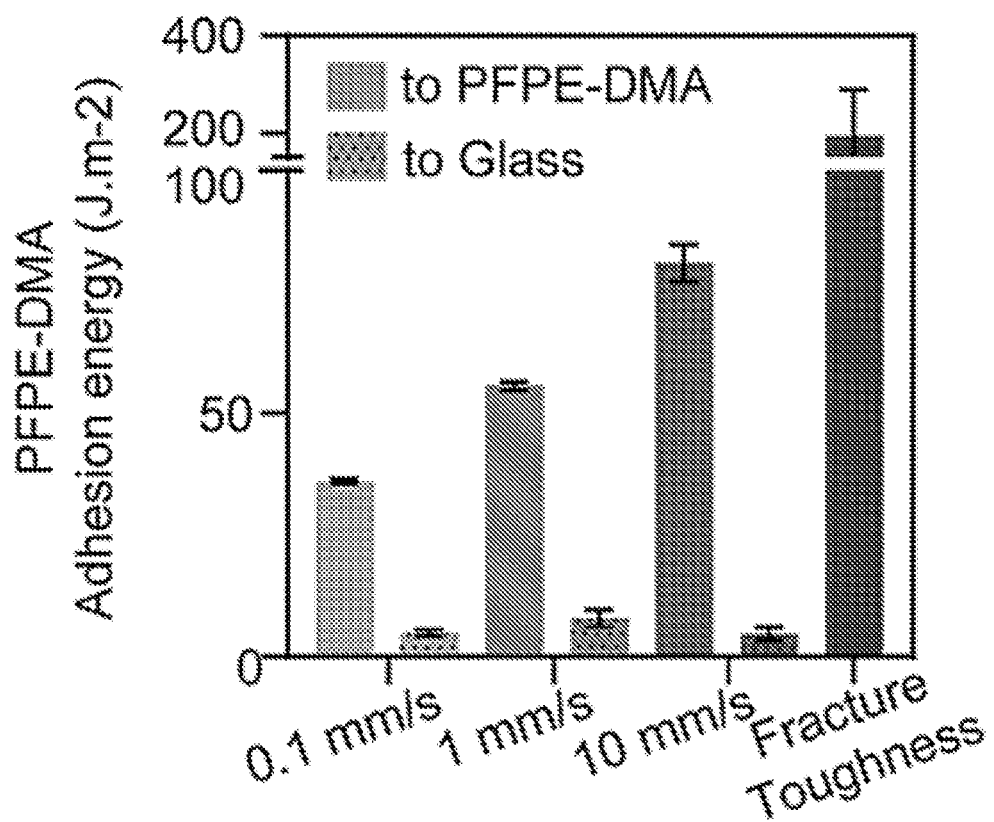
FIG. 24 presents adhesion energy of polymer layers at various peel rates, according to certain embodiments.

In this example, the adhesion energy between two exemplary layers of PFPE-DMA joined by the method of Example 9 was measured by using a 900 peel test, performed at peel rates of 0.1 mm/s, 1 mm/s, and 10 mm/s. FIG. 23 presents a schematic illustration of the peel test, and FIG. 24 illustrates the adhesion energy of a top PFPE-DMA layer to a bottom layer of PFPE-DMA or, as a comparison, to glass. The fracture toughness of PFPE-DMA is also reported in FIG. 24. As shown in FIG. 24, the self-adhesion energy of PFPE-DMA layers substantially exceeded the adhesion energy to the glass substrate (36.0±0.5 J/m$^2$ and 4.9±0.7 J/m$^2$, respectively, at a peeling rate of 0.1 mm/s), and is closer to the intrinsic fracture toughness of the two layers (measured to be 128 J/m$^2$ and 261 J/m$^2$), indicating that the two PFPE-DMA layers strongly adhered and did not easily delaminate under strain.

Example 14

Figure 25:
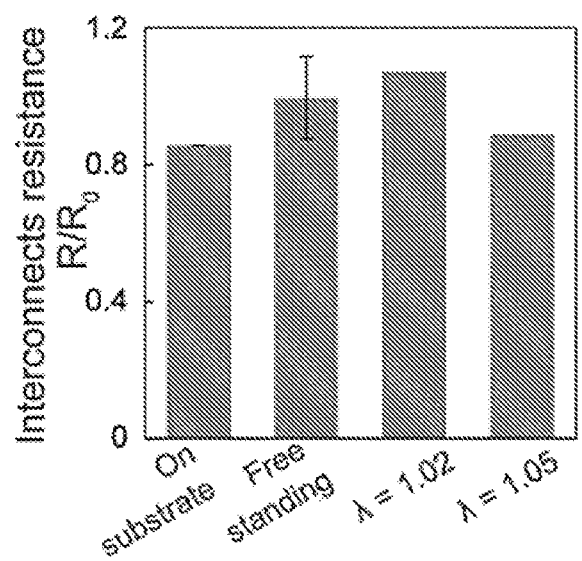
FIG. 25 presents interconnects resistance of an exemplary brain probe, according to certain embodiments.

In this example, the interconnect resistance of exemplary brain probes was measured on the substrate, as well as in a free-standing configuration in unstrained and uniaxially strained conditions. FIG. 25 illustrates the interconnect resist of each brain probe on the substrate, after releasing the brain probe from the substrate, and at a 2% (λ=1.02) and a 5% (λ=1.05) uniaxial stretch. As illustrated, the interconnect resistance was consistent under all conditions, and remained high, even at 5% strain.

Example 15

In this example, finite element analysis (FEA) was used to model exemplary brain probes to understand their mechanical properties. Abaqus 6.12 software was used to analyze the mechanical properties of different polymer brain probes. The goal of the simulations was to evaluate strain and stress concentration of composite beams bending around a capillary of circular cross-section under gravity. The brain probes were modeled using three layers: a 140 nm thick central metal layer between two 4.5 micron thick dielectric layers with the elastic modulus of PFPE-DMA or SU-8. The elements used were S4R5 or S4R, with a mesh size of 50 microns, and a contact between the probes and the capillary modelled by surface-to-surface normal forces only (shear-free contact).

Multilayer devices encapsulated by dielectric elastomers are more flexible than devices made with plastic dielectric materials. Comparing 9-μm-thick PFPE-DMA with SU-8 brain probes that contain 100-nm-thick metal interconnects layers (Extended Data FIG. 8a-c), PFPE-based brain probes exhibit substantially higher flexibility. Finite element analysis confirms the difference in the flexibility due to the different elastic modulus between elastomeric and rigid dielectric materials. The dielectric elastomer negligibly contributes to the load-carrying capacity so that the metal layers become the principal load-carrying members. As a result, a simple beam model shows that this design decreases the flexural rigidity of the brain probe by 4 orders of magnitude (Extended Data FIG. 8b-d).

Finite element analysis further showed that the strain concentration (~0.003) in the central metal layer remains well below the yield strain of Au when one-metal layer, 9 μm-thick PFPE-DMA brain probes bend around a 1 mm-diameter capillary under gravity. This simulation result demonstrated that metal interconnects would not undergo plastic deformation or fracture when the soft brain probes are bent. The adhesion of the metal lines to the elastomer was also sufficient to generate wrinkles patterns, a feature commonly observed in laminates comprising stiff islands of material on soft substrate, where larger strains can be accommodated before failure of the stiff layer compared to the free-standing fracture strain. This result can further explain why metal connections of the exemplary brain probes described herein remained highly conductive after 5% of uniaxial strain.

Figure 26:
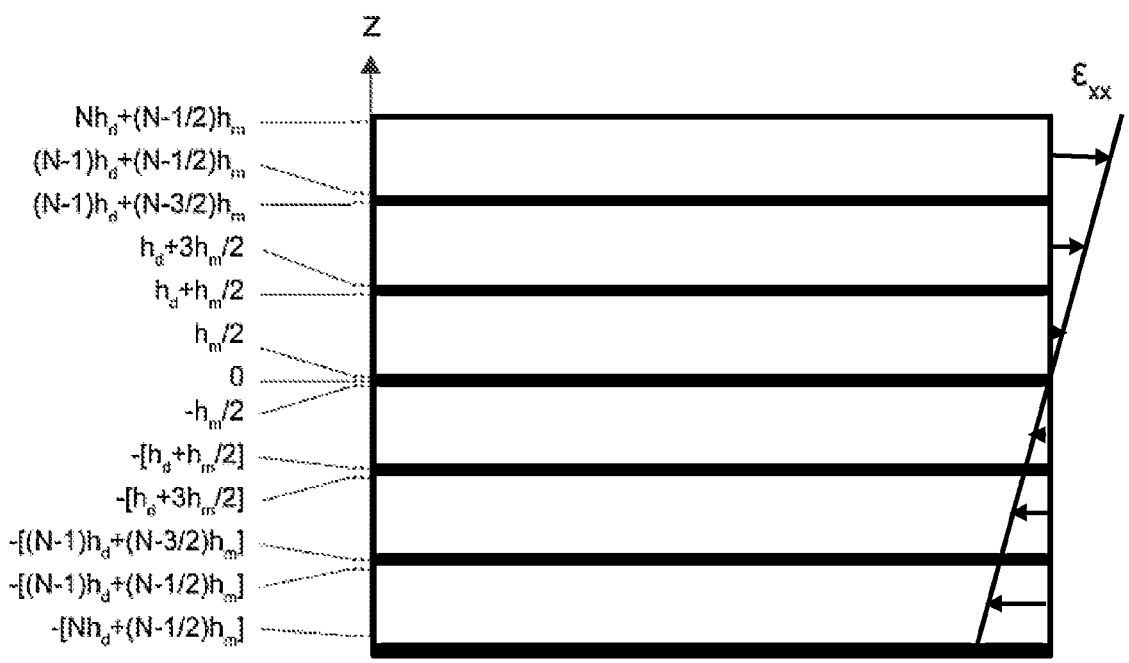
FIG. 26 presents a schematic, cross-sectional illustration of a multi-layered article, according to certain embodiments.

Because brain probes in general can be multi-layered, a multi-layered composite model was then evaluated to model multi-layered models of various thickness. FIG. 26 presents a composite beam model of a brain probe with 2N−1 layers of metal interconnects. Layers of the same material are assumed to have the same thickness. The variables $h_d$ and $h_m$ respectively denote the dielectric encapsulation layer thickness and the metal layer thickness. For the purposes of the model, the values of the layer thicknesses were chosen to be $h_d$=2 microns and $h_m$=40 nm. As illustrated, the strain $\varepsilon_{xx}$ varies throughout the composite beam. The elastic modulus and Poisson ratio of the metal were given realistic values of $E_{metal}$=79 GPa and $v_{metal}$=0.22, respectively. For modeling the composite beam comprising a stiff plastic (e.g., SU-8), the values $E_{plastic}$=4 GPa and $v_{plastic}$=0.33 were chosen as realistic estimates of the elastic modulus and the Poisson ratio, respectively. For modeling the rigid composite beam comprising the elastomer, realistic values of $E_{elastomer}$=0.5 MPa and $v_{elastomer}$=0.5, were chosen for the elastic modulus and the Poisson ratio, respectively.

Figure 27:
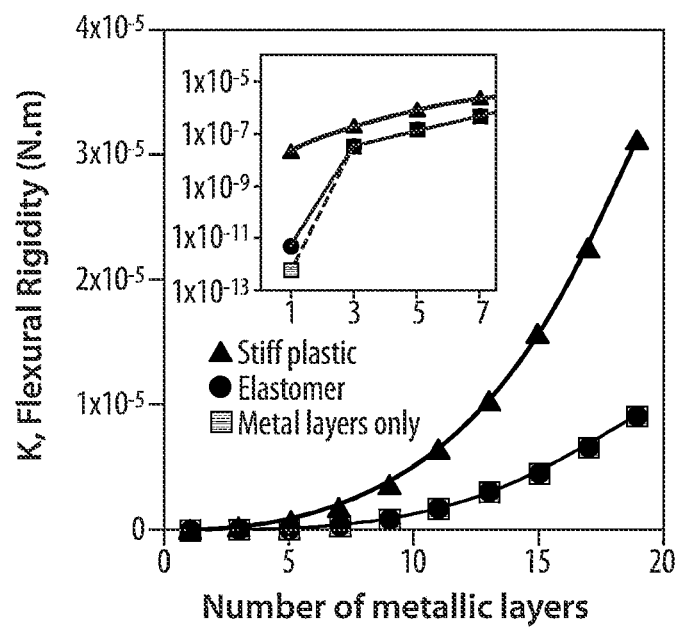
FIG. 27 presents exemplary flexural rigidity of simulated multi-layered articles, according to certain embodiments.
Figure 28:
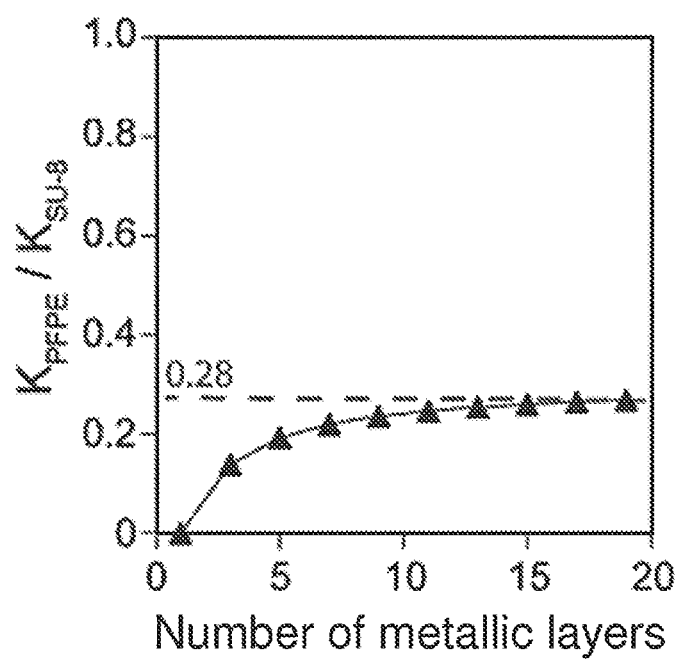
FIG. 28 presents a ratio between flexural rigidity of different, exemplary multi-layered articles as a function of number of metallic layers, according to certain embodiments.

The flexural rigidity of the composite beam was estimated as a function of the number of layers of the composite beam. FIG. 27 presents the results, demonstrating that the stiff plastic beam had a much higher flexural rigidity than the elastomeric beam. As indicated in the figure, as the number of metal layers increased, the flexural rigidity of the elastomeric composite beam approached the flexural rigidity that would be expected of the layers of metal alone, indicating that the flexural rigidity of thick brain probes would be limited by the flexural rigidity of the metallic layers, rather than the flexural rigidity of polymeric layers. FIG. 28 presents the ratio between the flexural rigidity of the stiff plastic beam and the elastomeric beam as a function of the number of metallic layers. As the number of metal layers increased, the ratio between the flexural rigidity of the stiff plastic composite beam and the elastomeric composite beam approached an asymptotic limit of 0.28, resulting from the contribution of the metallic layers to the flexural rigidity of both composite beams.

Example 16

Figure 29A:
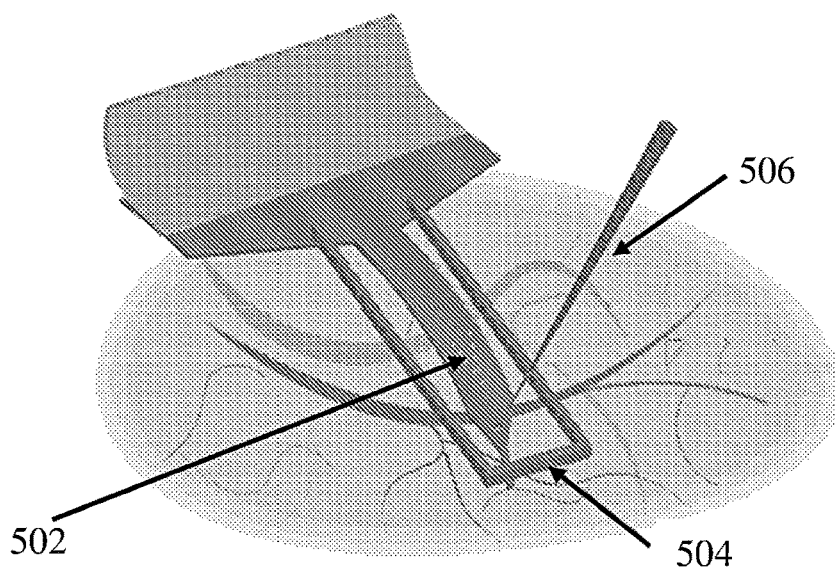
FIGS. 29A-29B present implantation of a substrate of an exemplary neural sensor, according to some embodiments.
Figure 29B:
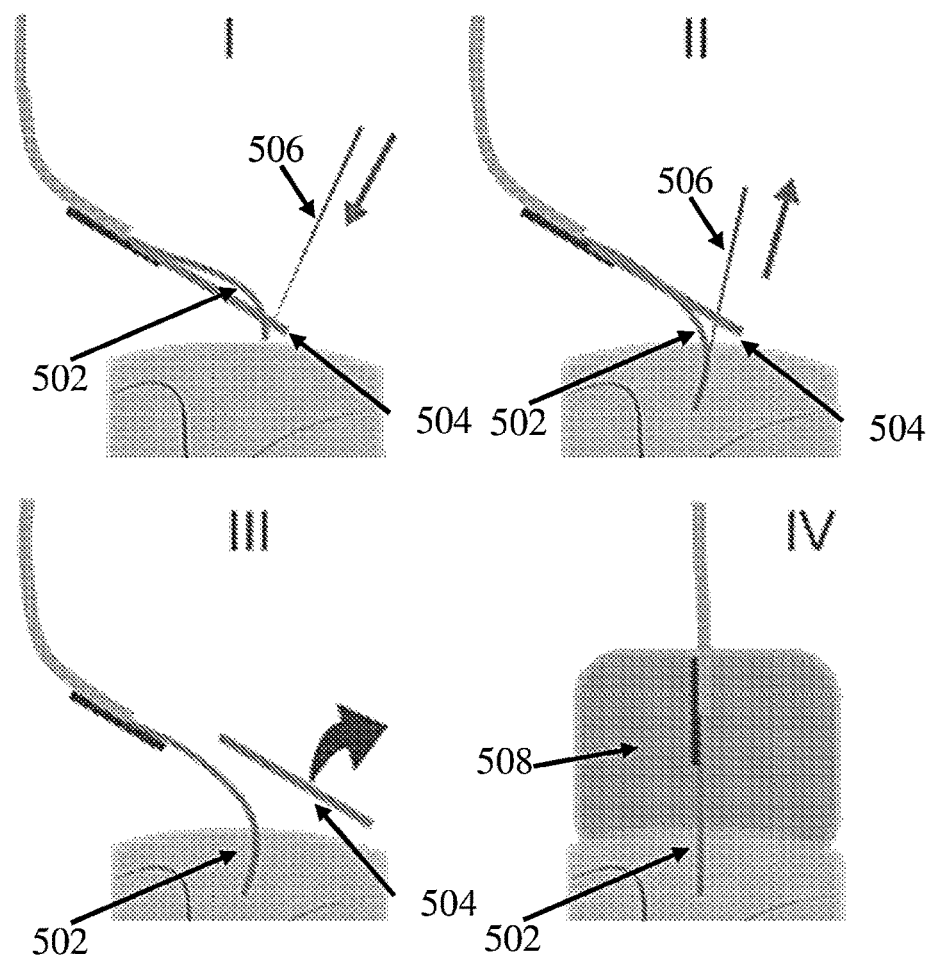

This example illustrates a method of transferring and aligning an exemplary brain probe using an exemplary frame of the type described in previous examples. FIG. 29A presents a perspective schematic illustration of an exemplary brain probe 502 in exemplary frame 504, according to some embodiments. Also shown is a shuttle 506 (in this case a tungsten shuttle), which was used to apply the exemplary brain probe. FIG. 29B presents side-view schematic illustrations of an exemplary method of inserting a brain probe. In step I, shuttle 506 was used to insert brain probe 502 into brain tissue, while frame 504 held brain probe 502 in place. In step II, the shuttle was removed. In step III, frame 504 was removed from brain probe 502, which remained in the brain tissue. Finally, in step IV, dental cement 508 was applied to seal brain probe 502 in position while allowing communication between the brain probe and the recording setup. This method allowed implantation of the exemplary brain probes of Example 12 into the brains of mice. The soft probes were implanted in the somatosensory cortex region and connected via a flat flexible cable to a voltage amplifier for electrophysiological recording, described in greater detail below.

Example 17

Figure 30:
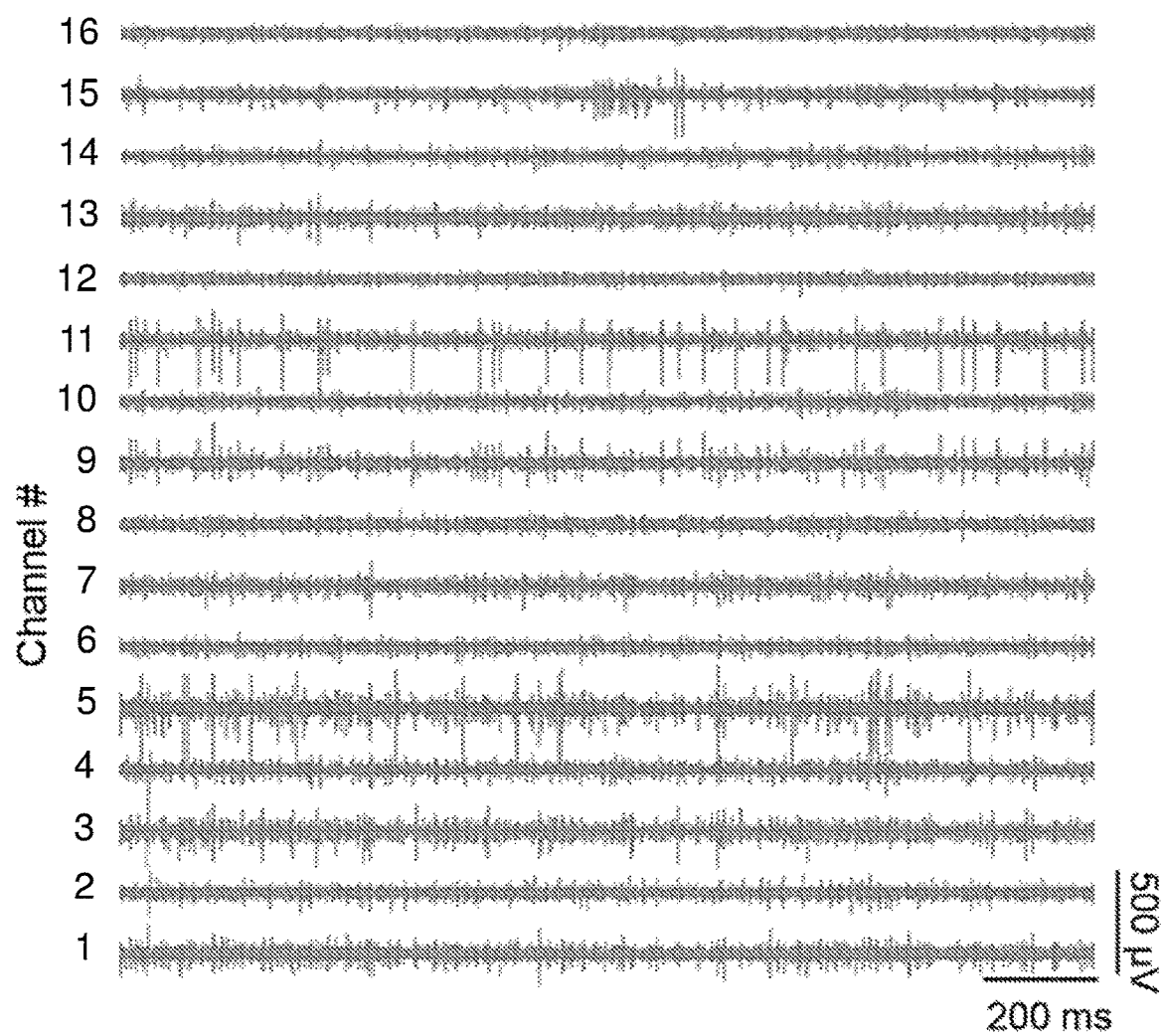
FIG. 30 presents exemplary measurements using a plurality of exemplary electrodes implanted in the brain of a subject, according to some embodiments.
Figure 31:
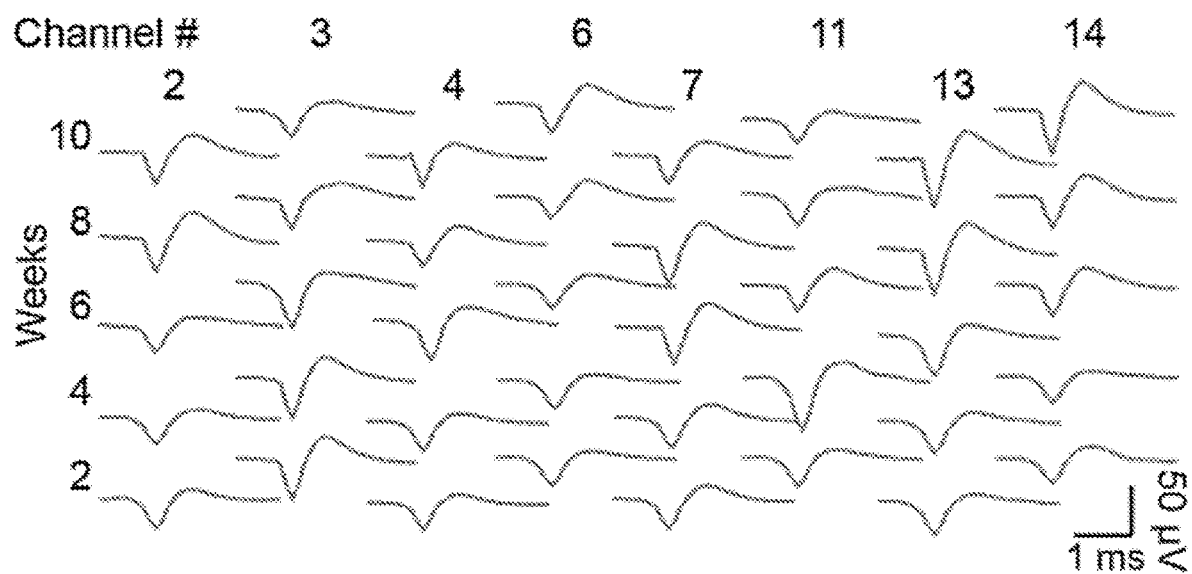
FIG. 31 presents exemplary results of spike sorting analysis performed on measurements made using a plurality of exemplary electrodes implanted in the brain of a subject, according to some embodiments.
Figure 32:
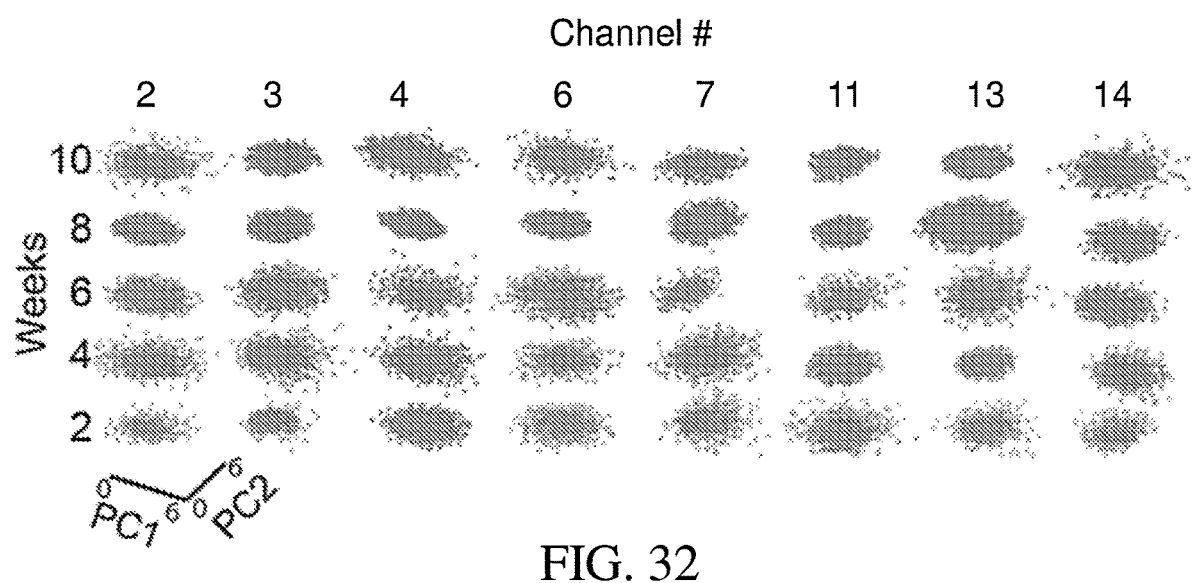
FIG. 32 presents exemplary mapping of measurements using a plurality of exemplary electrodes, wherein the measurements are represented according in a principal component space, according to certain embodiments.

This example demonstrates implantation of an exemplary brain probe into a mouse brain and subsequent measurement of brain activity. Brain probes were inserted according to the methods described in Examples 8 and 16. FIG. 30 shows representative spontaneous activity from 16-channel PFPE-DMA at 1-month post-implantation. Spike sorting analysis was used to analyze the data in 2 week intervals. FIG. 31 shows the results of spike sorting analysis, illustrating the average waveforms of representative single-unit action potentials. The recorded activity of the single unit is stable over 10-week post-implantation, with little to no changes in the waveform shape and interspike interval over the entire period. Principal component analysis (PCA) further demonstrated brain probe stability, and demonstrated that all units exhibited nearly constant positions in the first and second principal component plane (PC1-PC2) from 2 through 10 weeks post-implantation. This is illustrated in FIG. 32, which shows the unit positions of several channels in the PC1-PC2 plane associated with the channels and times of FIG. 32.

Figure 33A:
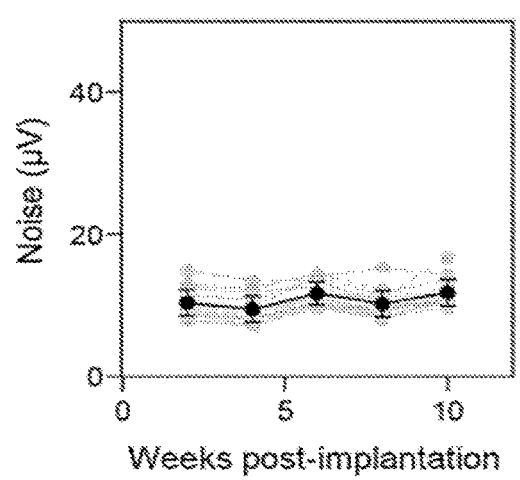
FIG. 33A presents average noise associated with the electrodes over a period of 10 weeks following implantation of an exemplary sensor into a brain of a subject, according to certain embodiments.
Figure 33B:
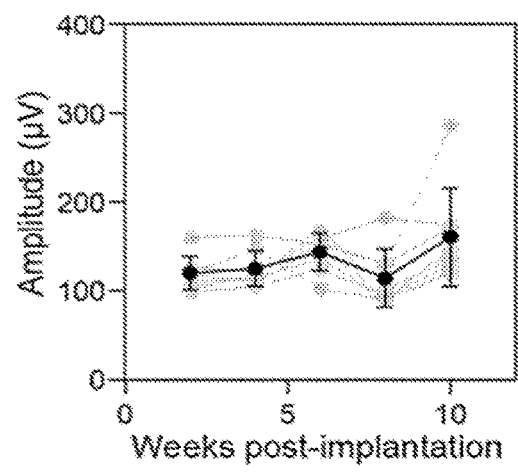
FIG. 33B presents the spike amplitude averaged over all channels of an electrode over a period of 10 weeks following implantation of an exemplary sensor into a brain of a subject, according to certain embodiments.

FIG. 33A presents noise level averaged over all channels, which was low and nearly constant post-implantation. (The noise was 10.4±1.8 µV at 2-week post-implantation and 11.8±1.8 µV at 10-week post-implantation for the n=16 electrodes, as shown in FIG. 33A.) FIG. 33B presents the spike amplitude averaged over all channels, which slightly increased after 10 weeks post-implantation, principally as a result of activity in a single channel. (The spike amplitude was 119.7±19.2 µV at 2-week post-implantation and 160.6±55.3 µV at 10-week post-implantation for n=8 units). These results demonstrate that the brain probe operated as intended, without substantial degradation over the 10 week period.

Finally, to test the immune response from the scalable brain probe, the mouse immune response to exemplary implanted 9-micron-thick PFPE-DMA and SU-8 brain probes, capable of incorporating at least 4-8 layers of electrodes in mouse brains, were studied. Immunohistology of brain slices was performed at 2, 6, and 12 weeks post-implantation to evaluate the immune response reaction to the implanted brain probes. SU-8 probes with the same dimension were implanted as control (n=4 mice per time point).

Immunohistochemistry and confocal fluorescence imaging were performed. At each time point (2, 6, and 12 weeks post-implantation), mice were anesthetized with 40-50 mg/kg sodium pentobarbital and then transcardially perfused with 40 mL 1×PBS and 40 ml 4% paraformaldehyde, followed by decapitation. The brains implanted with the exemplary brain probes were removed from the cranium and postfixed in paraformaldehyde for 24 h at 4° C. The brains were transferred to sucrose solutions (stepwise increase of concentration from 10% to 30%, w/v) until they sunk to the bottom. The samples were embedded in optimal cutting temperature (OCT) compound and a cryostat sectioned slices having a thickness of 30 microns. Brain implanted with SU-8 brain probes with the same thickness were used as a comparison.

Brain slices were first incubated with primary antibodies: NeuN (targeting nuclei of neurons, 1:200, Abcam #ab177487, USA), GFAP (targeting astrocytes, 1:200, Abcam #ab4674, USA), and IBA1 (targeting microglia, 1:100, Abcam #ab5076, USA) at 4° C. overnight. After washing three times with 1×PBS, the brain slices were incubated with secondary antibodies at room temperature for 3-4 hrs. Brain slices were stained by 4',6-diamidino phenylindole 8 (DAPI) for 10 minutes. Finally, after washing by 1×PBS, all samples were imaged using Leica TCS SP8 confocal microscopy.

Images at 2, 6, and 12 weeks post-implantation showed that there was a significant enhancement in NeuN (neuron) signal around PFPE-DMA probes compared to SU-8 probes ($p<0.05$, n=4, two-tailed unpaired t test). Specifically, the NeuN intensity increased to the endogenous level at 12-week post-implantation (92.7±14.0% vs. 61.6±16.9%, mean±SD, n=4), indicating high biocompatibility of the PFPE-DMA probe. The fluorescence intensity of astrocytes and microglia at 12 weeks post-implantation showed a significant reduction around the exemplary PFPE-DMA brain probe compared to SU-8 probe (GFAP: 111.7±27.7% vs. 303.7±62.6%, Iba-1: 15.5±24.6% vs. 156.4±21.7%, mean±S.D., n=4). These results demonstrated the high biocompatibility of PFPE-DMA dielectric elastomers as well as their ability to further increase the density of electrodes for chronic brain implantation.

Figure 34:
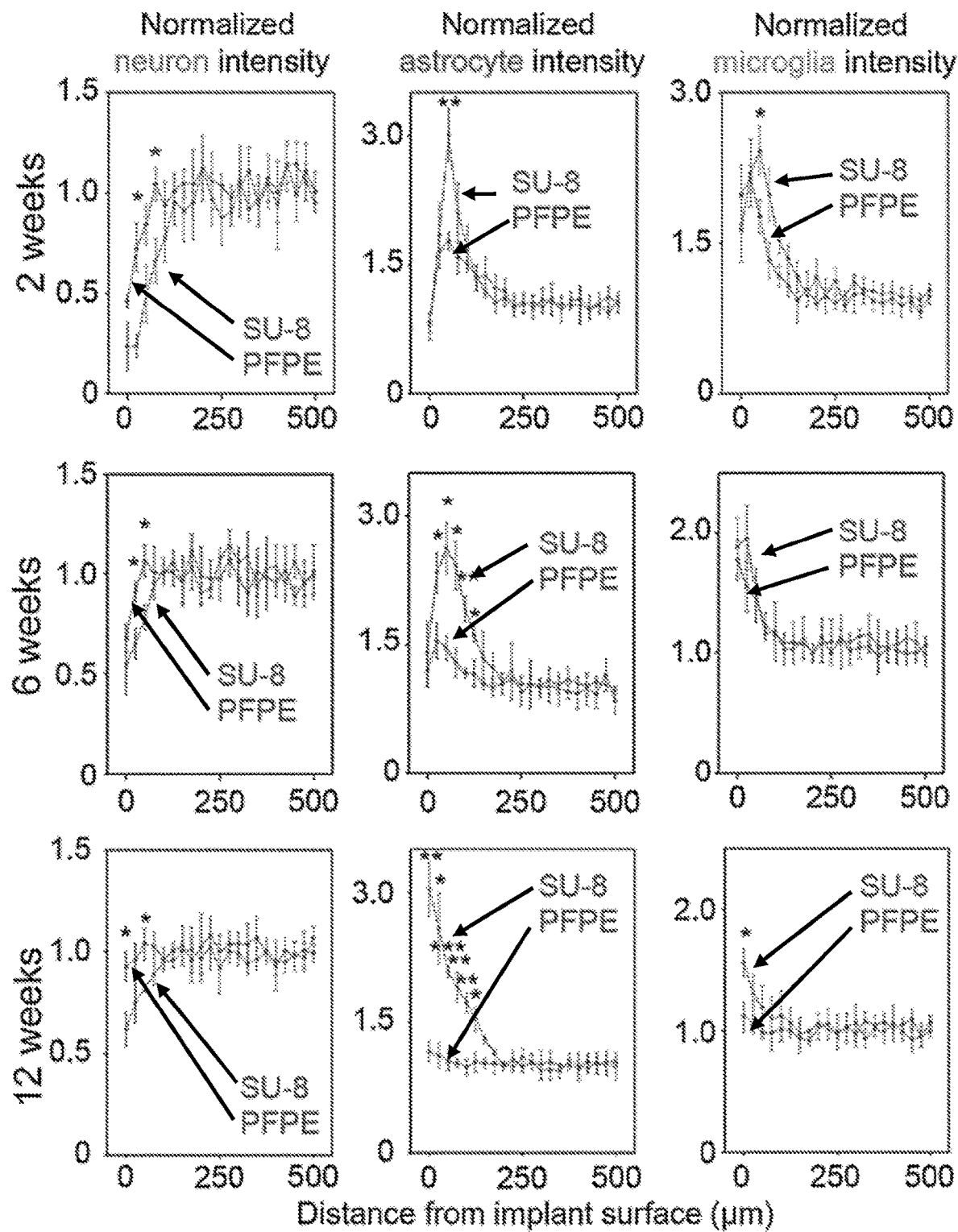
FIG. 34 presents results of exemplary fluorescence measurements of an immune response of a subject to an implanted brain probe, according to certain embodiments.

Normalized average fluorescence intensity of neuron (NeuN), astrocyte (GFAP) and microglia (IBA-1) as a function of distance from the probe boundary at 2, 6, and 12 weeks post-implantation is reported in FIG. 34. Fluorescence intensity at 525-550 µm away from probe surface was used to normalize the data. The reported values are mean±S.D., n=4, *$p<0.05$; $p<0.01$; *$p<0.001$, two-tailed unpaired t-test.

These results indicate the long-term biocompatibility and functionality of exemplary PFPE-DMA brain probes as described herein.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Some embodiments may be embodied as a method, of which various examples have been described. The acts performed as part of the methods may be ordered in any suitable way. Accordingly, embodiments may be constructed in which acts are performed in an order different than illustrated, which may include different (e.g., more or less) acts than those that are described, and/or that may involve performing some acts simultaneously, even though the acts are shown as being performed sequentially in the embodiments specifically described above.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article, comprising:
   a first layer comprising a first perfluoropolyether;
   a second layer, bonded to the first layer, comprising a metal or a metal alloy; and
   a third layer, bonded to the second layer, comprising a second perfluoropolyether, wherein:
   at least one of the first perfluoropolyether and the second perfluoropolyether has a weight-average molecular weight above 20 kDa, and
   at least one of the first perfluoropolyether and the second perfluoropolyether has a reduction in specific electrochemical impedance modulus at 1 kHz of no more than 50% after being immersed for at least 100 days in a 1× phosphate buffer solution at a temperature of 37° C.

2. The article of claim 1, wherein the metal or the metal alloy comprises aluminum, chromium, gold, platinum, copper, silver, or a combination thereof.

3. The article of claim 1, wherein at least one of the first perfluoropolyether and the second perfluoropolyether is a cross-linked perfluoropolyether.

4. The article of claim 1, further comprising one or more additional layers above the third layer.

5. The article of claim 1, wherein the first layer has a minimum dimension that is at least 0.3 micrometers and is less than or equal to 3.0 micrometers.

6. The article of claim 1, wherein at least one of the first perfluoropolyether and the second perfluoropolyether is patterned.

7. The article of claim 6, wherein the pattern of at least one of the first perfluoropolyether and the second perfluoropolyether has a lateral resolution at or below 30 micrometers.

8. The article of claim 1, wherein at least one of the first perfluoropolyether and the second perfluoropolyether exhibits an elastic modulus below 10 MPa.

9. The article of claim 3, wherein the cross-linked perfluoropolyether exhibits elastic tensile deformation at or above 20% strain.

10. The article of claim 1, wherein the article is a portion of a device.

11. The article of claim 1, wherein the article is a sensor.

12. The article of claim 11, wherein the article is a sensor of neural activity.

13. The article of claim 1, wherein at least one of the first perfluoropolyether and the second perfluoropolyether has a reduction in specific electrochemical impedance modulus at 1 kHz of no more than 50% after being immersed for at least 450 days in the phosphate buffer solution.

14. The article of claim 1, wherein at least one of the first perfluoropolyether and the second perfluoropolyether has a reduction in specific electrochemical impedance modulus at 1 kHz of no more than 50% after being immersed for at least 500 days in the phosphate buffer solution.

15. The article of claim 1, wherein the metal or metal alloy forms one or more electrodes, and wherein the article has an electrode area number density of greater than or equal to $10^{-3}$ electrodes/micron$^2$.

16. An article, comprising:
- a first layer comprising a first perfluoropolyether;
- a second layer, bonded to the first layer, comprising a metal or a metal alloy; and
- a third layer, bonded to the second layer, comprising a second perfluoropolyether, wherein:
- at least one of the first perfluoropolyether and the second perfluoropolyether has a weight-average molecular weight above 20 kDa, and
- at least one of the first perfluoropolyether and the second perfluoropolyether has a reduction in specific electrochemical impedance modulus at 1 kHz of no more than 50% after being immersed for at least 5 days in a 10× phosphate buffer solution at a temperature of 70° C.

* * * * *